(12) United States Patent
Boss et al.

(10) Patent No.: US 9,006,175 B2
(45) Date of Patent: *Apr. 14, 2015

(54) POTENTIATION OF GLUCOSE ELIMINATION

(75) Inventors: Anders Hasager Boss, Princeton, NJ (US); Solomon S. Steiner, Mount Kisco, NY (US); Rodney J. Woods, New Hampton, NY (US); Joseph W. Sulner, Paramus, NJ (US)

(73) Assignee: MannKind Corporation, Valencia, CA (US)

( * ) Notice: Subject to any disclaimer, the term of this patent is extended or adjusted under 35 U.S.C. 154(b) by 1442 days.

This patent is subject to a terminal disclaimer.

(21) Appl. No.: 11/329,686

(22) Filed: Jan. 10, 2006

(65) Prior Publication Data

US 2007/0020191 A1   Jan. 25, 2007

Related U.S. Application Data

(60) Continuation of application No. 10/719,734, filed on Nov. 21, 2003, now Pat. No. 7,648,960, which is a continuation of application No. 10/224,761, filed on Aug. 20, 2002, now Pat. No. 6,652,885, which is a division of application No. 09/606,468, filed on Jun. 29, 2000, now Pat. No. 6,444,226.

(60) Provisional application No. 60/667,393, filed on Mar. 31, 2005, provisional application No. 60/643,070, filed on Jan. 10, 2005, provisional application No. 60/141,433, filed on Jun. 29, 1999.

(51) Int. Cl.
*A61K 38/28* (2006.01)
*A61K 9/72* (2006.01)
*A61P 3/08* (2006.01)
*A61K 9/00* (2006.01)
*A61K 9/14* (2006.01)

(52) U.S. Cl.
CPC ............... *A61K 38/28* (2013.01); *A61K 9/0073* (2013.01); *Y10S 514/866* (2013.01)

(58) Field of Classification Search
None
See application file for complete search history.

(56) References Cited

U.S. PATENT DOCUMENTS 3,906,950 A   9/1975   Cocozza
4,211,769 A   7/1980   Okada et al.
(Continued)

FOREIGN PATENT DOCUMENTS

EP   69715   1/1983
EP   122036   10/1984
(Continued)

OTHER PUBLICATIONS

Cefalu et al. "Inhaled Human Insulin Treatment in Patients with Type 2 Diabetes Mellitus," Annals of Internal Medicine, Feb. 2001, 134(3), pp. 203-207.*

(Continued)

*Primary Examiner* — Tracy Vivlemore
*Assistant Examiner* — Monica Shin
(74) *Attorney, Agent, or Firm* — K&L Gates LLP; Louis C. Cullman; Hal Gibson

(57) ABSTRACT

Methods related to the treatment of diabetes and improving the efficiency of insulin utilization are provided. The method enables effective control of prandial glucose levels while reducing the risk of postprandial hypoglycemia. In particular, methods of potentiating the activity of endogenous insulin in type 2 diabetics and exogenous long-acting insulin in diabetics requiring basal insulin replacement are provided.

30 Claims, 19 Drawing Sheets

(56) References Cited

U.S. PATENT DOCUMENTS

| | | | |
|---|---|---|---|
| 4,272,398 | A | 6/1981 | Jaffe |
| 4,294,829 | A | 10/1981 | Suzuki |
| 4,356,167 | A | 10/1982 | Kelly |
| 4,581,020 | A | 4/1986 | Mittleman |
| 4,659,696 | A | 4/1987 | Hirai |
| 4,811,731 | A | 3/1989 | Newell et al. |
| 4,849,227 | A | 7/1989 | Cho |
| 4,861,627 | A | 8/1989 | Mathiowitz |
| 4,866,051 | A | 9/1989 | Hunt et al. |
| 4,946,828 | A | 8/1990 | Markussen |
| 5,006,343 | A | 4/1991 | Benson |
| 5,042,975 | A | 8/1991 | Chien |
| 5,118,666 | A | 6/1992 | Habener |
| 5,120,712 | A | 6/1992 | Habener |
| 5,145,684 | A | 9/1992 | Liversidge et al. |
| 5,188,837 | A | 2/1993 | Domb |
| 5,204,108 | A | 4/1993 | Ilium |
| 5,260,306 | A | 11/1993 | Boardman et al. |
| 5,320,094 | A | 6/1994 | Laube et al. |
| 5,352,461 | A | 10/1994 | Feldstein et al. |
| 5,354,562 | A | 10/1994 | Platz |
| 5,360,614 | A | 11/1994 | Fox et al. |
| 5,364,838 | A | 11/1994 | Rubsamen |
| 5,424,286 | A | 6/1995 | Eng |
| 5,458,135 | A | 10/1995 | Patton et al. |
| 5,482,927 | A | 1/1996 | Maniar |
| 5,484,606 | A | 1/1996 | Dhabhar et al. |
| 5,492,112 | A | 2/1996 | Mecikalski et al. |
| 5,503,852 | A | 4/1996 | Steiner et al. |
| 5,506,203 | A | 4/1996 | Backstrom et al. |
| 5,514,646 | A | 5/1996 | Chance et al. |
| 5,547,929 | A | 8/1996 | Anderson, Jr. et al. |
| 5,562,909 | A | 10/1996 | Allcock et al. |
| 5,574,008 | A | 11/1996 | Johnson et al. |
| 5,577,497 | A | 11/1996 | Mecikalski et al. |
| 5,631,224 | A | 5/1997 | Efendic et al. |
| 5,653,961 | A | 8/1997 | McNally et al. |
| 5,658,878 | A | 8/1997 | Backstrom et al. |
| 5,672,581 | A * | 9/1997 | Rubsamen et al. ............... 514/3 |
| 5,693,338 | A | 12/1997 | Milstein |
| 5,740,794 | A | 4/1998 | Smith et al. |
| 5,747,445 | A * | 5/1998 | Backstrom et al. ............... 514/4 |
| 5,763,396 | A | 6/1998 | Weiner et al. |
| RE35,862 | E | 7/1998 | Steiner et al. |
| 5,785,049 | A | 7/1998 | Smith et al. |
| 5,785,989 | A | 7/1998 | Stanley et al. |
| 5,807,315 | A | 9/1998 | Va Antwerp et al. |
| 5,849,322 | A | 12/1998 | Ebert et al. |
| 5,874,064 | A | 2/1999 | Edwards et al. |
| 5,877,174 | A | 3/1999 | Ono et al. |
| 5,888,477 | A | 3/1999 | Gonda et al. |
| 5,901,703 | A | 5/1999 | Ohki et al. |
| 5,912,011 | A | 6/1999 | Makino et al. |
| 5,929,027 | A | 7/1999 | Takama et al. |
| 5,952,008 | A | 9/1999 | Backstrom et al. |
| 5,976,569 | A | 11/1999 | Milstein |
| 5,985,309 | A | 11/1999 | Edwards et al. |
| 5,997,848 | A | 12/1999 | Patton et al. |
| 6,006,753 | A | 12/1999 | Efendic et al. |
| 6,051,256 | A | 4/2000 | Platz et al. |
| 6,063,910 | A | 5/2000 | Debenedetti et al. |
| 6,071,497 | A | 6/2000 | Steiner et al. |
| 6,099,517 | A | 8/2000 | Daugherty |
| 6,131,567 | A | 10/2000 | Gonda et al. |
| 6,132,766 | A | 10/2000 | Sankaram et al. |
| 6,153,613 | A | 11/2000 | Ono et al. |
| RE37,053 | E | 2/2001 | Hanes et al. |
| 6,187,291 | B1 | 2/2001 | Weinstein et al. |
| 6,191,102 | B1 | 2/2001 | DiMarchi et al. |
| 6,254,854 | B1 | 7/2001 | Edwards et al. |
| 6,277,819 | B1 | 8/2001 | Efendic et al. |
| 6,279,511 | B1 | 8/2001 | Loughnane |
| 6,294,204 | B1 | 9/2001 | Rossling et al. |
| 6,331,318 | B1 | 12/2001 | Milstein |
| 6,335,316 | B1 | 1/2002 | Hughes et al. |
| 6,348,447 | B1 | 2/2002 | Hellstrom et al. |
| 6,358,924 | B1 | 3/2002 | Hoffmann |
| 6,380,357 | B2 | 4/2002 | Hermeling et al. |
| 6,388,053 | B1 | 5/2002 | Galloway |
| 6,395,744 | B1 | 5/2002 | Adams et al. |
| 6,395,774 | B1 | 5/2002 | Milstein |
| 6,410,513 | B1 | 6/2002 | Galloway |
| 6,423,344 | B1 | 7/2002 | Platz et al. |
| 6,428,771 | B1 | 8/2002 | Steiner et al. |
| 6,432,383 | B1 | 8/2002 | Modi |
| 6,436,443 | B1 | 8/2002 | Edwards et al. |
| 6,440,463 | B1 | 8/2002 | Feldstein et al. |
| 6,444,226 | B1 | 9/2002 | Steiner et al. |
| 6,447,751 | B1 | 9/2002 | Weinstein et al. |
| 6,447,753 | B2 | 9/2002 | Edwards et al. |
| 6,503,480 | B1 | 1/2003 | Edwards et al. |
| 6,518,239 | B1 | 2/2003 | Kuo et al. |
| 6,555,521 | B2 | 4/2003 | Hermeling et al. |
| 6,582,728 | B1 | 6/2003 | Platz |
| 6,583,111 | B1 | 6/2003 | DiMarchi et al. |
| 6,592,904 | B2 | 7/2003 | Platz et al. |
| 6,635,283 | B2 | 10/2003 | Edwards et al. |
| 6,652,838 | B2 | 11/2003 | Weinstein et al. |
| 6,652,885 | B2 | 11/2003 | Steiner et al. |
| 6,660,716 | B1 | 12/2003 | Yabuu-Madus et al. |
| 6,676,931 | B2 | 1/2004 | Dugger, III |
| 6,685,967 | B1 | 2/2004 | Patton |
| 6,720,407 | B1 | 4/2004 | Hughes et al. |
| 6,737,045 | B2 | 5/2004 | Patton |
| 6,747,006 | B2 | 6/2004 | Efendic et al. |
| 6,923,175 | B2 | 8/2005 | Poole et al. |
| 6,949,258 | B2 | 9/2005 | Zhang |
| 6,989,155 | B1 | 1/2006 | Ganderton |
| 7,022,674 | B2 | 4/2006 | DeFelippis et al. |
| 7,030,084 | B2 | 4/2006 | Ekwuribe et al. |
| 7,084,243 | B2 | 8/2006 | Glaesner et al. |
| 7,101,843 | B2 | 9/2006 | Glaesner et al. |
| 7,144,863 | B2 | 12/2006 | DeFelippis et al. |
| 7,179,788 | B2 | 2/2007 | DeFelippis et al. |
| 7,211,557 | B2 | 5/2007 | DiMarchi et al. |
| 7,223,728 | B2 | 5/2007 | Yabuku-Madus et al. |
| 7,232,897 | B2 | 6/2007 | Hotamisligil et al. |
| 7,238,663 | B2 | 7/2007 | DeFelippis et al. |
| 7,259,233 | B2 | 8/2007 | Dodd et al. |
| 7,278,419 | B2 | 10/2007 | Gonda et al. |
| 7,279,457 | B2 | 10/2007 | Pohl et al. |
| 7,305,986 | B1 | 12/2007 | Steiner et al. |
| 7,314,859 | B2 | 1/2008 | Green et al. |
| 7,464,706 | B2 | 12/2008 | Steiner et al. |
| 7,625,865 | B2 | 12/2009 | Colombo et al. |
| 7,648,960 | B2 | 1/2010 | Steiner et al. |
| 7,820,676 | B2 | 10/2010 | Leone-Bay et al. |
| 7,943,178 | B2 * | 5/2011 | Steiner et al. ............... 424/489 |
| 7,943,572 | B2 * | 5/2011 | Cheatham et al. ............... 514/5.9 |
| 8,039,431 | B2 | 10/2011 | Wilson et al. |
| 8,119,593 | B2 | 2/2012 | Richardson |
| 8,227,409 | B2 | 7/2012 | Kraft et al. |
| 8,258,095 | B2 | 9/2012 | Boss et al. |
| 8,278,308 | B2 | 10/2012 | Leone-Bay et al. |
| 8,389,470 | B2 | 3/2013 | Steiner |
| 8,394,414 | B2 | 3/2013 | Steiner et al. |
| 8,424,518 | B2 | 4/2013 | Smutney et al. |
| 8,485,180 | B2 | 7/2013 | Smutney et al. |
| 8,512,932 | B2 | 8/2013 | Wilson et al. |
| 8,551,528 | B2 | 10/2013 | Grant et al. |
| 2002/0052381 | A1 | 5/2002 | Bar-Or et al. |
| 2002/0065239 | A1 | 5/2002 | Caplan et al. |
| 2003/0017211 | A1 | 1/2003 | Steiner |
| 2003/0064097 | A1 | 4/2003 | Patel et al. |
| 2003/0068378 | A1 | 4/2003 | Chen et al. |
| 2003/0194420 | A1 | 10/2003 | Holl et al. |
| 2004/0038865 | A1 | 2/2004 | Gelber et al. |
| 2004/0053819 | A1 | 3/2004 | Dodd et al. |
| 2004/0062722 | A1 | 4/2004 | Gonda et al. |
| 2004/0077528 | A1 | 4/2004 | Steiner |
| 2004/0096403 | A1 | 5/2004 | Steiner |
| 2004/0121964 | A1 | 6/2004 | Madar et al. |
| 2004/0138099 | A1 | 7/2004 | Draeger |
| 2004/0151774 | A1 | 8/2004 | Pauletti et al. |

(56) References Cited

U.S. PATENT DOCUMENTS

| | | | |
|---|---|---|---|
| 2004/0157928 A1 | 8/2004 | Kim et al. |
| 2004/0163648 A1 | 8/2004 | Burton |
| 2004/0182387 A1 | 9/2004 | Steiner et al. |
| 2004/0247628 A1 | 12/2004 | Lintz et al. |
| 2005/0043228 A1 | 2/2005 | DeFelippis et al. |
| 2005/0080000 A1 | 4/2005 | Thurow et al. |
| 2005/0153874 A1 | 7/2005 | Cheatham et al. |
| 2005/0187749 A1 | 8/2005 | Singley |
| 2005/0214251 A1 | 9/2005 | Pohl et al. |
| 2006/0040953 A1 | 2/2006 | Leone-Bay et al. |
| 2006/0041133 A1 | 2/2006 | Stevenson et al. |
| 2006/0099269 A1 | 5/2006 | Cheatham et al. |
| 2006/0120969 A1 | 6/2006 | Nilsson et al. |
| 2006/0153778 A1 | 7/2006 | Gelber et al. |
| 2006/0160722 A1 | 7/2006 | Green et al. |
| 2006/0165756 A1 | 7/2006 | Catani et al. |
| 2006/0239934 A1 | 10/2006 | Cheatham et al. |
| 2007/0020191 A1 | 1/2007 | Boss et al. |
| 2007/0027063 A1 | 2/2007 | Boss et al. |
| 2007/0059373 A1 | 3/2007 | Oberg |
| 2007/0059374 A1 | 3/2007 | Hokenson et al. |
| 2007/0086952 A1 | 4/2007 | Steiner |
| 2007/0196503 A1 | 8/2007 | Wilson et al. |
| 2007/0207958 A1 | 9/2007 | Bridon et al. |
| 2007/0240708 A1 | 10/2007 | Schuckmann |
| 2008/0015457 A1 | 1/2008 | Silva |
| 2008/0255468 A1 | 10/2008 | Derchak et al. |
| 2008/0260838 A1 | 10/2008 | Hokenson et al. |
| 2008/0260840 A1 | 10/2008 | Alessi |
| 2009/0110647 A1 | 4/2009 | Richardson |
| 2009/0111749 A1 | 4/2009 | Richardson et al. |
| 2009/0149727 A1 | 6/2009 | Truitt et al. |
| 2009/0151720 A1 | 6/2009 | Inoue et al. |
| 2009/0258818 A1 | 10/2009 | Surolia et al. |
| 2009/0308390 A1 | 12/2009 | Smutney et al. |
| 2010/0086609 A1 | 4/2010 | Steiner et al. |
| 2010/0113363 A1 | 5/2010 | Holst et al. |
| 2011/0000482 A1 | 1/2011 | Gumaste et al. |
| 2011/0183901 A1* | 7/2011 | Cheatham et al. ............ 514/6.5 |
| 2012/0040899 A1 | 2/2012 | Costello |
| 2012/0071510 A1 | 3/2012 | Leone-Bay et al. |
| 2012/0094905 A1 | 4/2012 | Costello |
| 2012/0115777 A1 | 5/2012 | Richardson |
| 2012/0122775 A1 | 5/2012 | Boss et al. |
| 2012/0164186 A1 | 6/2012 | Grant et al. |
| 2013/0104887 A1 | 5/2013 | Smutney et al. |
| 2013/0125886 A1 | 5/2013 | Richardson |
| 2013/0143801 A1 | 6/2013 | Steiner et al. |
| 2013/0199527 A1 | 8/2013 | Smutney et al. |

FOREIGN PATENT DOCUMENTS

| | | |
|---|---|---|
| EP | 220958 | 5/1987 |
| EP | 0220958 | 5/1987 |
| EP | 237507 | 8/1987 |
| EP | 257915 | 2/1988 |
| EP | 360340 | 3/1990 |
| EP | 364235 | 4/1990 |
| EP | 606486 | 12/1993 |
| EP | 655237 | 5/1995 |
| EP | 1114644 | 7/2001 |
| EP | 1364967 | 11/2003 |
| EP | 96911738 | 6/2004 |
| EP | 1598066 | 11/2005 |
| EP | 2060268 | 5/2006 |
| GB | 2240337 | 7/1991 |
| JP | 63-020301 | 1/1988 |
| JP | 02-149545 | 2/1991 |
| JP | 09-208485 | 8/1997 |
| JP | 2003/503420 | 1/2003 |
| WO | 90/13285 | 11/1990 |
| WO | 91/04011 | 4/1991 |
| WO | 91/16882 | 11/1991 |
| WO | 92/04069 | 3/1992 |
| WO | 92/08509 | 5/1992 |
| WO | 93/02712 | 2/1993 |
| WO | 93/14110 | 7/1993 |
| WO | 93/17728 | 9/1993 |
| WO | 93/18754 A1 | 9/1993 |
| WO | 94/00291 | 1/1994 |
| WO | 94/08552 | 4/1994 |
| WO | 94/08599 | 4/1994 |
| WO | 94/23702 | 10/1994 |
| WO | 95/00127 A1 | 1/1995 |
| WO | 95/11666 | 5/1995 |
| WO | 95/24183 | 9/1995 |
| WO | 95/31979 | 11/1995 |
| WO | 95/34294 | 12/1995 |
| WO | 96/05810 | 2/1996 |
| WO | 96/32149 | 10/1996 |
| WO | 96/36314 | 11/1996 |
| WO | 97/04747 | 2/1997 |
| WO | 97/46206 | 12/1997 |
| WO | 97/49386 | 12/1997 |
| WO | 98/43615 | 10/1998 |
| WO | 99/33862 | 7/1999 |
| WO | 99/52506 | 10/1999 |
| WO | 01/00654 A2 | 1/2001 |
| WO | 01/07107 | 2/2001 |
| WO | 02/11676 | 2/2002 |
| WO | 02/098348 | 12/2002 |
| WO | 03/057170 | 7/2003 |
| WO | 03/086345 | 10/2003 |
| WO | 03/094951 | 11/2003 |
| WO | 2004/012720 | 2/2004 |
| WO | 2004/056314 | 7/2004 |
| WO | 2004/064862 | 8/2004 |
| WO | 2004/075919 | 9/2004 |
| WO | 2004/080401 | 9/2004 |
| WO | 2004/103304 | 12/2004 |
| WO | 2005/067964 A1 | 7/2005 |
| WO | 2005/089722 | 9/2005 |
| WO | 2006/023943 | 3/2006 |
| WO | 2007/030706 | 3/2007 |
| WO | 2007/033316 | 3/2007 |
| WO | 2007/100535 | 9/2007 |
| WO | 2007/121411 | 10/2007 |
| WO | 2009/055742 | 4/2009 |
| WO | 2011/163272 | 12/2011 |

OTHER PUBLICATIONS

Vølund, A., "Conversion of insulin units to SI units," American Journal of Clinical Nutrition, Nov. 1993, 58(5), pp. 714-715.*

Patton et al., "Inhaled Insulin", Advanced Drug Delivery Reviews, 35, (Feb. 1999), p. 235-247.*

Heinemann et al., "Time-action Profile of Inhaled Insulin", Diabetic Medicine, 1997; 14: p. 63-72.*

DedicatedPhase, "Preclinical Trials and Research", <http://www.dedicatedphase1.com/preclinical-research.html>, copyright 2006-2011, p. 1.*

Crosby, J., "Dog Normals", <http://vetmedicine.about.com/od/diseasesconditionsfaqs/tp/TP_dogfacts.htm>, copyright 2013, p. 1-3.*

Zimmermann, K., "Respiratory System: Facts, Function, and Diseases", <www.livescience.com/22616-respiratory-system.html>, copyright 2013, p. 1.*

Heinemann, L., "Intra-individual Variability of the Metabolic Effect of Inhaled Insulin Together With an Absorption Enhancer", Diabetes Care, vol. 23, No. 9, Sep. 2000., p. 1343-1347.*

Lindmark, T. et al., "Mechanism of Absorption Enahncement in Humans After Rectal Administration of Ampicillin in Suppositories Containing Sodium Caprate," Pharmaceutical Research, vol. 14, No. 7, 1997, p. 930-935.*

Maher, S., et al., "Safety and efficacy of sodium caprate in promoting oral drug absorption: from in vitro to the clinic," Advanced Drug Delivery Reviews Advanced Drug Delivery Reviews 61 (2009) 1427-1449.*

Cefalu WT. Concept, strategies and feasibility of noninvasive insulin delivery. Diabetes Care 27:239-246, 2004.

(56) References Cited

OTHER PUBLICATIONS

Cerasi, et al. Decreased sensitivity of the pancreatic beta cells to glucose in prediabetic and diabetic subjects. A glucose dose-response study. Diabetes 21(4):224-34, 1972.
Gupta et al. Contemporary approaches in aerosolized drug delivery to the lung. J Controlled Resease 17:129-148, 1991.
Heinemann L et al. Current status of the development of inhaled insulin. Br J Diabetes Vasc Dis 4:295-301, 2004.
Leahy et al. Beta-cell dysfunction in type II diabetes mellitus. Curr Opin Endocrinol Diabetes 2:300-306, 1995.
Lian et al. A self-complementary self-assembling microsphere system: application for intravenous delivery of the antiepileptic andneuroprotectant compound felbanate. J Pharm Sci 89:867-875, 2000.
Pfeiffer MA et al. Insulin secretion in diabetes mellitus. Am J Med 70:579-88, 1981.
Polonsky et al. Abnormal patterns of insulin secretion in non-insulin-dependent diabetes mellitus. N Eng J Med 318:1231-39, 1988.
Steiner S et al. Technosphere(TM)/Insulin—proof of concept study with a new insulin formulation for pulmonary delivery. Exp Clin Endocrinol Diabetes 110:17-21, 2002.
Edelman SV Type II diabetes mellitus. Adv Int Med 43:449-500, 1998.
Kohler D et al. Non-radioactive approach for measuring lung permeability: inhalation of insulin. Atemw Lungenkrkh 13:230-232, 1987. (Original German and English translation attached).
Farr, SJ et al. "Pulmonary insulin administration using the AERx(R) system: physiological and physiochemical factors influencing insulin effectiveness in healthy fasting subjects," Diabetes Tech. Ther. 2:185-197, 2000.
Hussain A. and Ahsan F "State of insulin self-association does not affects its absorption from the pulmonary route." Eur. J. Pharm. Sciences 25:289-298, 2005.
Raz I et al. "Pharmacodynamics and pharmacokinetics of dose ranging effects of Oralin versus s.c. regular insulin in Type 1 diabetic patients." Fourth Annual Diabetes Technology Meeting, Philadelphia, PA, 2004.
Cheatham et al. "Desirable dynamics & performance of inhaled insulin compared to subcutaneous insulin given at mealtime in type 2 diabetes: A report from the technosphere/insulin study group." Diabetes Technology and Therapeutics, vol. 6, p. 234 (2004).
Perera et al. "Absorption and Metabolic Effect of Inhaled Insulin." Diabetes Care, vol. 25, No. 12, Dec. 2002, p. 2276-2281.
Pfutzner et al. "Technosphere/Insulin—A New Approach for Effective Delivery of Human Insulin Via the Pulmonary Route." Diabetes Technology & Therapeutics, vol. 4, No. 5, prs. 589-594, 2002.
EP Office Action, Application No. 10 005 945.0 mailed Dec. 28, 2011.
US Office Action cited in U.S. Appl. No. 12/985,197, mailed on Jan. 20, 2012.
Engwerda et al., "Improved Pharmacokinetic and Pharmacodynamic Profile of Rapid-Acting Insulin Using Needle-Free Jet Injection Technology." Diabetes Care, vol. 34, Aug. 2011, pp. 1804-1808.
Toft-Nielson et al., "Determinants of the effextiveness of glucagon-like peptide=1 in type 2 diaetes", J. Clin Endocrino Metab 86:3653, 2001.
Toft-Nielson et al., "Exaggerated secretion of glucaton-like peptide-1 (GLP-1) could cause reaxtive hypoglicaemia", Diabetologia 41:1180, 1998.
Toft-Nielson et al., The Effect of Glucagon-Like peptide-1 (GLP-1) on glucose elimination in healthy subjects depends on the pancreatic glucoregulatory hormones, Diabetes 45:552, 1996.
Tornusciolo et al., Biotechniques 19(5):800-805, 1995. Simultaneous detection of TDT-mediated dUTP-biotin nick end-labeling (TUNEL)-positive cells and multiple immunohistochemical markers in single tissue sections.
Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.

Van Alfen-Van Der Velden et al. "Successful treatment of severe subcutaneou insulin resistance with inhaled insulin therapy", Pediatric Diabetes 2010: 11:380-382.
Vara et al. "Glucagon-like peptide-1 (7-36) amide stimulates surfactant secretion in human type II pneumocytes." Am J Resp Crit Care Med 163:841, 2001.
Vella et al. "Effect of glucagon-like peptide 1(7-36) amide on glucose effectiveness and insulin action in people with type 2 diabetes." Diabetes 49:611, 2000.
Vella et al. "The gastrointestinal tract and glucose tolerance." Curr Opin Clin Nutr Metab Care 7:479, 2004.
Vendrame et al. "Prediabetes: prediction and prevention trials." Endocrinol Metab Clin N Am, 2004, vol. 33, pp. 75-92.
Verdich et al., A meta-analysis of the effect of glucagon-like peptide-1 (7-36) amide on ad libitum energy intake in humans. J Clin Endocrinol Metab., 86:4382-4389, 2001.
Vilsboll et al. "Reduced postprandial concentrations of intact biologically active glucagon-like peptide-1 in type 2 diabetic patients." Diabetes 50:609, 2001.
Vilsboll et al. "Similar elimination rates of glucagon-like peptide-1 in obese type 2 diabetic patients and healthy subjects." J Clin Endocrinol Metab 88:220, 2003.
Vilsboll et al., "Evaluation of β-Cell Secretary Capacity Using Glucagon-Like Peptide 1", Diabetes Care, vol. 23, No. 6, pp. 807-812, Jun. 2000.
Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 regulates proliferation and apoptosis via activation of protein kinase B in pancreatic INS-1 beta cells. Diabetologia, 47:478-487, 2004.
Wang et al., J. Clin. Invest., 95:417-21, 1995.
Wareham et al., "Fasting Proinsulin Concentrations Predict the Development of Type 2 Diabetes", Diabetes Care, 1999, 22, 262-70.
Warren et al. "Postprandial versus Prepandial Dosing of Biphasic Insulin Aspart in Elderly Type 2 diabetes Patients", Diabetes Research and Clinical practice, vol. 66, pp. 23-29, 2004.
Waterhouse et al., "Comparatie assessment of a new breath-actuated inhaler in patients with reversible airways obstruction", Respiration 59:155-158 (1992).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.
Wettergren et al. "Truncated GLP-1 (proglucagon 78-107-Amide) inhibits gastric and pancreatic functions in man." Digestive Diseases and Sciences 38:665, 1993.
Wigley et al., Insulin across respiratory mucosae by aerosol delivery. Diabetes 20(8): 552-556 (1971).
Willms et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson et al. "Technospheres(TM) for pulmonary and nasal applications." Respiratory Drug Delivery VIII, 2002, p. 545.
Witchert, Low molecular weight PLA: A suitable polymer for pulmonary administered microparticles. J. Microencapsulation, 10(2): 195-207 (1993).
Wong et al. "From cradle to grave: pancreatic b-cell mass and glucagon-like peptide-1." Minerva Endocrinologica 31:107, 2006.
Yoshida et al., Absorption of insulin delivered to rabbit trachea using aerosol dosage form. J. Pharm. Sci. 68(5): 670-671 (1979).
Yoshioka et al., "Serum proinsulin levels at fasting and after oral glucose load in patients with Type 2 (non-insulin dependent) diabetes mellitus", Diabetogia, 1988, 31, 355-60.

(56) References Cited

OTHER PUBLICATIONS

Yusta et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
ACTOS Product Insert. Aug. 2008.
Adjusting Mealtime Insulin Doses. BD Diabetes. http://www.bd.com/us/diabetes/page.aspx?cat=7001&id=7280, retrieved 2014.
Ahren et al. "Characterization of GLP-1 effects on b-cell function after meal ingestion in humans." Diabetes Care 26:2860, 2003.
Ahren, "GLP-1 and extra-islet effects", Horm Med Res 36:842, 2004.
Alabraba et al. Diabetes Technology & Therapeutics. Jul. 2009, 11(7): 427-430.
Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.
American Diabetes Association, "Standards of medical care in diabetes—2009", Diabetes Care, Jan. 2009, 32 Suppl 1: S13-61.
Angelo et al., Technosphere Insulin: Defining the Role of Technosphere Particles at the Cellular Level. J. Diabetes Sci. Technol., vol. 3, Issue 3, pp. 545-554 (2009).
Ashwell et al. "Twice-daily compared with once-daily insulin glargine in people with Type 1 diabetes using meal-time insulin aspart." 2006 Diabetes UK, Diabetic Medicine, 23, 879-886.
Ashwell et al., "Optimal timing of injection of once-daily insulin gargine in people with Type 1 diabetes using insulin lispro at meal-times" 2005 Diabetes UK, Diabetic Medicine, 23, 46-52.
Avandia Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.
Balkan et al. "Portal GLP-1 administration in rats augments the insulin response to glucose via neuronal mechanisms." Am J. Physiol Regulatory Integrative Comp Physiol 279:R1449, 2000.
Barnett et al. "An open, randomized, parallel-group study to compare the efficacy and safety profile of inhaled human insulin (Exubera) with Glibenclamide as adjunctive therapy in patients with Type 2 diabetes poorly controlled on Metformin." Diabetes Care 29:1818 - 1825, 2006.
Barragan et al. "Changes in arterial blood pressure and heart rate induced by glucagon-like peptide-1-(7-36) amide in rats." Am J. Physiol 266 (Endocrinol Metab 29):E459, 1994.
Basu, A. et al. "Effects of a change in the pattern of insulin delivery on carbohydrate tolerance in diabetic and nondiabetic humans in the presence of differing degrees of insulin resistance." J. Clin. Invest. 97:2351-2361, 1996.
Bauer et al., "Assessment of beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Belmin J et al. "Novel drug delivery systems for insulin. Clinical potential for use in the elderly." Dugs Aging 20:303-12, 2003.
Benita, Charaterization of Drug-Loaded Poly(d,l-lactide) Microspheres. J. Pharm. Sci., 73: 1721-1724 (1984).
Benito et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier, Science 156: 1204-1206 (1967).
Berge et al., "Pharmaceutical Salts", J. Pharmaceutical Sciences 66(1):1-19 (1977).
Biodel's Intellecutal Property position strengthened for ultra-rapid-acting insulin programs by notice of intent to grant from European Patent Office. Newswire Fee, published May 2, 2012.
Blazquez et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 200, published 2005.
Bonner-Weir S et al. "New sources of pancreatic beta-cells." Nat Biotechnol 23:857-61, 2005.
Boss et al. "Insulin bioeffect is limited by speed of absorption and elimination: similarities between an inhaled insulin formulation that mimics first-phase kinetics and i.v. insulin." Diabetologia 47:A314, 2004.
Boss et al. "Prandial Insulin: Is Inhaled Enough?" Drug Development Research 69(3):138-142 (2008).
Brange et al., "Insulin Structure and Stability", Pharm Biotechnol, 5:315-50 (1993).
Bray "Exanatide" Am J Health-Sys Pharm 63:411, 2006.
Brownlee M and Hirsch IB "Glucemic variability: a hemoglobin A1c-independent risk factor for diabetic complications." JAMA 295:1707-1708, 2006.
Bruce, D.G., et al. "Physiological importance of deficiency of early prandial insulin secretion in non-insulin-dependent diabetes." Diabetes 37:736-44, 1988.
Bullock et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.
Calles-Escandon, J. and Robbins, D.C. "Loss of early phase insulin release in humans impairs glucose tolerance and blunts thermic effect of glucose." Diabetes 36:1167-72, 1987.
Camilleri et al., The NEJM 356: 820-829, published 2007.
Campos et al. "Divergent tissue-specific and developmental expression of receptors for glucagon and glucagon0like peptide-1 in the mouse." Endocrinology 134:2156, 1994.
Caumo, A. and Luzi, L. "First-phase insulin secretion: does it exist in real life? Considerations on shape and function." Am. J. Physiol. Endocrinol. Metab. 284:E371-E385, 2004.
Cefalu WT "Novel routes of insulin delivery for patients with type 1 or type 2 diabetes." Ann Med 33:579-586, 2001.
Ceglia et al. "Meta-analysis: efficacy and safety of inhaled insulin therapy in adults with diabetes mellitus." Ann Intern Med 145:665, 2006.
Cernea et al. "Dose-Response Relationship of Oral Insulin Spray in Healthy Subjects." Diabetes Care, vol. 28, No. 6, pp. 1353-1357, 2005.
Cernea et al. "Noninjectable Methods of Insulin Administration." Drugs of Today 2006, 42 (6): 405-424.
Chan et al., "Pharmacological Management of Type 2 Diabetes Mellitus: Rationale for Rational Use of Insulin", Mayo Clin Proc, 2003, 78, 459-466.
Chase et al., "Redefining the clinical remission period in children with type 1 diabetes", Pediatric Diabetes, 2004, 5, 16-19.

(56) References Cited

OTHER PUBLICATIONS

Cheatham et al., A novel pulmonary insulin formulation replicates first phase insulin release and reduces s-proinsulin levels. 457-P (2004).
Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Clee, SM et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing heath-related quality of life in diabetes." Diabetes Care 25:2238, 2002.
Combettes and Kargar, C, Newly Approved and Promising Antidiabetic Agents. Therapie, Jul.-Aug. 2007, : 62 (4):293-310.
Costello et al., "Zinc inhibition of mitochondrial aconitase and its importance in citrate metabolism in prostate epithelial cells", Journ. Biol. Chem. 272(46):28875-28881 (1997).
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., J. Clin. Invest., 97:133-38, 1996.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like peptide-1." Diabetes 56:438, 2007.
Deacon "Therapeutic strategies based on glucagon-like peptide 1." Diabetes. Sep;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
Del Prato S "Unlocking the opportunity of tight glycemic control" Diabetes Obesity and Metabolism 7:S1-S4, 2005.
Delgado-Aros et al. "Effect of GLP-1 on gastric volume, emptying, maximum vol. ingested and postprandial symptoms in humans." Am J Physiol Gastrointest Liver Physiol 282:G424, 2002.
Diabetes: Counting Garbs if You Use Insulin, WedMD, http://diabetes.webmd.com/carbohydrate-counting-for-people-who-use-insulin#m Oct. 1, 2010.
Diez et al. "Inhaled insulin—a new therapeutic option in the treatment of diabetes mellitus" Expert Opin. Pharmacother., 2003, 4, 191-200.
Doyle et al. "Glucagon-like peptide-1." Recent Prog Norm Res. 2001;56:377-99.
Drucker "Development of glucagon-like peptide-1-based pharmaceuticals as therapeutic agents for the treatment of diabetes." Curr Pharma Design 7:1399, 2001.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Dunn, "Zinc-ligand interactions modulate assembly and stability of the insulin hexamer", Biometals, 18(4):295-303 (2005).
Edited by Fukushima, Masanori, "Arterial Sclerosis," Merck Manual 17th, Japanese Edition, NIKKEI BP Corp., p. 1659-1663, 1999.
Edwards et al. "Cardiovascular and pancreatic endocrine response to glucagon-like peptide-1(7-36) amide in the conscious calf." Exp Physiol 82:709, 1997.
Edwards et al. "Subcutaneous glucagon-like peptide-1(7-36) amide is insulinotropic and can cause hypoglycaemia in fasted healthy subjects." Clinical Science 96:719, 1998.
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Life Sci., 55:629-34, 1994.
Elliott et al., "Parenteral absorption of insulin from the lung in diabetic children", Aust. Paediatr. J. 23:293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Fehmann et al. "Cell and molecular biology of the incretin hormones glucagon-like peptide-1 and glucose-dependent insulin releasing polypeptide." Endocrine Reviews 16:390, 1995.
Festa et al., "LDL particle size in relation to insulin, proinsulin, and insulin sensitivity" Diabetes Care, 22 (10):1688-1693 (1999).
Forst et al., "Metabolic Effects of Mealtime Insulin Lispro in Comparison to Glibenclamide in Early Type 2 Diabetes", Exp. Clin. Endocrinol. Diabetes, 2003, 111, 97-103.
Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.
Garber, "Premixed insulin analogues for the treatment of diabetes mellitus", Drugs, 66(1):31-49 (2006).
Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.
Glucophage Product Insert. Jan. 2009.
Glucotrol Product Insert. Sep. 2006.
Richter et al. "Characterization of receptors for glucagon-like peptide-1 (7-36)amide on rat lung membranes." FEBS Letters 267:78, 1990.
Riddle "Combining Sulfonylureas and Other Oral Agents." Am J Med, 2000, vol. 108(6A), pp. 15S-22S.
Riddle et al. "Emerging therapies mimicking the effects of amylin and glucagon-like peptide 1." Diabetes Care 29:435, 2006.
Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.
Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, Aug. 2008.
Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J et al. "Inhaled insulin improves glycemic control when substituted for or added to oral combination therapy in Type 2 diabetes." Ann Intern Med 143:549-558, 2005.
Ryan EA et al. "Successful islet transplantation. Continued insulin reserve provides long-term glycemic control." Diabetes 51:2148-2157, 2002.
Sakagami M et al. "Respirable microspheres for inhalation: the potential of manipulating pulmonary disposition for improved therapeutic efficacy." Clin Pharmacokinet 44:163-77, 2005.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni et al. "Effects of glucagon-like peptide-1 and long-acting analogues on cardiovascular and metabolic function." Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.
Sawhney, Bioerodible hydrogels based on photopolymerized poly-(ethylene glycol)-co-poly(a-hydroxy acid) diacrylate macromers. Macromolecules, 26: 581-587 (1993).

(56) References Cited

OTHER PUBLICATIONS

Schaffer et al. "Assembly of high-affinity insulin receptor agonists and antagonists from peptide building blocks." PNAS 100:4435, 2003.
Schepp et al., Eur. J. Pharmacol., 69:183-91, 1994.
Scherbaum "Unlocking the opportunity of tight glycaemic control. Inhaled insulin: clinical efficacy." Diabetes Obesity and Metabolism 7:S9, 2005.
Schirra et al. "Gastric emptying and release of incretin hormones after glucose ingestion in humans." J Clin Invest 97:92, 1996.
Schluter et al., "Pulmonary Administration of Human Insulin in volunteers and Type I Diabetics", Diabetes, 33, (Suppl) 298 (1984).
Schneider et al., "Stimulation by proinsulin of expression of plasminogen axtivator inhibiror type 1 in endothelial cells", Diabetes 41(7):890-895 (1992).
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254, 1996.
Seshiah & Balaji, "Early Insulin Therapy in Type 2 Diabetics", Int. J. Diabetes in Developing Countries, 2003, 23, 90-93.
Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shojania et al. "Effect of quality improvement strategies for type 2 diabetes on glycemic control." JAMA 296:427, 2006.
Silverstein et al., "Care of Children and Adolescens with Type 1 Diabetes, A Statement of the American Diabetes Association", Diabetes Care, Jan. 2005, vol. 28, p. 186-212.
Singh, et al., Regul. Pept. 53:47-59, 1994.
Skyler "Pulmonary Insulin Delivery—State of the Art 2007." Diabetes Tecnology & Therapeutics, vol. 9, Supplement 1, pp. S1-S3. 2007.
Skyler JS et al. "Use of inhaled insulin in a basal/bolus insulin regimen in Type 1 diabetic subjects." Diabetes Care 28:1630-1635, 2005.
Smith et al. "New-onset diabetes and risk of all-cause and cardiovascular mortality." Diabetes Care 29:2012, 2006.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al., "A novel glucagon delivery system for the management of hyperinsulinemia", Diabetes 49 Supplement, Abstract, 1545-PO, 2000.
Steiner, K. et al. "The relative importance of first- and second-phase insulin secretion in countering the action of glucagon on glucose turnover in the conscious dog." Diabetes 31:964-972, 1982.
Stowell et al. "Development of GLP-1 Technosphere(TM) powder: an inhaled GLP-1 product." Diabetes Technology Meeting, San Francisco, Oct. 2007.
Strack "Inhaled Human Insulin." Drugs of Today 2006, 42 (4): 207-221.
Sturis et al., British Journal of Pharmacology, 140,123 .132, 2003.
Tack Cees J. et al., Forced Titration to Different Doses of Technosphere Insulin Demonstrates Reduction in Postprandial Glucose Excursions and Hemoglobin A1c in Patients with Type 2 Diabetes. Journal of Diabetes Science and Technology, vol. 2, Issue 1, pp. 47-57, Jan. 2008.
Tang-Christensen et al. "Central administration of GLP-1-(7-36) amide inhibits food and water intake in rats." Am J Physiol 271 (Regulatory Integrative Comp Physiol 40):R848, 1996.
Teeter et al. "Dissociation of lung function changes with humoral immunity during inhaled human insulin therapy." Am J Resp Crit Care Med 173:1194, 2006.
The American Diabetes Association "Insulin Administration" Diabetes Care, vol. 27, Supplement 1, S106-S109 (2004).
The DECODE study group. "Glucose tolerance and mortality: comparison of WHO and American Diabetes Association diagnostic criteria." Lancet. Aug. 21, 1999;354(9179):617-21.
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.
Thorens et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in on-insulin-dependent diabetes mellitus." Eur J Clin Invest 27:533, 1997.
Goke et al., J. Biol. Chem. 268:19650-55, 1993.
Golpon et al. "Vasorelaxant effect of glucagon-like peptide-(7-36) amide and amylin on the pulmonary circulation of the rat." Regulatory Peptides 102:81, 2001.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects nad patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Haak "New developments in the treatment of type 1 diabetes mellitus." Exp Clin Endocrinol Diabetes 107:Suppl 3: S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Halozyme Press Release. Jun. 6, 2009.
Hanley et al., "Cross-sectional and prospective associations between proinsulin and cardovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121, e466-e472, 2008.
Hassan et al. "In vivo dynamic distribution of 1311-glucagonOlike peptide-1 (7-36) amide in the rat studied by gamma camera." Nucl Med Biol 26:413, 1999.
Hausmann M et al. "Inhaled insulin as adjunctive therapy in subjects with type 2 diabetes failing oral agents: a controlled proof-of-concept study." Diabetes Obesity Metab 8:574-580, 2006.
Hayasaka et al. "Proliferation of type II pneumocytes and alteration in their apical surface membrane antigenicity in pulmonary sarcoidosis." Chest 116:477, 1999.
Heine "Unlocking the opportunity of tight glycaemic control. Promise ahead: the role of inhaled insulin in clinical practice." Diabetes, Obesity and Metabolism 7:S19, 2005.

(56) References Cited

OTHER PUBLICATIONS

Heinemann "Variability of Insulin Absorption and Insulin Action." Diabetes Technology & Therapeutics, vol. 4, No. 5, pp. 673-682. 2002.
Heise et al. "The effect of insulin antibodies on the metabolic action of inhaled and subcutaneous insulin." Diabetes Care 28:2161, 2005.
Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. Both original and translated documents included.
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Acad Sci. Dec. 26, 1996;805:729-36.
Huda et al. "Gut peptides and the regulation of appetite." Obesity Reviews 7:163, 2006.
Imeryuz et al. "Glucagon-like peptide-1 inhibits gastric emptying via vagal afferent-mediated central mechanisms." Am J Physiol 273 (Gastrointest Liver Physiol 36):G920, 1997.
International Search Report for PCT/US2011/060057 mailed on Jan. 20, 2012.
Iwanij et al., Characterization of the Glucagon Receptor and its Functional Domains Using Monoclonal Antibodies. The Journal of Biological Chemistry, vol. 265, No. 34, pp. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al. "Peptide turn mimetics." in Biotechnology and Pharmacy, Ed JM Pezzuto et al. Chapman & Hall, New York, pp. 366, 1993.
Johnson et al., "Turbuhaler a new device for dry powder terbutaline inhalation", Allergy 43(5):392-395 (1988).
Johnson et al: RyR2 and calpain-10 delineate a novel apoptosis pathway in pancreatic islets. J Biol Chem., 279 (23):24794-802, 2004.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." . Diabetologia 43:1319, 2000.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care, vol. 19, No. 11, p. 1200-1206, 1996.
Kanse et al. "Identification and characterization of glucagon-like peptide-1 7-36 amide-binding sites in the rat brain and lung." FEBS Letters 241:209, 1988.
Kapitza et al. "Impact of particle size and aerosolization time on the metabolic effect of an inhaled insulin aerosol." Diabetes Tech Ther 6:119, 2004.
Katchalski, Synthesis of Lysine Anhydride. J. Amer. Chem. Soc. 68: 879-880 (1946).

Katz, A. et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Ne-(Fumaroyl)diketopiperazine of L-Lys (FDKP) Interactions." Molecular Pharmaceutics, vol. 5, No. 2, 294-315, 2008.
Kawai et al. "Evidence that glucagon stimulates insulin secretion through its own receptor in rats." Diabetologia 38:274, 1995.
Kelley, D. et al. "Impaired postprandial glucose utilization in non-insulin dependent diabetes mellitus." Metabolism 43:1549-1557, 1994.
Kenny et al. "Dipeptidyl peptidase IV, a kidney brush-border serin peptidase." Biochem J. 155:169, 1976.
Kieffer et al. "The glucagon-like peptides." Endocrine Reviews 20:876, 1999.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between african-american and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902,1989.
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kopple, A convenient synthesis of 2,5-piperazinediones. J. Org. Chem., 33(2): 862-864 (1968).
Kreymann et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Kwon et al. "Signaling elements involved in the metabolic regulation of mTOR by nutrients, incretins, and growth factors in islets." Diabetes 53:S225, 2004.
Lankat-Buttgereit et al. "Molecular cloning of a cDNA encoding for the GLP-1 receptor expressed in rat lung." Exp Clin Endocrinol 102:241, 1994.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leone-Bay et al. "Evaluation of novel particles as an inhalation system for GLP-1." Diabetes, Obesity and Metabolism. 11:1050-1059, 2009.
Li et al. "GLP-1; a novel zinc finger protein required in somatic cells of the gonad for germ cell development." Dev Biol 301:106, 2007.
Lim, "Microencapsulation of Living Cells and Tissues", J. Pharm. Sci., 70: 351-354 (1981).
Liu et al., "Pulmonary delivery of free and liposomal insulin", Pharmaceuticals Res. 10:228-232, 1993.

(56) References Cited

OTHER PUBLICATIONS

Luque et al. "Glucagon-like peptide-1 (GLP-1) and glucose metabolism in human myocytes." J. Endocrinol 173:465, 2002.
Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.
Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.
Malhotra et al., Regulatory Peptides, 41:149-56, 1992.
Mandal TK "Inhaled insulin for diabetes mellitus." Am J Health Syst Pharm 62:1359-64, 2005.
Mannkind Corporation "Postprandial hyperglycemia: clinical significance, pathogenesis and treatment." MannKind Corporation Monograph. 2009.
Marshall "Preventing and detecting complications of diabetes." BMJ 333:455, 2006.
Mastrandrea "A breath of life for inhaled insulin: sever subcutaneous insulin resistance as an indication." Pediatric Diabetes 2010: 11: 377-379.
Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hot-melt microencapsulation. J. Controlled Medicine, 5: 13-22 (1987).
Mathiowitz, Polyanhydride microspheres as drug carriers II, microencapsulation by solvent removal. J. Appl. Polymer Sci., 35: 755-774 (1988).
Mathiowitz, Polyanhydride microspheres IV, morphology and characterization systems made by spray drying. J. App. Polymer Sci., 45: 125-134 (1992).
Matsui et al. "Hyperplasia of type II pheumocytes in pulmonary lymphangioleiomyomatosis. Immunohistochemical and electron microscope study." Arch Pathol Lab Med 124:1642, 2000.
Matthews DR et al. "Homeostasis model assessment: insulin resistance and beta-cell function from fasting plasma glucose and insulin concentrations in man." Diabetologia. Jul. 1985;28(7):412-9.
McElduff et al. "Influence of acute upper respiratory tract infection on the absorption of inhaled insulin using the AERx(R) insulin diabetes management system." Br J Clin Pharmacol 59:546, 2005.
McMahon et al., "Effects of basal insulin supplementation on disposition of mixed meal in obese patients with NIDDM", Diabetes, vol. 38, pp. 291-303 (1989).
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.
Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.
Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Mitchell et al. "Intranasal Insulin: PK Profile Designed Specifically for Prandial Treatment of Type 2 Diabetes." Drug Development Research 69(3):143-152 (2008).
Monnier L. et al. "Activation of oxidative stress by acute glucose fluctuations compared with sustained chronic hyperglycemia in patients with type 2 diabetes." JAMA 295:1681, 2006.
Montrose-Rafizadeh et al., Diabetes, 45(Suppl. 2):152A, 1996.
Moren, Aerosols in Medicine (2nd Ed.), Elsevier, pp. 321-350, published 1993.
Mudaliar et al., Insulin Therapy in Type 2 Diabetes. Endocrinology and Metabolism Clinics, vol. 30, No. 4, pp. 1-32 (2001).
Nagai et al., "Powder Dosage Form of Insulin for Nasal Administration", J. Control Ref., 1:15-22 (1984).
Narayan et al. "Impact of recent increase in incidence on future diabetes burden." Diabetes Care 29:2114, 2006.
Naslund et al. "GLP-1 slows solid gastric emptying and inhibits insulin, glucagon, and PYY release in humans." Am J Physiol (Regulatory Integrative Comp Physiol 46):R910, 1999.
Naslund et al. "Prandial subcutaneous injections of glucagon-like petide-1 cause weight loss in obese human subjects." Br J Nutrition 91:439, 2004.
Nathan Dm et a. "Intensive diabetes treatment and cardiovascular disease in patients with Type 1 diabetes." New Eng. J. Med. 353:2643-2653, 2005.
Nathan DM et al. "Management of hyperglycemia in Type 2 diabetes: a consensus algorithm for the initiation and adjustment of therapy." Diabetes Care 29:1963, 2006.
Nathan DM et al. "Management of hyperglycemia in Type 2 diabetes: a consensus algorithm for the initiation and adjustment of therapy." Diabetes Care 31:173, 2008.
Nathan DM et al. "Management of hyperglycemia in Type 2 diabetes: a consensus algorithm for the initiation and adjustment of therapy." Diabetes Care 32:193, 2009.
Nathan, "Initial Management of Glycemia in Type 2 Diabetes Mellitus" N. Eng. J. Med., 2002, 347, 1342-9.
Nauck "Is glucagon-like peptide 1 an incretin hormone?" Diabetologia 42:373, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Nystrom et al. "Effects of glucagon-like peptide-1 on endothelial function in type 2 diabetic patients with stable coronary artery disease." Am J Physiol Endocrinol Metabl 287:E1209, 2004.
Okumura et al., Intratracheal delivery of insulin: absorption from solution and aerosol by rat lung. Int. J. Pharmaceuticals 88: 63-73 (1992).
Oshima et al. "Comparison of half-disappearance times, distribution volumes and metabolic clearance rates of exogenous glucagon-like peptide 1 and glucagon in rats." Regulatory Peptides 21:85, 1988.
Owens et al. "Inhaled human insulin." Nature Reviews, Drug Discovery, vol. 5, No. 5, pp. 371-372, May 2006.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.

(56) References Cited

OTHER PUBLICATIONS

Patton et la., "Inhaled Insulin", Diabetic Medicine, 1997, 14: p. 63-72.
Pearson et al., Systematically Initiating Insulin, supplemental to vol. 32, No. 1, 19S-28S, 2006.
Petkowicz et al., "Hypoglycemic effect of liposome-entrapped insulin adminstered by various routes into normal rats", Pol. J. Pharmacol. Pharm. 41:299-304 (1989).
Pfutzner A et al. "Pulmonary insulin delivery by means of the Technosphere(TM) drug carrier mechanism." Expert Opin Drug Deliv 2:1097-1106, 2005.
Prabhu et al. "A study of factors controlling dissolution kinetic of zinc complexed protein suspensions in various ionic species", Int. J. Pharm. 217(1-2):71-8 (2001).
Pulmonary Delivery: Innovative Technologies breathing new life into inhalable therapeutics, Ondrug Delivery, MannKind, pp. 1-24 (2006).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.
Rachman et al. "Normalization of insulin responses to glucose by overnight infusion of glucagon-like peptide 1 (7-36) amide in patients with NIDDM." Diabetes 45:1524, 1996.
Raskin et al. "Continuous Subcutaneous Insulin Infusion and Multiple Daily Injection Therapy are Equally Effective in Type 2 Diabetes." Diabetes Care, vol. 26, No. 9, pp. 2598-2603, Sep. 2003.
Raufman et al., J. Biol. Chem. 266:2897-902, 1991.
Raufman et al., J. Biol. Chem. 267:21432-37, 1992.
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Rave et al. "Time-action profile of inhaled insulin in comparison with subcutaneously injected insulin lispro and regular human insulin." Diabetes Care 28:1077, 2005.
Razavi et al. "TRPVI+ sensory neurons control beta cell stress and islet inflammation in autoimmune disease." Cell 127:1123, 2006.
Richardson et al. "Technosphere Insulin Technology." Diabetes Technology & Therapeutics, vol. 9, Supplement 1, pp. S-65, 2007.
Richter et al. "Characterization of glucagon-like peptide-1(7-36)amide receptors of rat membranes by covalent cross-linking." FEBS Letters 280:247, 1991.
Pfuetzner, A. et al., "Influence of small dose i.v., s.c. and pulmonary insulin treatment on prandial glucose control in patients with Type 2 diabetes", Program and Abstracts of the Annual Meeting of the European Association for the study of Diabetes, Abstract 812, p. A212, Sep. 9, 2001.
Zisser et al. "In Patients Using Technospere Insulin. Variation in PPG Stayed Within ADA-recommended Targets Despite Large Variations in Glucose Load." Mannkind Corporation, (2010).
International Search Report mailed on Nov. 19, 2014 for International Application No. PCT/US2014/049817 filed on Aug. 5, 2014.
Gonzalez et al., Actualizacion del tratamiento farmacologico de la diabetes mellitus tipo 2. Del Sistema Nacional de Salud. vol. 32, No. 1, pp. 3-16 (2008)—full article in Spanish with English abstract.
Skyler, Pulmonary insulin: current status. Diabetes Voice, vol. 51, Issue I, p. 23-25, 2006.
Wright et al., Inhaled Insulin: Breathing new life into diabetes therapy. Nursing, vol. 37, No. 1, p. 46-48 (2007).

\* cited by examiner

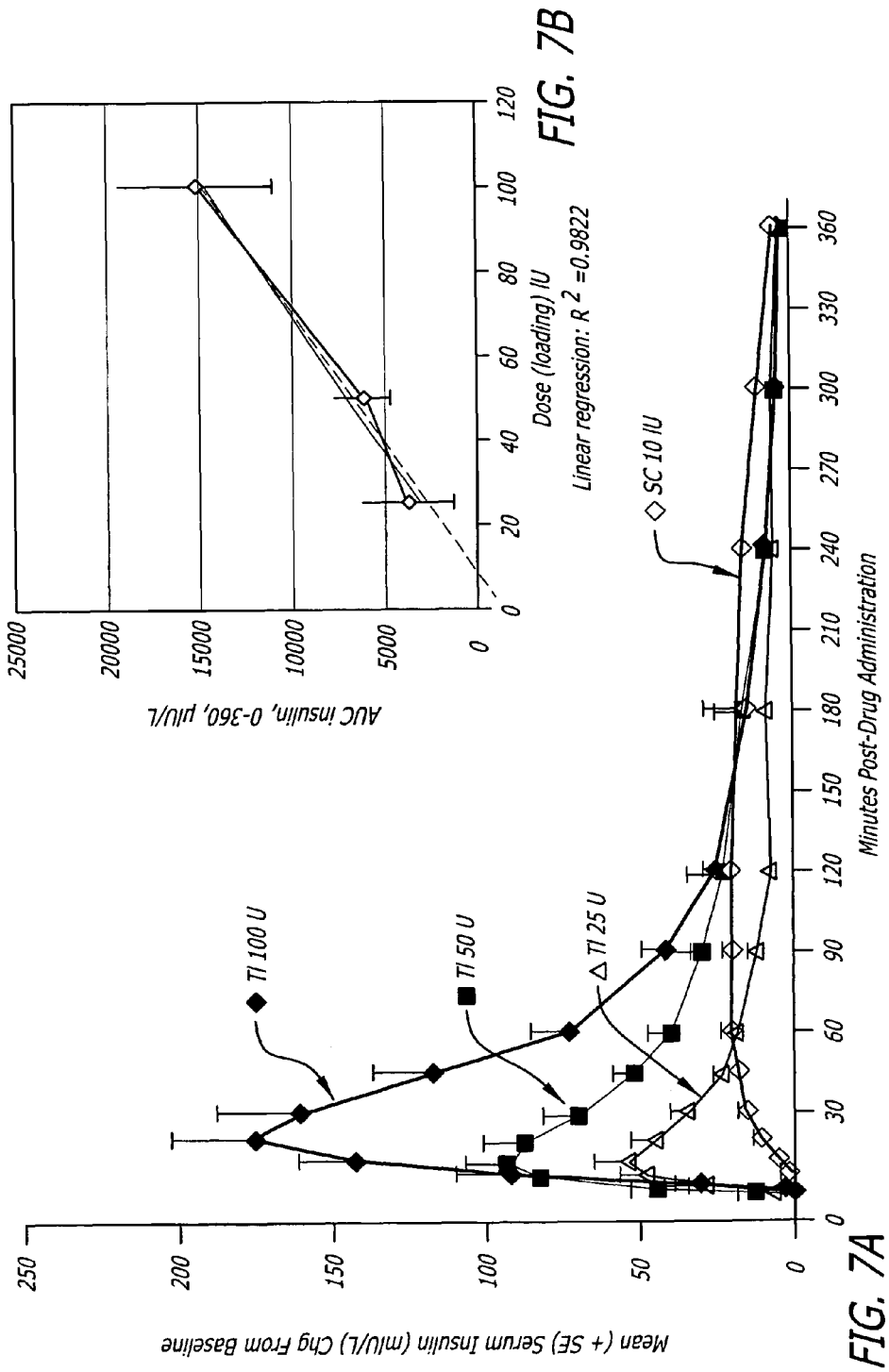

FIG. 20

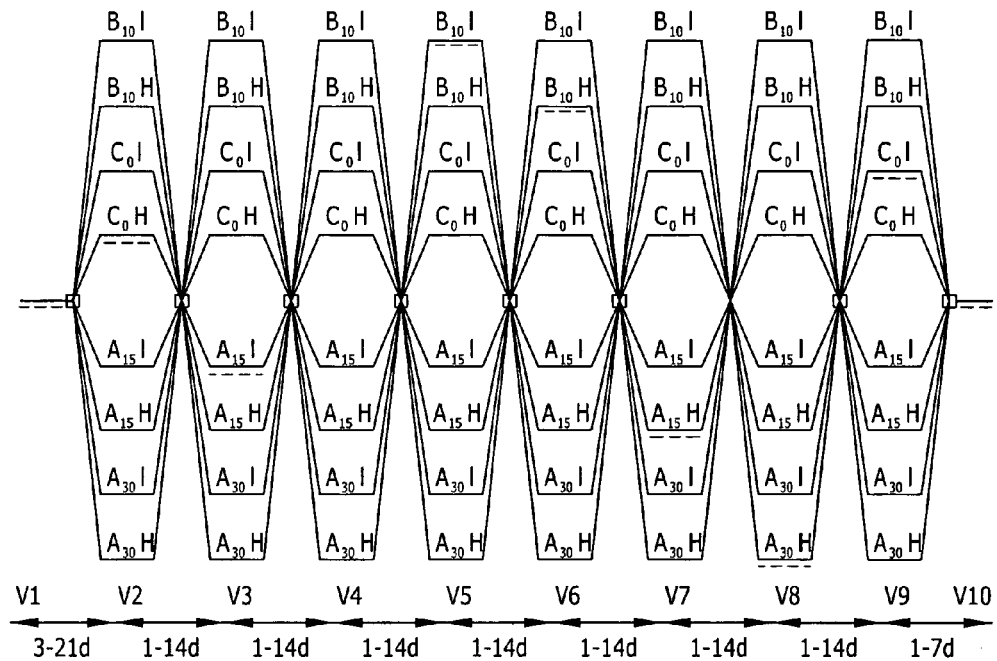

- - - - - example for one patient $B_{10}$ I — Inhalation of Technosphere/Insulin 10 min BEFORE isocaloric meal $B_{10}$ H — Inhalation of Technosphere/Insulin 10 min BEFORE hypercaloric meal $C_0$ I — Inhalation of Technosphere/Insulin DIRECTLY PRIOR TO isocaloric meal $C_0$ H — Inhalation of Technosphere/Insulin DIRECTLY PRIOR TO hypercaloric meal $A_{15}$ I — Inhalation of Technosphere/Insulin 15 min AFTER isocaloric meal $A_{15}$ H — Inhalation of Technosphere/Insulin 15 min AFTER hypercaloric meal $A_{30}$ I — Inhalation of Technosphere/Insulin 30 min AFTER isocaloric meal $A_{30}$ H — Inhalation of Technosphere/Insulin 30 min AFTER hypercaloric meal

POTENTIATION OF GLUCOSE ELIMINATION

CROSS REFERENCE TO RELATED APPLICATIONS

This application claims priority under 35 U.S.C. §119(e) to U.S. Provisional Patent Application No. 60/643,070 filed Jan. 10, 2005 and U.S. Provisional Patent Application No. 60/667,393, filed Mar. 31, 2005 and is a continuation-in-part of U.S. patent application Ser. No. 10/719,734 filed Nov. 21, 2003 which is a continuation of U.S. patent application Ser. No. 10/224,761 filed Aug. 20, 2002, now U.S. Pat. No. 6,652,885, which is a division of U.S. patent application Ser. No. 09/606,468 filed Jun. 29, 2000, now U.S. Pat. No. 6,444,226 which claims priority under 35 U.S.C. §119(e) to U.S. Provisional Patent Application No. 60/141,433 filed Jun. 29, 1999, each of which are incorporated by reference herein in their entirety.

FIELD OF THE INVENTION

The present invention relates to methods of treating diabetes and improving the efficiency of insulin utilization. The method enables effective control of prandial glucose levels while reducing the risk of post-prandial hypoglycemia. In particular the method of the present invention potentiates the activity of endogenous insulin in type 2 diabetics and exogenous long-acting insulin in diabetics requiring basal insulin replacement.

BACKGROUND TO THE INVENTION

Diabetes mellitus currently afflicts at least 200 million people worldwide. Type 1 diabetes accounts for about 10% of this number, and results from autoimmune destruction of insulin-secreting β-cells in the pancreatic islets of Langerhans. Survival depends on multiple daily insulin injections. Type 2 diabetes accounts for the remaining 90% of individuals affected, and the rate of prevalence is increasing. Type 2 diabetes is often, but not always, associated with obesity, and although previously termed late-onset or adult diabetes, is now increasingly manifest in younger individuals. It is caused by a combination of insulin resistance and inadequate insulin secretion.

In a non-stressed normal individual, the basal glucose level will tend to remain the same from day to day because of an intrinsic feedback loop. Any tendency for the plasma glucose concentration to increase is counterbalanced by an increase in insulin secretion and a suppression of glucagon secretion, which regulate hepatic glucose production (gluconeogenesis and release from glycogen stores) and tissue glucose uptake to keep the plasma glucose concentration constant. If the individual gains weight or becomes insulin resistant for any other reason, blood glucose levels will increase, resulting in increased insulin secretion to compensate for the insulin resistance. Therefore the glucose and insulin levels are modulated to minimize changes in these concentrations while relatively normal production and utilization of glucose are maintained.

In this normal individual, a meal induces the secretion of a burst of insulin, generating a rapid spike in serum insulin concentration that then decays relatively quickly (see FIG. 1). This is referred to as first-phase kinetics and is responsible for the shut-off of release of glucose from the liver. Homeostatic mechanisms then match insulin secretion (and serum insulin levels) to the glucose load. This is observed as a slow decay of modestly elevated serum insulin levels back to baseline and is referred to as second-phase kinetics.

Type 2 diabetics typically exhibit a delayed response to increases in blood glucose levels. While normal individuals usually release insulin within 2-3 minutes following the consumption of food, type 2 diabetics may not secrete endogenous insulin until blood glucose begins to rise, and then with second-phase kinetics, that is a slow rise to an extended plateau in concentration. As a result, endogenous glucose production continues after consumption and the patient experiences hyperglycemia due to elevated blood glucose levels.

Loss of eating-induced insulin secretion is one of the earliest disturbances of β-cell function. While genetic factors play an important role, some insulin secretory disturbances seem to be acquired and may be at least partly reversible through optimal glucose control. Optimal glucose control via insulin therapy after a meal can lead to a significant improvement in natural glucose-induced insulin release by requiring both normal tissue responsiveness to administered insulin and an abrupt increase in serum insulin concentrations. Therefore, the challenge presented in treatment of early stage type 2 diabetics, those who do not have excessive loss of β-cell function, is to restore the rapid release of insulin following meals.

In addition to the loss of first-phase kinetics, early stage type 2 diabetics do not shut-off glucose release after a meal. As the disease progresses, the demands placed on the pancreas further degrades its ability to produce insulin and control of blood glucose levels gradually deteriorates. If unchecked, the disease can progress to the point that the deficit in insulin production approaches that typical of fully developed type 1 diabetes. Type 1 diabetes can involve an early "honeymoon" stage, following an initial crisis, in which insulin is still produced but defects in release similar to early type 2 disease are exhibited.

Most early stage type 2 diabetics currently are treated with oral agents, but with limited success. Subcutaneous injections are also rarely effective in providing insulin to type 2 diabetics and may actually worsen insulin action because of delayed, variable and shallow onset of action. It has been shown, however, that if insulin is administered intravenously with a meal, early stage type 2 diabetics experience the shut-down of hepatic glucose release and exhibit increased physiologic glucose control. In addition their free fatty acids levels fall at a faster rate that without insulin therapy. While possibly effective in treating type 2 diabetes, intravenous administration of insulin, is not a reasonable solution, as it is not safe or feasible for patients to intravenously administer insulin at every meal.

Significant pathology (and morbidity) in diabetics is associated with inadequate control of blood glucose. Excursions of blood glucose concentration both above and below the desired, normal range are problematic. In treatments that fail to mimic physiologic insulin release, the rise in insulin concentration does not produce sufficiently high glucose elimination rates to completely respond to the glucose load resulting from a meal. This can be further exacerbated by failure to shut off glucose release from the liver. Additionally, with many forms of insulin therapy, serum insulin levels and glucose elimination rates also remain elevated after the prandial glucose load has abated, threatening hypoglycemia. Attempts to better control peak glucose loads by increasing insulin dose further increase this danger.

Current insulin therapy modalities can supplement or replace endogenously-produced insulin to provide basal and second-phase-like profiles but do not mimic first-phase kinetics (see FIG. 2). Additionally, conventional insulin therapy often involves only one or two daily injections of insulin. However, more intensive therapy such as three or more administrations a day, providing better control of blood glucose levels, are clearly beneficial (see for example Nathan, D. M., et al., *N Engl J Med* 353:2643-53, 2005), but many patients are reluctant to accept the additional injections.

Until recently, subcutaneous (SC) injection has been the only route of delivering insulin to patients with both type 1 and type 2 diabetes. However, SC insulin administration does not lead to optimal pharmacodynamics for the administered insulin. Absorption into the blood (even with rapid acting insulin analogues) does not mimic the prandial physiologic insulin secretion pattern of a rapid spike in serum insulin concentration. Since the discovery of insulin, alternative routes of administration have been investigated for their feasibility in improving the pharmacodynamics of the administered insulin and improving compliance by reducing the discomfort associated with sc injections.

The alternative routes of insulin administration which have been evaluated in detail include the dermal, oral, buccal, nasal and pulmonary routes. Dermal insulin application does not result in reproducible and sufficient transfer of insulin across the highly efficient skin barrier. Oral insulin has not yet been achieved, primarily due to digestion of the protein and lack of a specific peptide carrier system in the gut. Nasal insulin application leads to a more rapid absorption of insulin across the nasal mucosa, however not with first-phase kinetics. The relative bioavailability of nasal administered insulin is low and there is a high rate of side effects and treatment failures. Buccally absorbed insulin also fails to mimic a first-phase release (Raz, I. et al., Fourth Annual Diabetes Meeting, Philadelphia, Pa., 2004).

Recently, pulmonary application of insulin has become a viable insulin delivery system. Some pulmonary insulin formulations in development provide faster appearance of insulin in the blood than typical subcutaneously delivered products (see FIG. 3), but apparently do not adequately reproduce all aspects of first-phase kinetics.

Therefore, a need exists for an insulin formulation which can mimic first-phase kinetics to provide physiologic post-prandial insulin pharmacokinetics and pharmacodynamics for maintenance of normal physiologic blood glucose levels.

SUMMARY OF THE INVENTION

The present invention provides methods of treating diabetes and improving the efficiency of insulin utilization. The method enables effective control of prandial glucose levels while reducing the risk of post-prandial hypoglycemia. In particular the method of the present invention improves the potentiation of exogenous prandial insulin as well as potentiating the activity of endogenous insulin in type 2 diabetics and exogenous long-acting insulin in diabetics requiring basal insulin replacement.

In one embodiment of the present invention, a method of improving potentiation of the glucose elimination rate of the present invention is provided comprising producing a first-phase insulin-like spike in serum insulin levels with an exogenously-administered insulin composition, wherein the exogenously-administered insulin composition is not administered intravenously.

In another embodiment of the method of improving potentiation of the glucose elimination rate of the present invention, the exogenously administered insulin composition is administered in proximity to a meal. In yet another embodiment the exogenously administered insulin composition is administered from approximately 10 minutes prior to a meal to approximately 30 minutes after a meal.

In yet another embodiment of the method of improving potentiation of the glucose elimination rate of the present invention, the insulin-related disorder is diabetes mellitus, such as type 1 or type 2 diabetes mellitus.

In an embodiment of the method of improving potentiation of the glucose elimination rate of the present invention, the first-phase-like spike in serum insulin concentration is greater than about 75 mU/L, greater than about 100 mU/L or greater than about 125 mU/L In another embodiment of the method of improving potentiation of the glucose elimination rate of the present invention, the first-phase-like spike in serum insulin concentration is achieved within about 20 minutes, within about 15 minutes or within about 10 minutes.

In another embodiment of the method of improving potentiation of the glucose elimination rate of the present invention, the potentiation comprises the glucose elimination rate reaching maximum within about 1 hour. In yet another embodiment the potentiation comprises the glucose elimination rate reaching maximum within about 45 minutes.

In an embodiment of the method of improving potentiation of the glucose elimination rate of the present invention, the glucose elimination rate continues to rise after serum insulin concentration begins to fall.

In another embodiment of the method of improving potentiation of the glucose elimination rate of the present invention, the glucose elimination rate begins to fall by about 1 hour after insulin administration.

In yet another embodiment of the method of improving potentiation of the glucose elimination rate of the present invention, the glucose elimination rate returns to baseline by about 6 hours.

In another embodiment of the method of improving potentiation of the glucose elimination rate of the present invention, the exogenously-administered insulin composition comprises a complex between a diketopiperazine and human insulin. In yet another embodiment the diketopiperazine is fumaryl diketopiperazine.

In an embodiment of the method of improving potentiation of the glucose elimination rate of the present invention, the exogenously-administered insulin composition is inhaled.

In an embodiment of the present invention, a method of mimicking first-phase human beta cell insulin release is provided comprising administering an exogenously-administered insulin composition.

In another embodiment of the method of mimicking first-phase human beta cell insulin release of the present invention, the exogenously-administered insulin composition comprises a complex between a diketopiperazine and human insulin. In another embodiment, the diketopiperazine is fumaryl diketopiperazine. In yet another embodiment, the exogenously-administered insulin composition is inhaled.

In one embodiment of the present invention, a method of treating an insulin-related disorder is provided comprising administering to a patient having an insulin-related disorder an exogenously-administered composition such that the exogenously-administered insulin composition mimics first-phase insulin kinetics, and wherein the exogenously-administered insulin composition is not administered intravenously.

In another embodiment of the method of treating an insulin-related disorder of the present invention, the exogenously-administered insulin composition comprises a complex between a diketopiperazine and human insulin. In another embodiment, the diketopiperazine is fumaryl diketopiperazine. In yet another embodiment, the exogenously-administered insulin composition is inhaled.

In yet another embodiment of the method of treating an insulin-related disorder of the present invention, the insulin-related disorder is diabetes mellitus, such as type 1 or type 2 diabetes mellitus.

In one embodiment of the present invention, a method of maintaining blood glucose levels in a patient with an insulin-related disorder in a normal range is provided comprising providing an exogenously-administered insulin composition wherein first-phase insulin pharmacokinetics are obtained within about 30 minutes of administration, alternatively within about 15 minutes of administration and wherein the exogenously-administered insulin composition is not administered intravenously.

In another embodiment of the method of maintaining blood glucose levels of the present invention, the exogenously-administered insulin composition comprises a complex between a diketopiperazine and human insulin. In another embodiment, the diketopiperazine is fumaryl diketopiperazine.

In another embodiment of the method of maintaining blood glucose levels of the present invention, the exogenously administered insulin composition is a non-naturally occurring form of insulin.

In one embodiment of the present invention, a method of restoring normal insulin kinetics in a patient in need thereof is provided comprising administering to a patient having an insulin-related disorder an inhaled insulin composition such that the inhaled insulin composition mimics first-phase insulin kinetics. In another embodiment, the insulin-related disorder is diabetes mellitus. In yet another embodiment, the method further comprises administering a long-acting basal insulin.

BRIEF DESCRIPTION OF THE DRAWINGS

FIGS. 7A-B depict the mean serum insulin concentration (FIG. 7A) and insulin absorption, as AUC (FIG. 7B), in individuals with type 2 diabetes mellitus at different dose levels of Technosphere®/Insulin (TI) and SC insulin according to the teachings of the present invention.

FIG. 20 depicts the study schema for the clinical trial disclosed in Example 6.

DEFINITION OF TERMS

Figure 1:
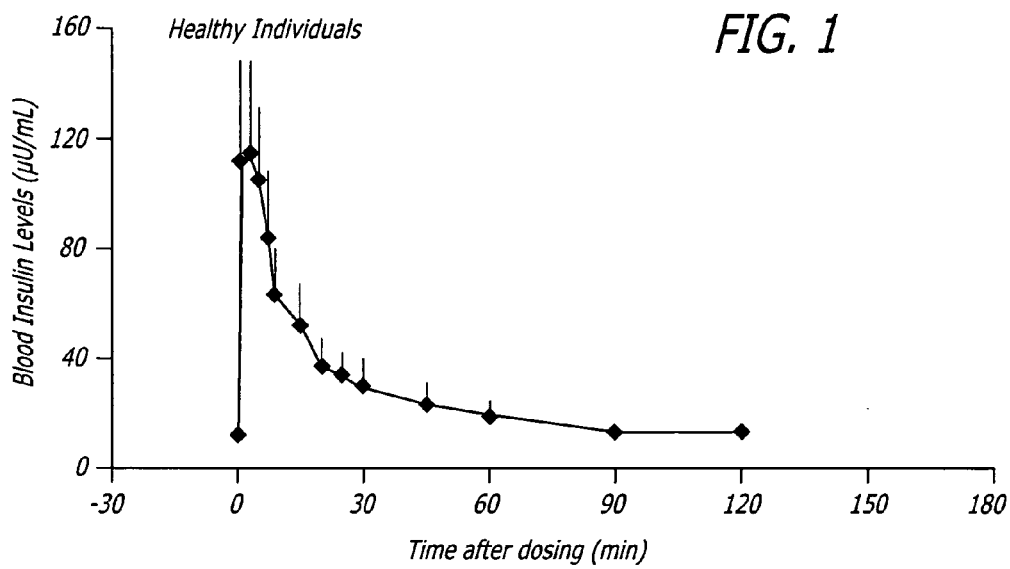
FIG. 1 depicts the measurement of first-phase insulin release kinetics following artificial stimulation by bolus glucose infusion.

Prior to setting forth the invention, it may be helpful to provide an understanding of certain terms that will be used hereinafter:

Dry powder: As used herein "dry powder" refers to a fine particulate composition that is not suspended or dissolved in a propellant, carrier, or other liquid. It is not meant to imply a complete absence of all water molecules.

Excursion: As used herein, "excursion" refers to blood glucose concentrations that fall either above or below a pre-meal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating.

First-Phase: As used herein, "first-phase" refers to a burst of insulin release from the pancreas induced as a result of a meal. A first-phase insulin release generates a spike in blood insulin concentration that is a rapid peak which then decays relatively quickly.

Glucose Elimination Rate: As used herein, "glucose elimination rate" is the rate at which glucose disappears from the blood and is determine by the amount of glucose infusion required to maintain stable blood glucose, often around 120 mg/dL during the study period. This glucose elimination rate is equal to the glucose infusion rate, abbreviated as GIR.

Hyperglycemia: As used herein, "hyperglycemia" is a higher than normal fasting blood glucose concentration, usually 126 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 60 mg/dL, but in some instances less than 3.5 mM (63 mg/dL).

Insulin Composition: As used herein, "insulin composition" refers to any form of insulin suitably for administration to a mammal and includes insulin isolated from mammals, recombinant insulin, insulin associated with other molecules and also includes insulin administered by any route including, pulmonary, subcutaneous, nasal, oral, buccal and sublingual. Insulin compositions can be formulated as dry powders or aqueous solutions for inhalation; aqueous solutions for subcutaneous, sublingual, buccal, nasal or oral administration and solid dosage forms for oral and sublingual administration.

Insulin-Related Disorder: As used herein, "insulin-related disorders" refers to disorders involving production, regulation, metabolism, and action of insulin in a mammal. Insulin related disorders include, but are not limited to, type 1 diabetes mellitus, type 2 diabetes mellitus, hypoglycemia, hyperglycemia, insulin resistance, loss of pancreatic beta cell function and loss of pancreatic beta cells.

Periprandial: As used herein, "periprandial" refers to a period of time starting shortly before and ending shortly after the ingestion of a meal or snack.

Postprandial: As used herein, "postprandial" refers to a period of time after ingestion of a meal or snack.

Potentiation: Generally, potentiation refers to a condition or action that increases the effectiveness or activity of some agent over the level that the agent would otherwise attain. Similarly it may refer directly to the increased effect or activity. As used herein, "potentiation" particularly refers to the ability of elevated blood insulin concentrations to boost effectiveness of subsequent insulin levels to, for example, raise the glucose elimination rate.

Prandial: As used herein, "prandial" refers to a meal or a snack.

Second-Phase: As used herein, "second-phase" refers to the slow decay of modestly elevated blood insulin levels back to baseline after the first-phase has passed. Second-phase can also refer to the non-spiking release of insulin in response to elevated blood glucose levels.

Technosphere®/Insulin: As used herein, "Technosphere®/Insulin" refers to an insulin composition comprising regular human insulin and Technosphere® microparticles, a drug delivery system. Technosphere® microparticles comprise a diketopiperazine. Specifically, Technosphere®/Insulin comprises a fumaryl diketopiperazine/human insulin composition.

Technosphere®/Placebo: As used herein, "Technosphere®/Placebo" refers to Technosphere® particles which are not associated with insulin.

Units of measure: Subcutaneous and intravenous insulin dosages are expressed in IU which is defined by a standardized biologic measurement. Amounts of insulin formulated with fumaryl diketdpiperazine (FDKP) are also reported in IU as are measurements of insulin in the blood. Technosphere®/Insulin dosages are expressed in arbitrary units (U) which are numerically equivalent to the amount of insulin formulated in the dosage.

DETAILED DESCRIPTION OF THE INVENTION

A common problem in the use of insulin therapy in the treatment of diabetes is that doses sufficient to control prandial glucose loads produce elevated glucose elimination rates for extended intervals that can persist after the meal, leading to post prandial hypoglycemia. It is now disclosed that a short sharp rise to peak serum insulin concentration (which then declines) results in an accelerated approach to maximal glucose elimination rates. This has the effect of compressing the bulk of the effect of the administered insulin to the periprandial time interval reducing the risks of post-prandial hypoglycemia. The field has generally assumed that the rate of glucose elimination at any point in time is a function of insulin concentration at that point in time. In point of fact the glucose elimination rate achieved by any particular insulin concentration is influenced by prior insulin concentration. Thus glucose elimination rate is potentiated by previous high insulin levels such that, for any particular insulin concentration, the glucose elimination rate is greater when the subject has experienced a high insulin concentration in a preceding time interval. The present inventors have now surprisingly discovered that this potentiation drives the glucose elimination rate to maximum much more quickly in response to a large and rapid peak in insulin concentration than when peak insulin concentration is approached more gradually.

Figure 2:
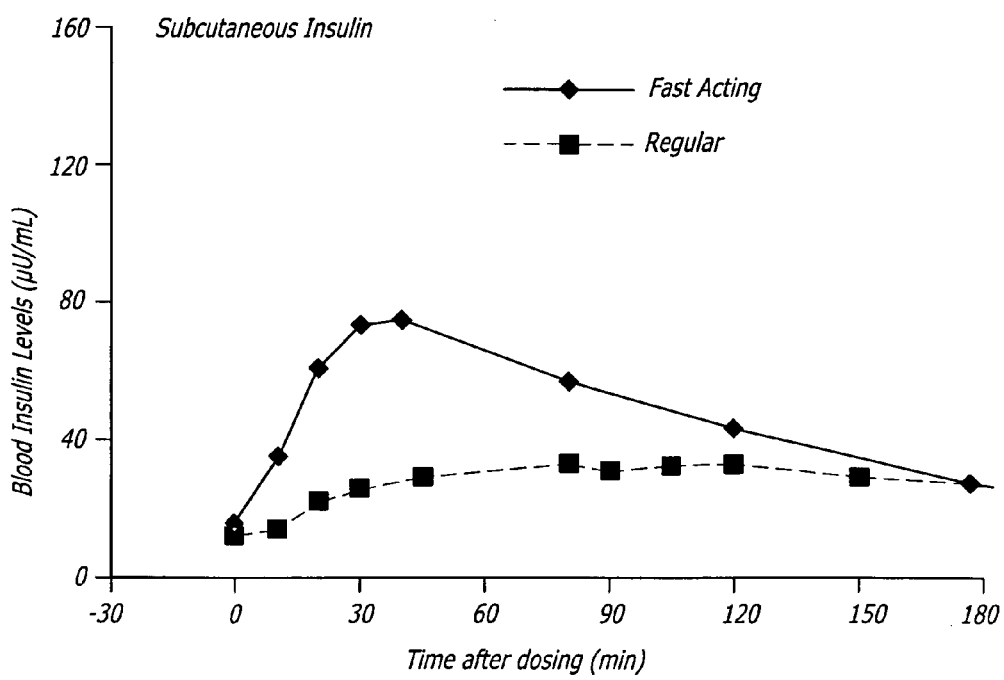
FIG. 2 depicts serum insulin concentration after administration of subcutaneous (SC) regular human insulin or sc fast acting insulin (Novolog™). Novolog™ is a registered trademark of Novo Nordisk Pharmaceuticals, Bagsvaerd, Denmark.
Figure 3:
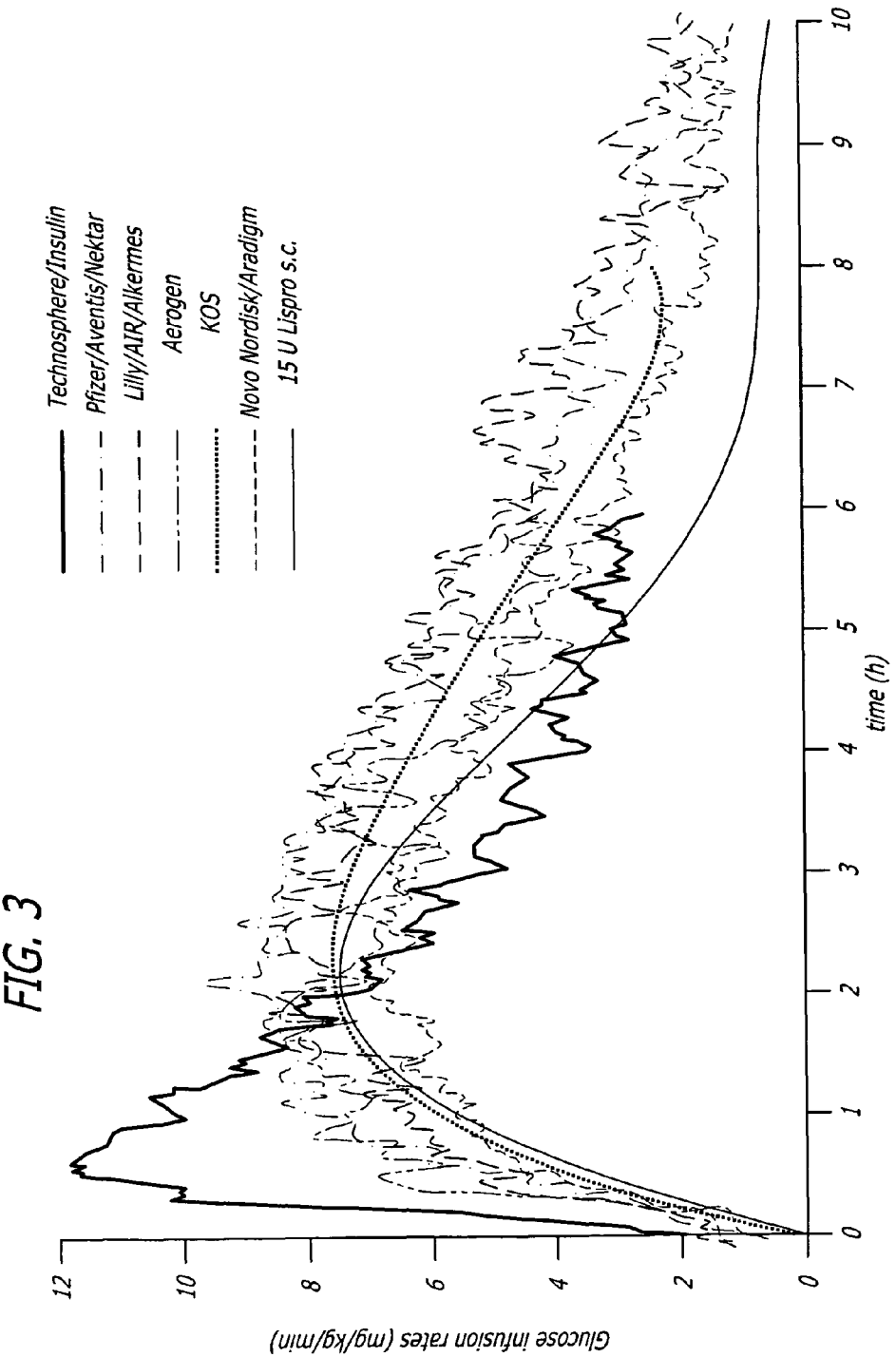
FIG. 3 depicts a composite of time-action profiles of a variety of forms of inhaled (MannKind, Pfizer/Aventis/Nektar, Alkermes, Aerogen, KOS, Novo Nordisk/Aradigm) and injected (Lispro sc) insulin from different manufacturers (from: *Br J Diab Vasc. Dis* 4:295-301, 2004).
Figure 4:
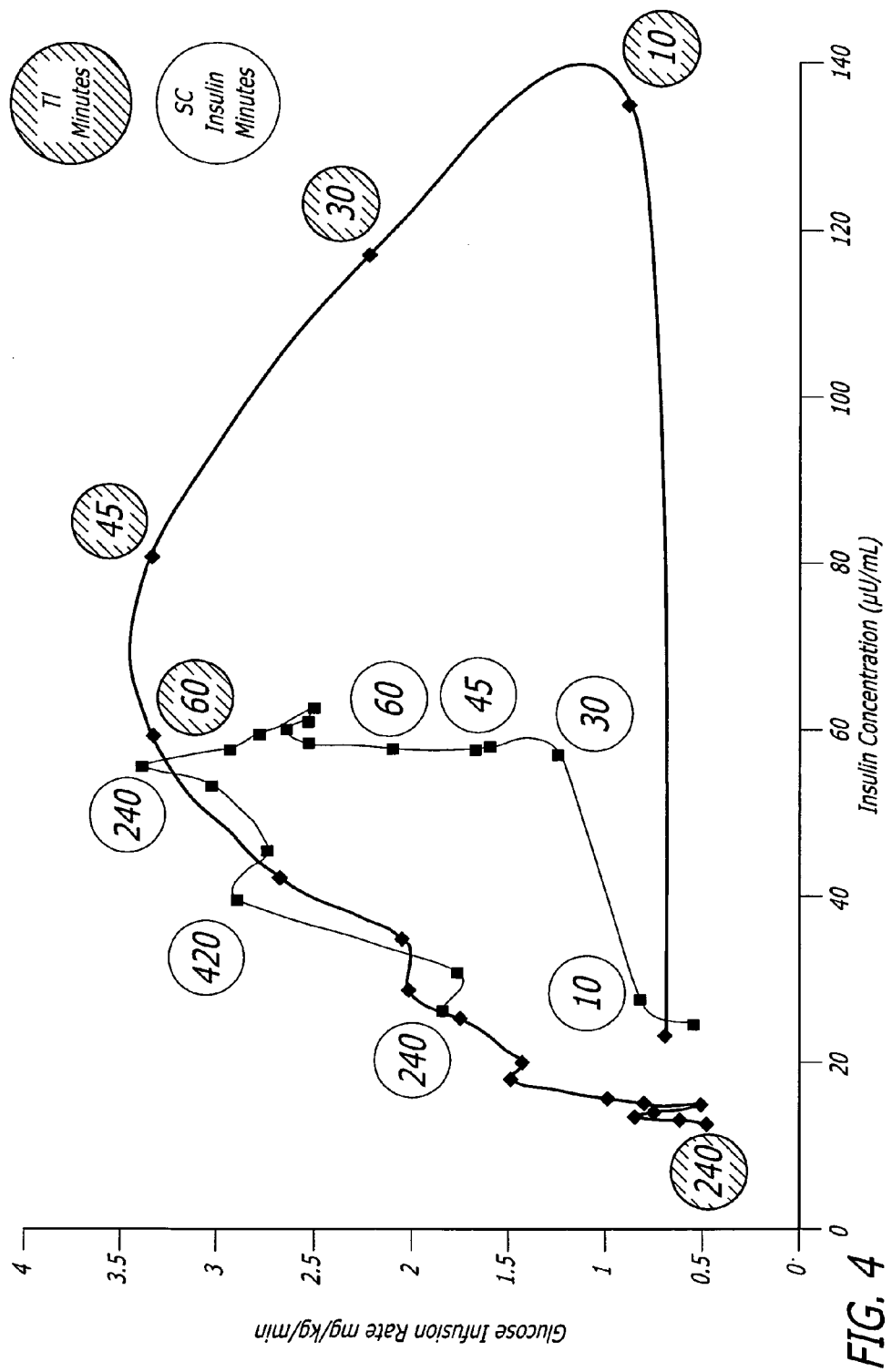
FIG. 4 depicts the relationship over time between serum insulin concentration and glucose elimination rate, as glucose infusion rate (GIR) under a glucose clamp, for a fast-acting subcutaneously administered insulin (SC) and a pulmonary dry powder insulin formulated with fumaryl diketopiperazine (Technosphere®/Insulin, TI) according to the teachings of the present invention.
Figure 5:
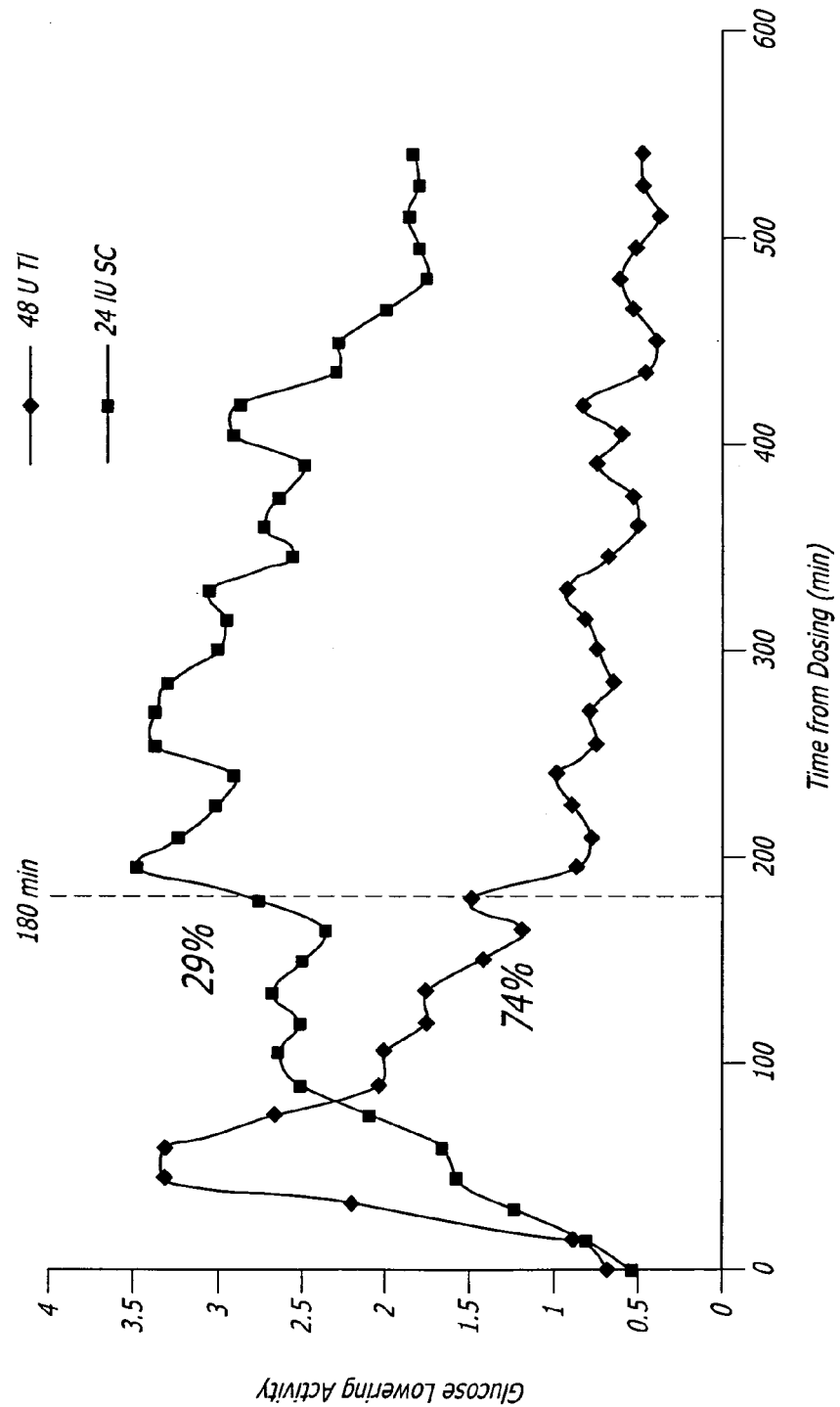
FIG. 5 depicts increased postprandial glucose elimination for Technosphere®/Insulin (48 U TI) versus a fast-acting subcutaneously administered insulin (24 IU SC) in individuals with type 2 diabetes according to the teachings of the present invention.

With a typical fast-acting subcutaneously (SC) administered insulin, maximal insulin concentrations can be achieved in about 30 to 45 minutes and remain at this plateau for several hours (FIG. 2). The glucose elimination rate (measured as the glucose infusion rate [GIR]) however continues to rise throughout this plateau phase (FIG. 5), peaking only as insulin concentration begins to decay (FIG. 4). In contrast, with an administration that mimics a physiological first-phase insulin release, insulin concentration peaks at a much higher level and begins to fall by about 15 minutes (FIG. 1). The GIR, however, continues to rise after the peak in insulin concentration but reaches its maximum in less than an hour and then falls in concert with insulin concentration (FIG. 4). By three hours, the bulk of glucose elimination to be accomplished by this insulin has occurred, yet the subcutaneous insulin has exerted less than a third of its effect (FIG. 5).

By taking advantage of the potentiating effects of a rapid spike in insulin concentration, an insulin therapy methodology that mimics first-phase kinetics can offer several advantages. Such insulin formulations are generally administered within a few minutes of commencing a meal, unlike more slowly absorbed insulins which are usually taken at defined period before a meal. The interval is generally based on the time needed to achieve maximal insulin concentration on the tacit assumption that glucose elimination rate is a function of insulin concentration. However, since glucose elimination rate continues to increase throughout the plateau in insulin concentration, doses large enough to keep glucose levels from exceeding the normal range pose a risk that the resultant high glucose elimination rate hours after the meal will lead to hypoglycemia. Due to the potentiating effect of an insulin preparation causing a rapid peak in serum insulin concentration, it can be more readily coordinated with a meal. The quick acquisition of maximal glucose elimination rate is well suited to mealtime administration, or even up to an hour after commencing a meal. The second-phase decay in insulin concentration reduces the risk of inducing hypoglycemia hours after the meal. Further advantages are realized in diabetics who retain some ability to produce insulin in that their endogenous second-phase and basal insulin will also be potentiated, increasing the effectiveness of that limited insulin and reducing pancreatic stress. Methods of reducing pancreatic stress with the exogenously-administered insulin compositions of the present invention are disclosed in co-pending U.S. Provisional Patent Application No. 60/704,295 entitled "Methods of Preserving the Function of Insulin-Producing Cells in Diabetes," which is incorporated by reference herein for all it teaches regarding methods of reducing pancreatic stress by administering diketopiperazine/insulin compositions. The administration of exogenous insulin also suppresses insulin secretion from the pancreas. The quicker return to baseline achieved with a rapidly peaking insulin allows for earlier reassertion of pancreatic secretion and re-establishment of homeostatic control of blood glucose levels, further reducing the risk of post-treatment hypoglycemia. Similar advantages are contemplated from combined treatment with rapid-peaking and long acting exogenous insulin for diabetics who do not produce significant levels of insulin.

As used herein, mimicking physiologic mealtime first-phase insulin release (or pharmacokinetics) does not necessarily indicate exact replication of all features of the physiologic response. It can refer to methodologies producing a spike or peak of insulin concentration in the blood that constitutes both a relatively quick rise (less than about 15 minutes from administration or first departure from baseline) and fall (descent through half maximal by 80 minutes, preferably 50 minutes, more preferably 35 minutes after peak) in concentration. This is in contrast to methods producing a more gradual rise (from over 20 minutes to several hours) to the maximal insulin concentration achieved and a prolonged plateau at near maximal concentrations. It can also refer to methodologies in which the spike in insulin concentration can be reliably coordinated with the start of a meal. It can also refer to methodologies achieving maximal glucose elimination rate within about 30-90 minutes, preferably around 45-60 minutes, after administration. A methodology that mimics first-phase release is generally also one that can be practiced by diabetics upon themselves without special medical training, such as training in intravenous injection. Special medical training would not include training to use medical devices, such as dry powder inhalers, that are routinely used by persons who are not medical professionals. As used herein, "meal", "meals", and/or "mealtime", etc. include traditional meals and meal times; however, these also include the ingestion of any sustenance regardless of size and/or timing.

Superior blood glucose control can be appreciated as reduced exposure to (elevated) glucose concentrations ($AUC_{GLU}$), reduced levels of HbA1c (glycosylated hemoglobin), lessened potential or incidence of hypoglycemia, reduced variability of response to treatment, and the like. Glycosylated hemoglobin levels correlate with the overall blood glucose control over the past three months. Generally one compares outcomes of different procedures at similar levels of exposure to insulin ($AUC_{INS}$) for various time intervals. Glucose exposure and risk of hypoglycemia ultimately depends on how well glucose elimination rate matches glucose load over time. This in turn will generally depend on the shape of the insulin concentration curve rather than simply on the area under the curve. The rapid rise and fall of insulin concentration typical of physiologic first-phase response is well suited to matching glucose elimination rate to prandial glucose load.

The desirable first phase kinetics can be obtained through the pulmonary administration of a dry powder insulin formulation containing insulin complexed to 3,6-di(fumaryl-4-aminobutyl)-2,5-diketop iperazine (hereinafter fumaryl diketopiperazine or FDKP). The use of diketopiperazines for drug delivery is known in the art (see for example U.S. Pat. No. 5,352,461 entitled "Self Assembling Diketopiperazine Drug Delivery System; U.S. Pat. No. 5,503,852 entitled Method for Making Self-Assembling Diketopiperazine Drug Delivery System; U.S. Pat. No. 6,071,497 entitled Microparticles for Lung Delivery Comprising Diketopiperazine; and U.S. Pat. No. 6,331,318 entitled Carbon-Substituted Diketopiperazine Delivery System, each of which is incorporated herein by reference for all that it teaches regarding diketopiperazines and diketopiperazine-mediated drug delivery). Pulmonary drug delivery using diketopiperazine and other microparticles is disclosed in U.S. Pat. No. 6,428,771 entitled "Method for Drug Delivery to the Pulmonary System," which is hereby incorporated by reference for all that it teaches regarding delivery of diketopiperazine-based compositions to the pulmonary system. Complexes of insulin and FDKP, their formation, properties, and use are disclosed in U.S. Pat. Nos.

6,444,226 and 6,652,885 both entitled "Purification and Stabilization of Peptide and Protein Pharmaceutical Agents," each of which is incorporated herein by reference for all that they teach regarding formation and administration of FDKP-complexed agents. Additional methods of manufacture of complexes of diketopiperazines and insulin are disclosed in co-pending U.S. Provisional Patent Application No. 60/717,524 entitled "Method of Drug Formulation Based on Increasing the Affinity of Active Agents for Crystalline Microparticle Surfaces," which is incorporated herein by reference for all it teaches regarding manufacture of complexes of diketopiperazines and insulin. Particularly advantageous devices for delivery of the powder are disclosed in U.S. patent application Ser. No. 10/655,153 entitled "Unit Dose Cartridge and Dry Powder Inhaler" and in U.S. Pat. No. 6,923,175 entitled "Inhalation Apparatus", each of which is incorporated herein by reference for all that they teach regarding pulmonary delivery of insulin compositions.

Complexation of large polymers, such as proteins and peptides in diketopiperazines can be used to remove impurities or contaminants such as metal ions or other small molecules. The diketopiperazines also serve both to stabilize and enhance delivery of the complexed materials. Formulations also have been developed facilitate transport of active agents across biological membranes. These formulations include microparticles formed of (i) the active agent, which may be charged or neutral, and (ii) a transport facilitator that masks the charge of the agent and/or that forms hydrogen bonds with the membrane. The formulations can provide rapid increases in the concentration of active agent in the blood following administration of the formulations.

Technosphere® refers to a diketopiperazine-based drug delivery system which can complex and stabilize peptides in small particles. Diketopiperazines, particularly fumaryl diketopiperazine (FDKP), self-assemble into microparticles with a mean diameter of about 2 microns. In the process it can entrap or complex with peptides, such as insulin, present in the solution during or after self-assembly. Once dried, these microparticles become a suitable composition for pulmonary delivery to the systemic circulation. When administered by the pulmonary route, Technosphere® particles dissolve in the pH neutral environment of the deep lung and facilitate the rapid and efficient absorption of the peptide into systemic circulation. The FDKP molecules are excreted un-metabolized in the urine within hours of administration.

Additionally, salts of diketopiperazines can be used in the compositions of the present invention as disclosed in co-pending U.S. patent application Ser. No. 11/210,710 entitled "Diketopiperazine Salts for Drug Delivery and Related Methods" which is incorporated by reference herein for all it teaches regarding diketopiperazine salts and their use to in pulmonary delivery of insulin.

Insulin, a polypeptide with a nominal molecular weight of 6,000 daltons, traditionally has been produced by processing pig and cow pancreas to isolate the natural product. More recently, however, recombinant technology has been used to produce human insulin in vitro. Natural and recombinant human insulin in aqueous solution is in a hexameric conformation, that is, six molecules of recombinant insulin are noncovalently associated in a hexameric complex when dissolved in water in the presence of zinc ions. Hexameric insulin is not rapidly absorbed. In order for recombinant human insulin to be absorbed into a patient's circulation, the hexameric form must first disassociate into dimeric and/or monomeric forms before the material can move into the bloodstream.

For example, it was discovered that hexameric insulin can be delivered to the lung in fumaryl diketopiperazine formulation, reaching peak blood concentrations within 3-10 minutes. In contrast, insulin administered by the pulmonary route without fumaryl diketopiperazine typically takes between 25-60 minutes to reach peak blood concentrations, while hexameric insulin takes 30-90 minutes to reach peak blood level when administered by subcutaneous injection. This feat has been successfully replicated several times and in several species, including humans.

Removing zinc from insulin typically produces unstable insulin with an undesirably short shelf life. Purification to remove zinc, stabilization and enhanced delivery of insulin is demonstrated by the examples. Formulations of insulin complexed with fumaryl diketopiperazine were found to be stable and have an acceptable shelf life. Measurement of the zinc levels demonstrated that the zinc had been largely removed during the complexation process, yielding monomeric insulin in a stable delivery formulation.

The insulin compositions of the present invention can be administered to patients in need of insulin therapy. The compositions preferably are administered in the form of microparticles, which can be in a dry powder form for pulmonary administration or suspended in an appropriate pharmaceutical carrier, such as saline.

The microparticles preferably are stored in dry or lyophilized form until immediately before administration. The microparticles then can be administered directly as a dry powder, such as by inhalation using, for example, dry powder inhalers known in the art. Alternatively, the microparticles can be suspended in a sufficient volume of pharmaceutical carrier, for example, as an aqueous solution for administration as an aerosol. The microparticles also can be administered via oral, subcutaneous, and intravenous routes.

The insulin compositions can be administered to any targeted biological membrane, preferably a mucosal membrane of a patient. In one embodiment, the patient is a human suffering from an insulin-related disorder such as diabetes mellitus. In another embodiment, the composition delivers insulin in biologically active form to the patient, which provides a spike of serum insulin concentration which simulates the normal response to eating.

EXAMPLES

Example 1

Insulin Concentration at Different Dose Levels Indicates Linear Absorption

Various dosages of Technosphere®/Insulin (TI, MannKind Corporation) were administered to human subjects and insulin concentration in the blood was measured (FIG. 7A). Insulin absorption, as AUC, was linear with dosage at least up to 100 U TI (FIG. 7B).

Example 2

Mimicry of the Early Phase Insulin Response in Humans with Rapidly Bioavailable Inhaled Insulin Accelerates Post Prandial Glucose Disposal Compared to Insulin with Slower Bioavailability The relationship between time, insulin concentration and glucose elimination rate in a group of 12 subjects with type 2 diabetes, during an isoglycemic insulin clamp was studied. Each subject received 24 IU subcutaneous insulin (Actrapid®, Novo Nordisk) or 48 U Technosphere®/Insulin on separate study days in a cross-over design.

Figure 8:
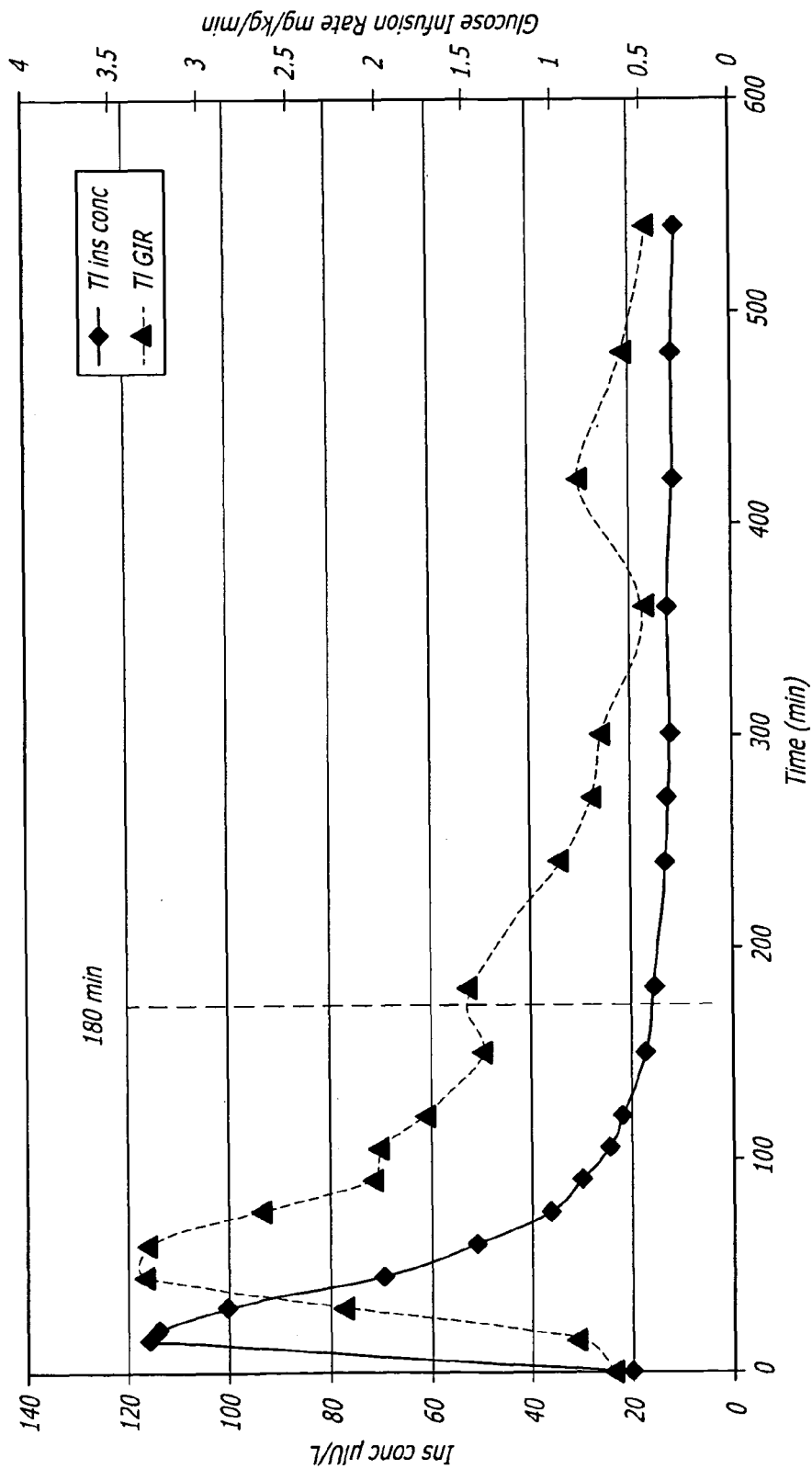
FIG. 8 depicts a comparison of insulin concentration and glucose elimination rate over time in individuals with type 2 diabetes mellitus after administration of 48 U of Technosphere®/Insulin (TI) according to the teachings of the present invention.

The glucose elimination rate (GIR) was determined by the amount of glucose infusion required to maintain stable blood glucose of 120 mg/dL during the 540 min study period (FIG. 4). Forty-eight units TI provided a mean maximum concentration of insulin ($C_{max}$) of 114.8±44.1 (mean±SD) mIU/L and had a median time to maximum concentration ($T_{max}$) of 15 min, whereas 24 IU subcutaneous insulin (SC) had a $C_{max}$ of 63±10.1 mIU/L with a $T_{max}$ of 150 min. Technosphere®/Insulin reached maximal GIR values, 3.33±1.35 mg/min/kg, at 45 min, while at that timepoint, SC was only 1.58±1.03 and did not reach maximal value, 3.38±1.45 before 255 min, despite almost constant insulin concentrations. The data for GIR and insulin concentration for TI are also plotted individually versus time in FIG. 8. Once maximal insulin effect was reached, the concentration—effect relationship was the same for TI and SC. At 180 min, glucose disposal was 326±119 mg/kg or 61% of total for TI and 330±153 mg/kg (27% of total) for SC.

A fast, sharp increase in insulin concentration, similar to the early phase insulin response, provided maximal glucose elimination rate. Forty-eight units TI achieved maximal effect within 45 min, whereas it took 270 min for 24 IU SC to reach similar effect. This phenomenon is not caused by differences in the dose-effect relationship for the two insulin types, but reflects a difference in response when the increment in insulin concentration is more modest over time as opposed to the more rapid bioavailable insulin provided by Technosphere®/Insulin. This can have consequences for postprandial glucose control.

Figure 14A:
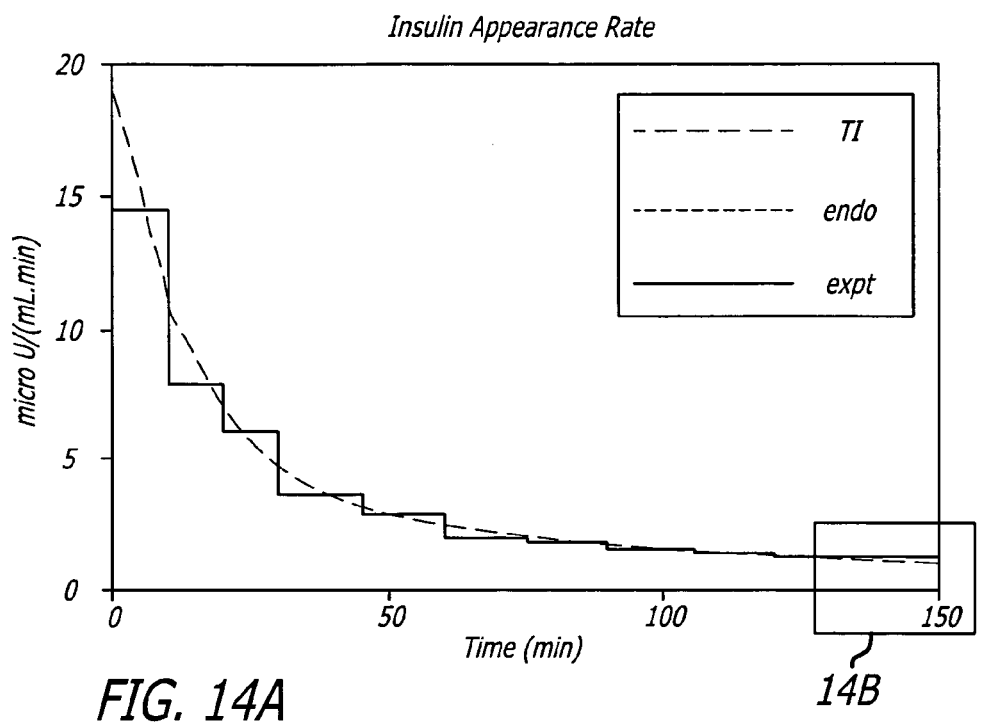
FIGS. 14A-B depict the insulin appearance rate over time for TI and endogenous insulin after administration of Technosphere®/Insulin (TI) in patients with type 2 diabetes according to the teachings of the present invention
Figure 14B:
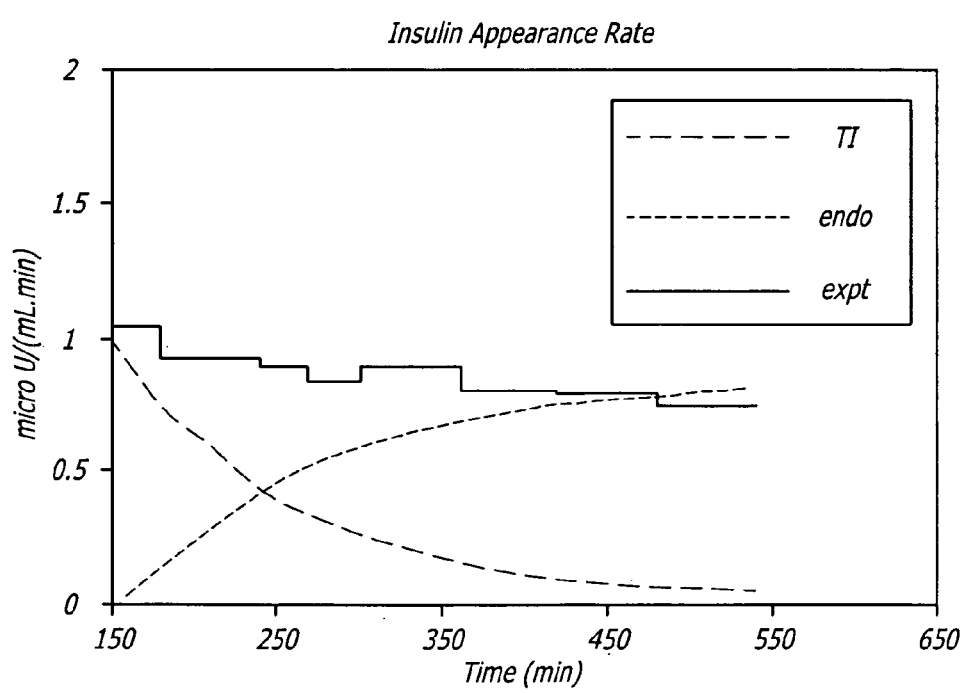

Additionally, three hours after dosing, 48 U TI and 24 IU SC had exerted the same glucose lowering effect. However, less than ⅓ of the total glucose lowering effect for the SC dose had been obtained. The glucose lowering activity 180 minutes after a meal was 74% for TI and 29% for SC insulin (FIG. 5). If the prandial insulin dose is titrated towards a goal of normoglycemia at three hours after a meal, the large remaining glucose lowering effect of SC insulin may increase the risk of late post prandial hypoglycemia, as compared to TI. In addition to confining the bulk of glucose lowering activity to a time period more similar to the glucose load created by a meal, the kinetics exhibited by TI also allowed for the reassertion of endogenous insulin secretion sooner, that is glycemic control is returned to homeostatic mechanisms. At late time points (>150 minutes), the fall in insulin concentration lags behind what would have been expected based on the decay rate seen at earlier time points. This can be understood as the superimposition of falling exogenous insulin (from TI) and rising endogenous insulin (FIG. 14). Endogenous insulin secretion should be accompanied by the production of C-peptide.

Figure 16:
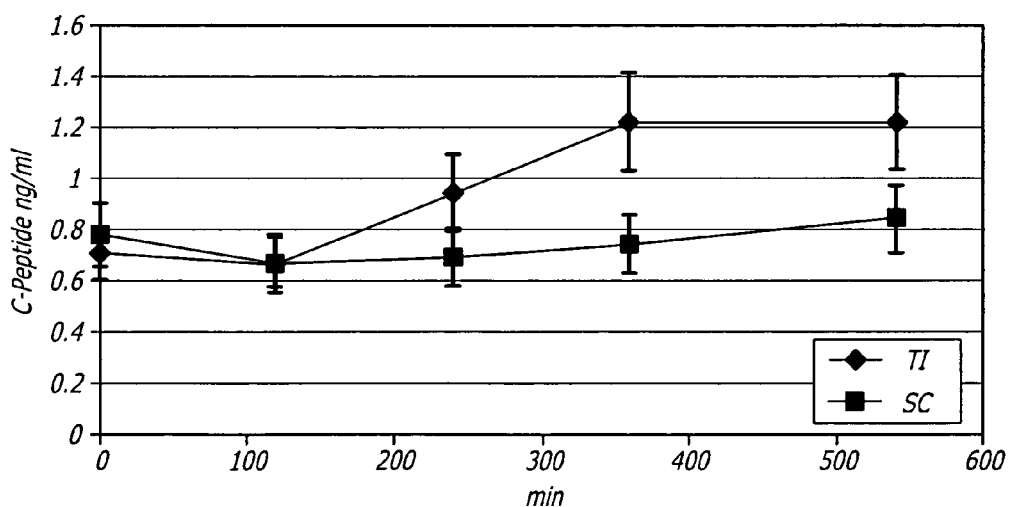
FIG. 16 depicts the levels of C-peptide after administration of Technosphere®/Insulin (TI) or SC insulin in individuals with type 2 diabetes mellitus according to the teachings of the present invention.

Mean serum C-peptide concentrations over time for inhaled Technosphere®/Insulin and injectable SC regular insulin are presented in FIG. 16. C-peptide concentrations were essentially unchanged during SC treatment but rose with TI treatment with a timing consistent with the model depicted in FIG. 14.

One of the most important aims of drug therapy in patients with type 2 diabetes is to restore or to replace the first phase of the meal-related insulin response which is lost early in the course of type 2 diabetes mellitus. The rapid onset and short duration of action of inhaled Technosphere®/Insulin should make it suitable for replacement of prandial insulin secretion in patients with diabetes mellitus.

Example 3

A Fast Insulin Spike does not Increase Risk of Hypoglycemia

Figure 15:
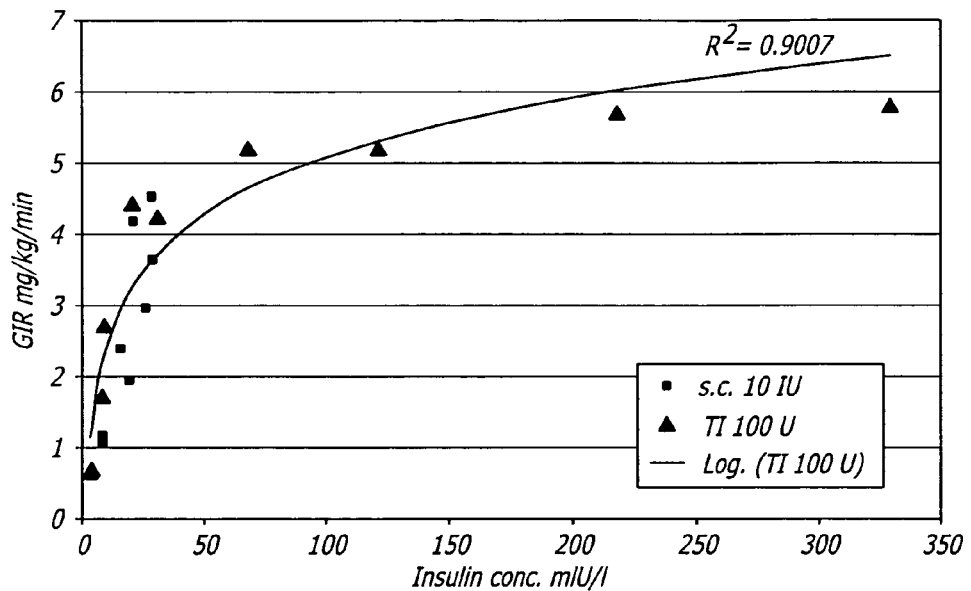
FIG. 15 depicts the relationship between insulin concentration and glucose elimination rate in individuals with type 2 diabetes mellitus after administration of intravenous (IV, 5 IU), SC (10 IU) or inhaled (TI, 100 U) insulin according to the teachings of the present invention.

It might be feared that the large concentrations of insulin, especially combined with their potentiation effect, would drive glucose elimination rates so high that they would pose a danger of inducing hypoglycemia. However this is not the case. Healthy human subjects under a euglycemic clamp were given intravenous, subcutaneous, or pulmonary insulin and the GIR was plotted against blood insulin concentration starting 20 minutes after administration. In normal subjects GIR hysteresis in response to insulin is much less pronounced than that for type 2 diabetics as disclosed in Example 1 above. Thus for normal subjects, 20 minutes after insulin administration and onward the relation between GIR and insulin concentration approximates a true mathematical function. It was observed that while at lower insulin concentrations the function appeared linear, consideration of higher concentrations showed that the relationship was actually logarithmic; as insulin concentration rose, ever smaller increases in GIR were obtained (FIG. 15). Thus glucose elimination did not reach catastrophically high rates and appeared unable to do so.

Example 4

Figure 6A:
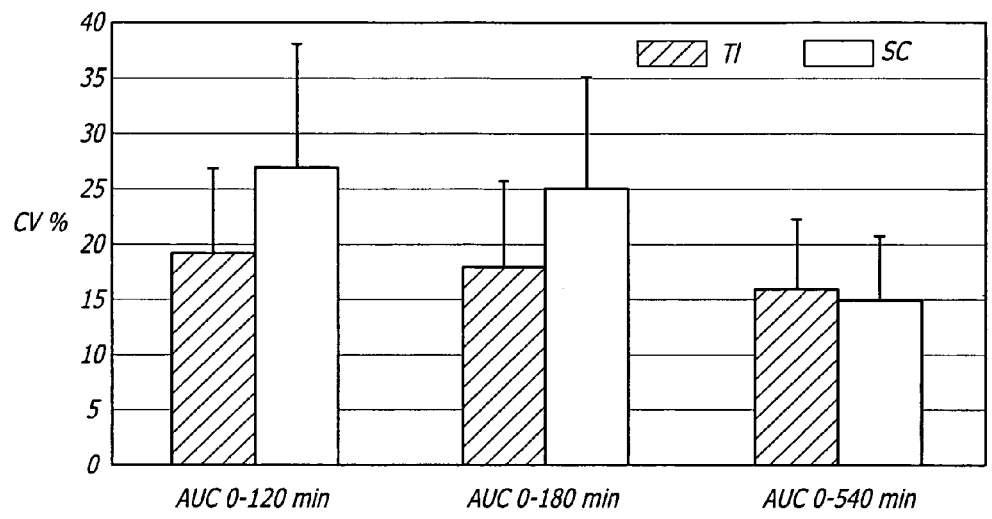
FIGS. 6A-B depict comparisons in intra-patient variability in GIR (FIG. 6A) and insulin concentration (FIG. 6B) in individuals with type 2 diabetes mellitus at various time points for subcutaneous (SC) and pulmonary (TI) insulin according to the teachings of the present invention.
Figure 6B:
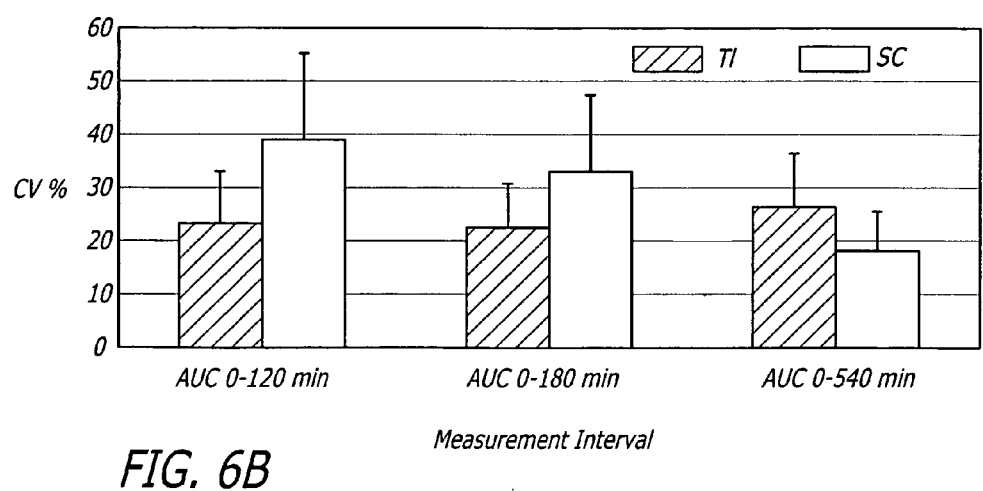

The Variability and Time-Action Profile of Inhaled Technosphere/Insulin Compares Favorably to that of Subcutaneously Administered Human Insulin Reproducibility of insulin's metabolic effect is critical to appropriate dose adjustment decisions including the selection of dose titration intervals and absolute dose quantity, in particular when near-normal glucose control is the objective. The intra-subject variability in insulin absorption and insulin effect between repeated doses of 48 U Technosphere®/Insulin and 24 IU subcutaneously injected human insulin (SC, Actrapid®) were compared. Each dose was given on three separate occasions on separate study days in a randomized sequence. Using a euglycemic glucose clamp, insulin concentrations and glucose infusion rates were measured over 540 min following each form of insulin administration (see FIG. 6). Variability of absorption and effect, expressed as CV % of $AUC_{0-t}$, was determined at 120, 180 and 540 min after dosing. For TI, the variability in insulin effect (GIR) was 23%, 22% and 26% at 120, 180 and 540 min respectively, as compared to 39%, 33% and 18% for SC (FIG. 6A). The variability in insulin concentrations (FIG. 6B) followed a similar pattern (19%, 18% and 16% for TI and 27%, 25% and 15% for SC). Thus for the glucose lowering effect, repeated inhalations of TI exhibited advantageous intra-patient variability compared to SC insulin during the first three hours after dosing. At 270 min, GIR for TI had returned to baseline, and the variability in measured plasma insulin at 540 min was comparable to the variation of SC insulin.

Example 5

A Randomized, Double-Blind, Placebo Controlled Study of the Efficacy and Safety of Inhaled Technosphere®/Insulin in Patients with Type 2 Diabetes Technosphere® dry powder, pulmonary insulin delivered via the small MannKind™ inhaler has a bioavailability that mimics normal, meal-related, first- or early-phase insulin release. This multicenter, randomized, double-blind, placebo-controlled study was conducted in type 2 diabetes mellitus patients inadequately controlled on diet or oral agent therapy (HbA1c>6.5% to 10.5%). A total of 123 patients were enrolled and 119, the intention-to-treat population (ITT), were randomized in a 1:1 ratio to receive prandial inhaled Technosphere®/Insulin (TI) from unit dose cartridges containing between 6 to 48 units of human insulin (rDNA origin) or inhaled Technosphere®/placebo for 12 weeks. TI was inhaled at the time of the first mouthful of food at each main or substantive meal of the day, amounting to 3 or 4 administrations per day throughout the 12 week trial. Subjects continued whatever oral diabetes drugs they were using prior to entering the study. Differences in HbA1c from the first and final treatment visits, and between the first and two intermediate visits, were determined, as was the change in blood glucose, as AUC at various time points, and $C_{max}$ and $T_{max}$, after a meal challenge.

Patients were given a standardized meal several times during the study and their blood glucose levels measured. The study drug was administered at the study site in conjunction with a standardized breakfast (Uncle Ben's Breakfast Bowl™) that was prepared at the site. Fasting plasma glucose was measured immediately before the meal. Spirometry was performed before the subject took the first dose of study drug. Subjects then inhaled the study drug and, within 60 seconds, performed a single spirometry test procedure. Within 90 seconds of the study drug inhalation, and after the spirometry test, the subject began eating the test meal. Once the meal was completed, the plasma glucose values and glucose meter readings were obtained at immediately before and at 30, 60 and 120 minutes after beginning the meal.

Figure 11:
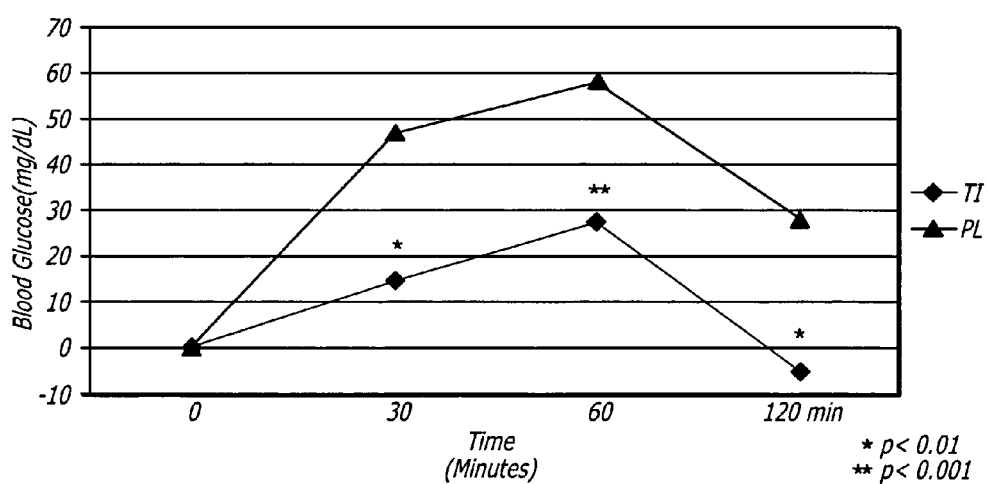
FIG. 11 depicts maintenance of the effects of inhaled insulin postprandial glucose levels after three months of insulin therapy in individuals with type 2 diabetes mellitus with Technosphere®/Insulin (TI) or placebo (PL) according to the teachings of the present invention.
Figure 12A:
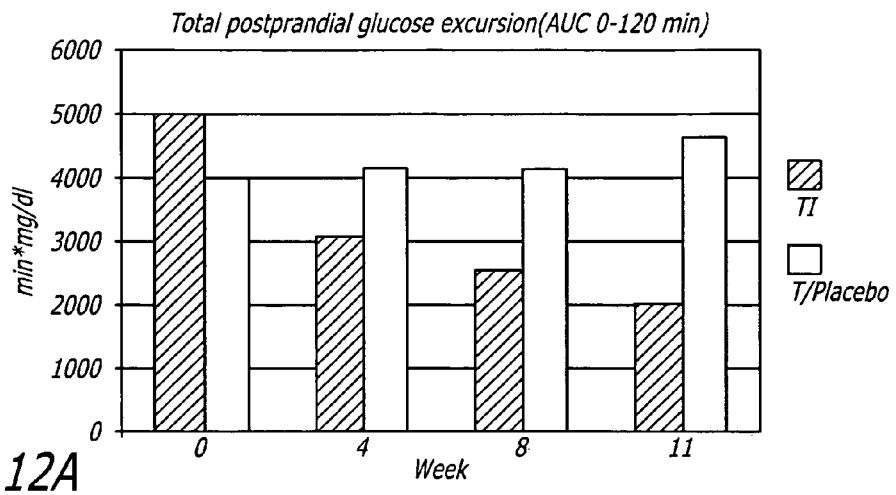
FIGS. 12A-B depict total (FIG. 12A) and maximum (FIG. 12B) postprandial glucose excursion in individuals with type 2 diabetes mellitus after administration of Technosphere®/Insulin (TI) or placebo (PL) according to the teachings of the present invention.
Figure 12B:
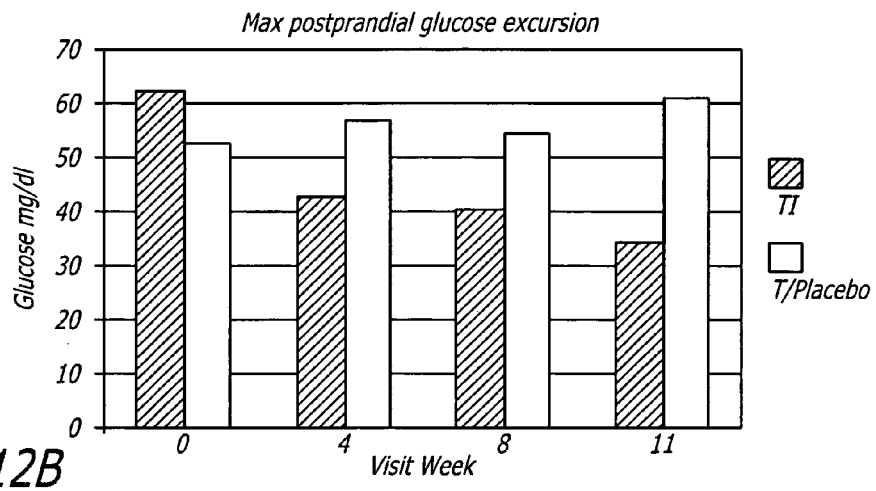
Figure 13:
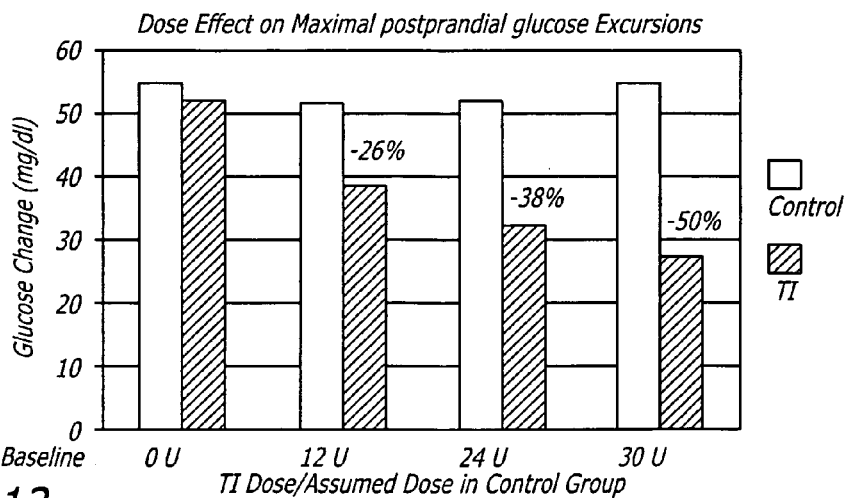
FIG. 13 depicts the dose effect on maximal postprandial glucose excursions after administration of Technosphere®/Insulin (TI) compared to the assumed dose in a control group (Control) in individuals with type 2 diabetes mellitus according to the teachings of the present invention.

For patients receiving either TI or placebo, blood glucose rose after meal challenge, but significantly less for the TI group and returned to baseline sooner (FIG. 11). Thus total glucose exposure, expressed as $AUC_{0-120}$, (FIG. 12A) and maximal glucose excursion ($C_{max}$; FIG. 12B) were reduced. FIG. 13 shows the observed difference in maximal glucose excursions between the patients receiving different dosages of TI versus those in the control arm. Note that at a dose of 30 U the maximal glucose excursions for the TI patients were 50% of the level for the patients in the control group. Also note that the average glucose excursion was about 28 mg/dL vs. 50 mg/dL when the TI patients entered the study. An excursion of only 28 mg/dL is within the range that is a goal of clinical treatment.

Figure 17:
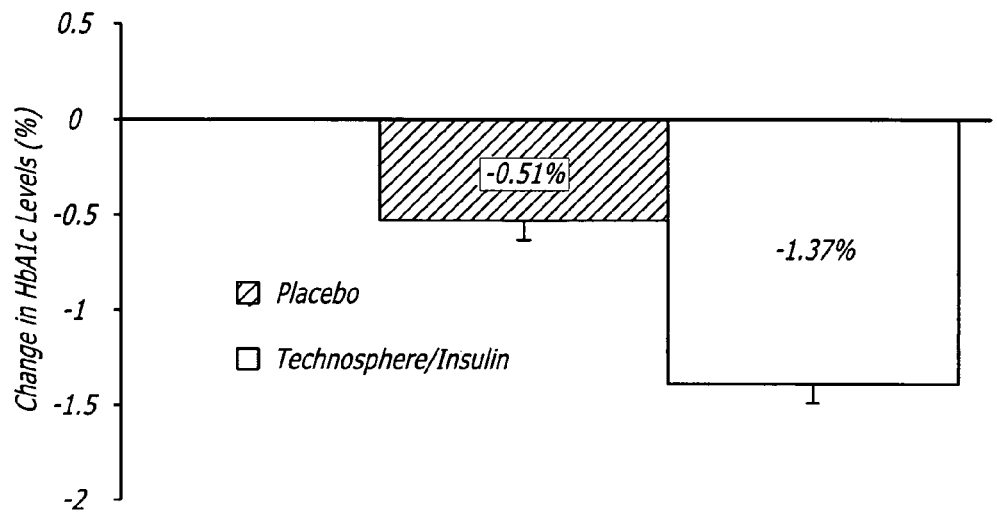
FIG. 17 depicts the change in mean glycosylated hemoglobin (HbA1c) levels after 12 weeks of administration of Technosphere®/Insulin (TI) or placebo in individuals with type 2 diabetes mellitus according to the teachings of the present invention.

Glycosylated hemoglobin A1c (HbA1c) results were analyzed by a pre-determined statistical analysis plan for the Primary Efficacy Population (PEP, defined prior to un-blinding as those who adhered to study requirements including minimal dosing and no adjustments of concomitant diabetes drugs), for a PEP Sub-group A (those with baseline HbA1c of 6.6 to 7.9%), for a PEP Sub-group B (those with baseline HbA1c of 8.0 to 10.5%), as well as for the ITT. These results are summarized in Table 1, and for PEP Sub-group B in FIG. 17. In this "individualized dose" study, the mean dose of TI used before each meal in the active treatment group was approximately 30 units, with 28 units used in PEP Sub-group A and 33.5 units used in PEP Sub-group B.

TABLE 1

HbA1c Pharmacokinetics

|  | Technosphere ®/Placebo | Technosphere ®/Insulin |
| --- | --- | --- |
| PEP n = 90 | n = 42 | n = 48 |
| Mean HbA1c Baseline (%) | 7.75 | 7.74 |
| Mean Δ from baseline | −0.32 (p = 0.0028) | −0.76 (p < 0.0001) |
| Comparison to Placebo |  | p = 0.0019 |
| PEP Sub-group B n = 35 | n = 18 | n = 17 |
| Mean HbA1c Baseline (%) | 8.52 | 8.72 |
| Mean Δ from baseline | −0.51 (p = 0.0094) | −1.37 (p < 0.0001) |
| Comparison to Placebo |  | p = 0.0007 |
| PEP Sub-group A n = 55 | n = 24 | n = 31 |
| Mean HbA1c Baseline (%) | 7.16 | 7.19 |
| Mean Δ from baseline | −0.18 (p = 0.1292) | −0.43 (p = 0.0001) |
| Comparison to Placebo |  | p < 0.05 |
| ITT (LOCF) n = 119 | n = 61 | n = 58 |
| Mean HbA1c Baseline (%) | 7.78 | 7.87 |
| Mean Δ from Baseline (%) | −0.31 (p = 0.0020) | −0.72 (p < 0.0001) |
| Comparison to Placebo |  | p = 0.0016 |

No episodes of severe hypoglycemia occurred in the TI group. There was no statistically significant difference in the rate of hypoglycemic events between those subjects receiving placebo and those receiving TI. (Table 2).

TABLE 2

Incidence of Hypoglycemia after Pulmonary Administration of TI

|  | Technosphere ®/Insulin | Technosphere ®/Placebo |
| --- | --- | --- |
| Hypoglycemia (% of patients) | 42.6% | 35.5% |
| Hypoglycemia (events/week) | 0.16 | 0.20 |

Figure 19A:
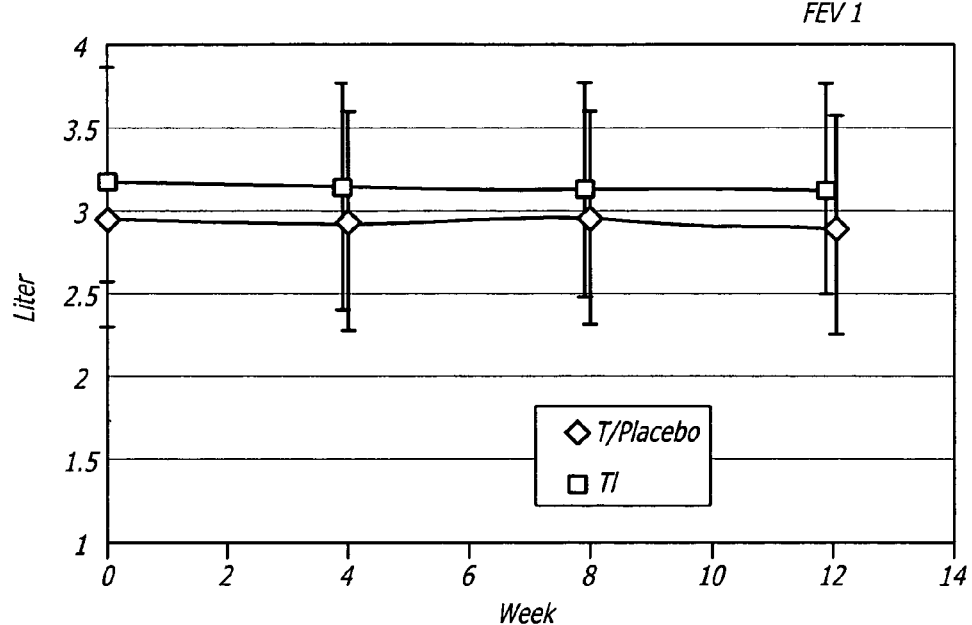
FIGS. 19A-B depict pulmonary function, expressed as forced expiratory volume in one second (FEV1, FIG. 19A) and forced vital capacity (FVC, FIG. 19B) over time in a three month placebo-controlled clinical study with Technosphere®/Insulin according to the teachings of the present invention.
Figure 19B:
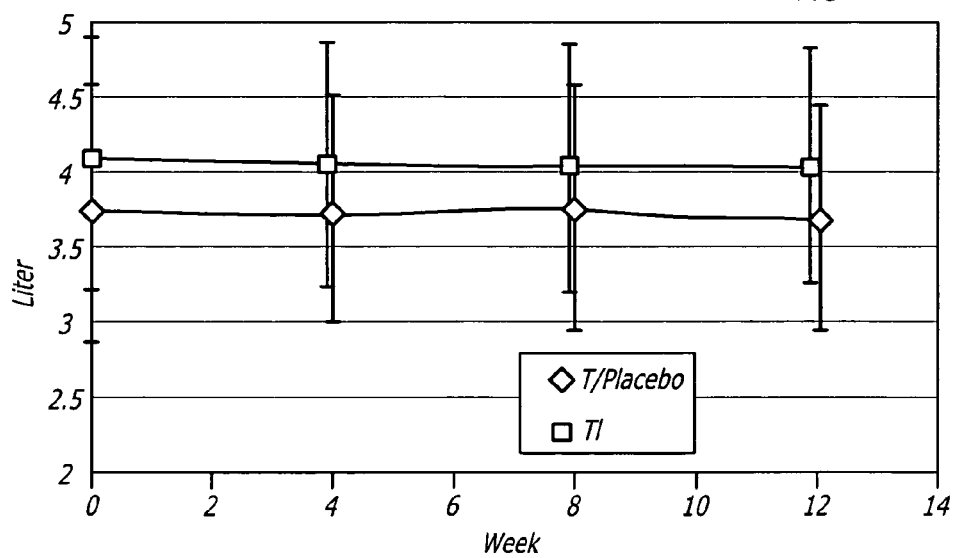

Pulmonary function tests, including DLco (diffusing capacity of the lung for carbon monoxide) (Table 3), FEV1 (forced expiratory volume in one second), and total alveolar volume (forced vital capacity, FVC) showed no significant differences between patients on TI compared to their baseline values or compared to the results of those receiving placebo (FIG. 19).

TABLE 3

Pulmonary Function After Pulmonary Administration of TI

| DLco | Technosphere ®/Insulin | Technosphere ®/Placebo |
| --- | --- | --- |
| 0 weeks | 24.9 ± 4.8 | 26.5 ± 5.6 |
| 12 weeks | 25.0 ± 4.5 | 25.7 ± 5.2 |

Figure 18:
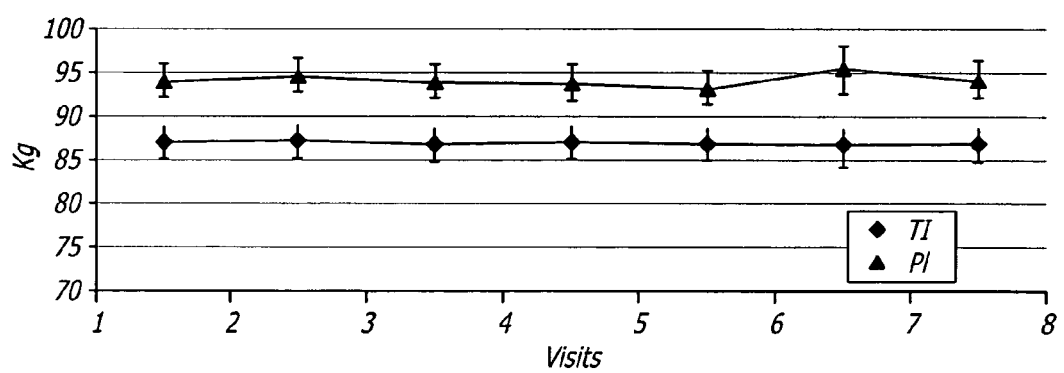
FIG. 18 depicts weight levels in individuals with type 2 diabetes mellitus administered Technosphere®/Insulin (TI) or placebo (PL) according to the teachings of the present invention.

There was no evidence of induction of insulin antibodies with TI (Table 4) or of weight gain (FIG. 18) during the 12 week period of exposure.

TABLE 4

Incidence of Antibodies to Insulin after Pulmonary Administration of TI

|  | Technosphere ®/Insulin | Technosphere ®/Placebo |
| --- | --- | --- |
| Negative at Visit 1/Negative at Visit 9 | 38 | 34 |

TABLE 4-continued

Incidence of Antibodies to Insulin after Pulmonary Administration of TI

|  | Technosphere ®/ Insulin | Technosphere ®/ Placebo |
|---|---|---|
| Negative at Visit 1/Positive at Visit 9 | 2 | 3 |
| Positive at Visit 1/Positive at Visit 9 | 8 | 10 |
| Positive at Visit 1/Negative at Visit 9 | 2 | 4 |

In conclusion, this study has demonstrated that Technosphere® pulmonary insulin, in replication of the kinetics of the early phase of insulin release, when used in patients with inadequate glycemic control previously on only diet and exercise alone or on oral agent therapy, safely and significantly improved glycemic control with no significantly increased incidence of hypoglycemia, no induction of insulin antibodies, no tendency toward weight gain, and no evidence of overall impact on pulmonary function.

Example 6

A FDKP/Insulin Provides Glycemic Control when Administered from 10 Minutes before to 30 Minutes after the Beginning of a Meal A clinical trial was conducted to evaluate the effect of the timing of pulmonary administration of an FDKP-insulin complex as a dry powder (FDKP/Insulin; also referred to as Technosphere®/Insulin, TI). Subjects were type 1 diabetics who were not receiving any drug, other than insulin, for treatment of their diabetes, nor any other drug affecting carbohydrate metabolism. The trial was a prospective, single-center, randomized, crossover, open-label study. At each of 8 treatment visits, human subjects inhaled a single individualized dose 10 min before (B10), immediately before (C0), 15 min after (A15), or 30 min after (A30) eating an isocaloric (I; approximately 500 kcal) or hypercaloric (H; approximately 720 kcal) meal. Each subject received each of the eight possible timings of administration/meal combinations (i.e., B10I, B10H, C0I, C0H, A15I, A15H, A30I, and A30H) on separate occasions and in random order, with 1 to 14 days elapsing between treatment visits (see FIG. 20). Blood samples taken before and after inhalation of the TI and meal consumption were used to determine pharmacokinetic parameters for glucose and insulin.

The dose of TI was individualized for each subject. The individualized dose was based on the carbohydrate content of the meal to be consumed during the treatment visit, a correction factor for TI bioavailability, and the subject's individual "insulin factor" (Fi), which was determined during a preliminary visit before the first treatment visit. The method of dose individualization was calculated at each treatment visit according to the following formula:

IUdose=(BE*Fi)/0.30 where:
IUdose was the number of IU of TI to be administered
BE (Brot-Einheit, bread unit) was 1/10 of the carbohydrate content (in grams) of the meal to be consumed (5 for the isocaloric and 8.5 for the hypercaloric meals, respectively)
Fi was the individual insulin factor, equivalent to the units of insulin required to cover one BE.
0.30 was the correction factor for TI bioavailability.

After calculation, the dose of TI was rounded to the nearest dose that could be administered using multiples of the TI cartridges, which contained 6 U, 12 U, or 24 U insulin.

During treatment visits, insulin was infused intravenously at a rate of 1 IU/hour and glucose was infused at a rate adjusted to achieve a stable capillary blood glucose concentration within the range of 80 to 140 mg/dL before meal consumption and/or TI inhalation. This infusion was continued without adjustment during the study. Venous blood samples were collected at varying intervals, starting at 45 min prior to meal consumption and continuing until four hours after consumption. The samples were used for determination of blood (serum) glucose and serum insulin concentrations.

The primary efficacy variable was blood glucose concentration. As well as providing a profile of the blood glucose concentration before and after TI and meal administration, the blood glucose concentration values were used to calculate the following pharmacokinetic parameters to describe total glucose excursion:

Maximal (Cmax) and minimal (Cmin) blood glucose concentrations after the start of meal consumption, corrected for baseline values.
Minimal (Cmin) blood glucose concentrations after TI inhalation, corrected for baseline values.
Time to Cmax (Tmax), time to Cmin (Tmin), and time to last glucose excursion above baseline levels after start of meal ($T_x$).
Area under the blood glucose concentration curve (AUC) was calculated using trapezoidal method for three separate time periods:
AUC: from 10 min before to 240 min after start of meal
AUC1: from 10 min before to $T_x$, and
AUC2: from $T_x$ to 240 min after start of meal.
Blood glucose concentration at 1 hour (BG1) and 2 hours (BG2) after start of meal.

To ensure baselines were comparable between treatments, blood glucose and serum insulin baselines were computed based on the average of the −45, −30 and −20 min pre-meal measurements.

The secondary efficacy variable was serum insulin concentration. Insulin absorption was assumed to be independent of the time of dose relative to meals. The pharmacokinetic profile for insulin was determined based on serum insulin values normalized for dose and using dosing time as T=0 for all data sets. Mean Cmax (peak insulin concentration), AUC (area under the insulin concentration time curve), Tmax (time from dosing to peak concentration), time from dosing to reach 50% of Cmax (early T50%), and time from Tmax to 50% decline in Cmax (late T50%) were calculated. Following normalization (to a hypothetical 100 IU) for individual dose, intra- and inter-individual variation was determined as the CV % for the mean of individual Cmax and AUC.

Figure 21A:
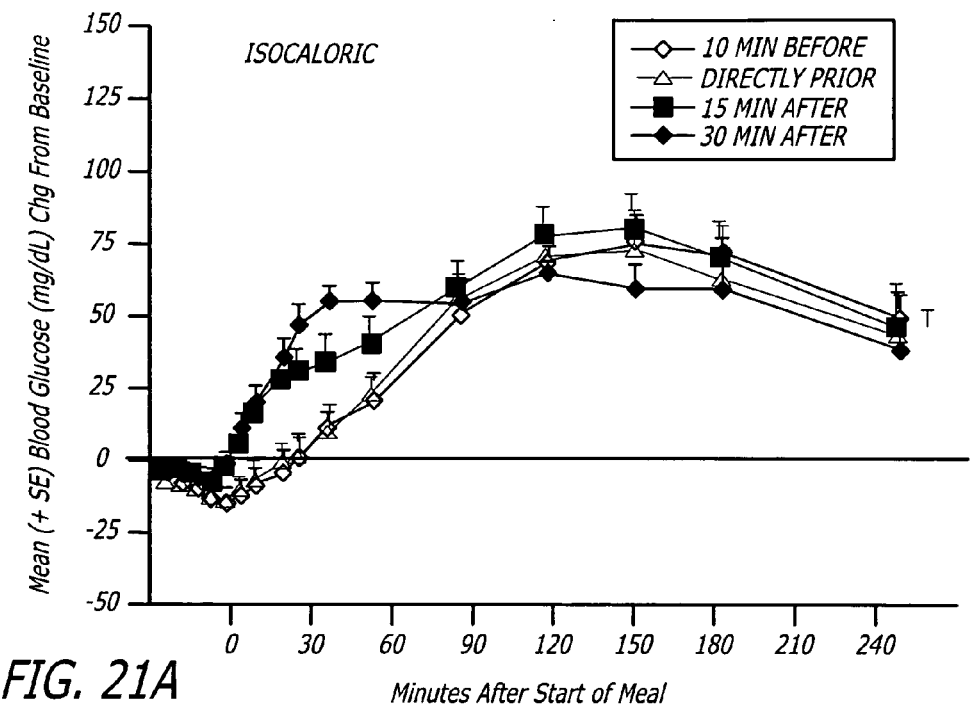
FIGS. 21A-B depict the baseline-corrected blood glucose concentration versus time by treatment group after administration of Technosphere®/Insulin and a isocaloric meal (FIG. 21A) or a hypercaloric meal (FIG. 21B) according to the teachings of the present invention.
Figure 21B:
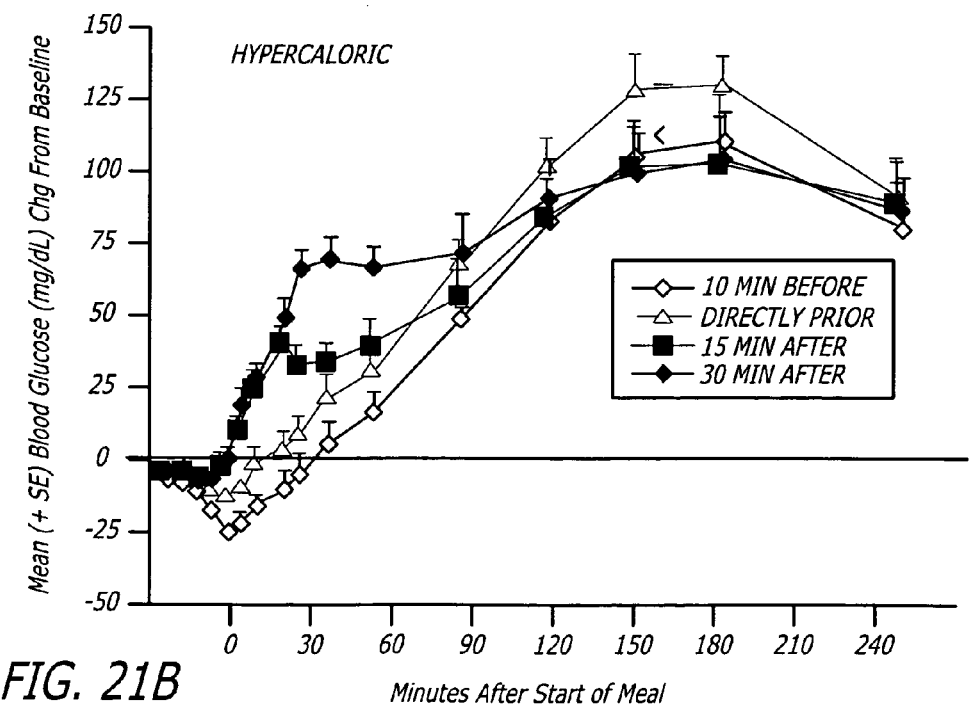

The primary efficacy variable was blood glucose concentration. The effect of timing of administration of TI on the mean (SD) baseline-corrected blood glucose concentrations before and after an isocaloric or hypercaloric meal is illustrated in FIG. 21 for the primary efficacy population. Overall, the comparative excursions in blood glucose, while greater after the hypercaloric meal than the isocaloric meal, were similar in profile for the two meal types but were dependent upon the timing of administration of TI (FIG. 21). Notably, when TI was inhaled 10 min before either meal, there was an initial decrease in blood glucose levels. After reaching a nadir about 10 min after the start of the meal, blood glucose levels rose above baseline levels approximately 30 min. later. By comparison, when TI was inhaled 15 or 30 min after the start of the meal, glucose levels rose above baseline approximately 10-15 min after starting meal consumption (FIG. 21).

A comparison of pharmacokinetic parameters for blood glucose following each type of meal and for each timing of administration of TI is shown in Table 5 for the primary efficacy population. As indicated by the mean minimum blood glucose levels (Cmin, expressed as change from baseline) and initial period of the area under the glucose concentration curve (AUC1), the greatest reduction in blood glucose occurred when TI was inhaled 10 min before subjects started eating either the isocaloric or hypercaloric meal (Cmin−21 mg/dL and −27 mg/dL, respectively; AUC1−722 and −907 min*mg/dL, respectively) (Table 5). When TI was inhaled either 10 min before or immediately before meal consumption, blood glucose levels reached a nadir in approximately 10 to 13 min (as indicated by the median Tmin), and did not rise above baseline levels until 20 to 30 min later (as indicated by the median TX) (Table 5). By comparison, when TI was inhaled either 15 min or 30 min after the start of meal consumption, reductions in blood glucose were smaller (Cmin− 10 to −13 mg/dL; AUC1−141 to −176 min*mg/dL), they occurred sooner (Tmin 3 to 5 min), and they were more short-lived (approximately 6 to 7 min). The largest individual reductions in blood glucose were in subjects who inhaled TI immediately before isocaloric or hypercaloric meal consumption (Cmin−58 mg/dL and −57 mg/dL, respectively).

Mean Cmax values (expressed as change from baseline), AUC, and AUC2 were generally comparable whether TI was given before or after a particular type of meal, though all were lower after the isocaloric meal than the hypercaloric meal (Table 5). The median time to Cmax (Tmax) ranged between 120 and 165 min for the isocaloric meal and between 150 to 180 min for the hypercaloric meal. Mean blood glucose levels one hour (BG1) and two hours (BG2) after the start of meal showed no consistent relationship to time of inhalation of TI relative to either meal (Table 5), although BG1 was lowest when TI was given 10 min before the start of a meal and highest when given 30 min after the start of a meal.

The comparative effects of different times of TI inhalation on selected glucose pharmacokinetic parameters was expressed as a ratio of the value at the corresponding C0 (i.e., B10/C0, A15/C0, and A30/C0) for each meal type. These ratios, along with their 95% confidence intervals (CI), are summarized in Table 6 (primary efficacy population). These results indicated that the comparative effects of inhalation of TI immediately before meal consumption were no different than that of inhalation 10 min before meal consumption on any pharmacokinetic parameter (i.e., most B0/C0 ratios were close to 1 and the 95% CI encompassed 1 within their range). Most comparisons also yielded no differences between TI immediately before meal consumption and 15 or 30 min after.

TABLE 5

Summary of Blood Gluclose Pharmacokinetic Parameters by Meal and Timing of Administration of Technosphere ®/Insulin

| | Isocaloric Meal Timing of Dosing | | | | Hypercaloric Meal Timing of Dosing | | | |
|---|---|---|---|---|---|---|---|---|
| Parameter | B10 (N = 12) | C0 (N = 12) | A15 (N = 12) | A30 (N = 12) | B10 (N = 12) | C0 (N = 12) | A15 (N = 12) | A30 (N = 12) |
| $C_{min}$ (mg/dL) | −21 (14) | −18 (15) | −11 (14) | −13 (7) | −27 (8) | −16 (14) | −11 (7) | −10 (7) |
| $T_{min}$ (minutes) | 10 | 13 | 5 | 5 | 13 | 10 | 5 | 3 |
| $C_{max}$ (mg/dL) | 86 (28) | 84 (38) | 88 (36) | 81 (23) | 119 (46) | 130 (40) | 116 (50) | 113 (47) |
| $T_{max}$ (minutes) | 165 | 135 | 150 | 120 | 180 | 180 | 150 | 165 |
| AUC1 (min * mg/dL) | −722 (950) | −648 (840) | −154 (180) | −176 (176) | −907 (511) | −418 (549) | −149 (148) | −141 (149) |
| AUC2 (min * mg/dL) | 11499 (4640) | 10989 (7030) | 13055 (7616) | 12431 (4682) | 14818 (6018) | 17395 (6050) | 16346 (8326) | 18402 (8968) |
| AUC (min * mg/dL) | 10777 (5339) | 10342 (7349) | 12901 (7739) | 12255 (4895) | 13911 (5840) | 16977 (6008) | 16197 (8407) | 18261 (8982) |
| BG1 (mg/dL) | 21 (32) | 23 (25) | 41 (32) | 55 (23) | 16 (23) | 33 (21) | 38 (31) | 65 (24) |
| BG2 (mg/dL) | 68 (34) | 71 (34) | 78 (32) | 68 (32) | 81 (28) | 101 (33) | 82 (47) | 89 (46) |
| $T_x$ (minutes) | 36.6 | 36.9 | 11.7 | 11.3 | 42.2 | 33.2 | 12.4 | 10.3 |

All values are presented as mean (SD) except for $T_{min}$, $T_{max}$ and $T_x$, which are median.

TABLE 6

Comparison of Blood Glucose Pharmacokinetic Parameters Relative to Inhalation of Technosphere ®/Insulin Immediately Before Meal Consumption

| | Isocaloric Meal Ratio of Test to Reference Parameter | | | Hypercaloric Meal Ratio of Test to Reference Parameter | | |
|---|---|---|---|---|---|---|
| Parameter | B10/C0 (N = 12) | A15/C0 (N = 12) | A30/C0 (N = 12) | B10/C0 (N = 12) | A15/C0 (N = 12) | A30/C0 (N = 12) |
| $C_{min}$ | 0.997 (0.470, 2.112) | 0.425 (0.210, 0.860) | 0.581 (0.302, 2.112) | 1.748 (0.470, 2.112) | 0.988 (0.470, 2.112) | 0.532 (0.470, 2.112) |
| AUC1 | 0.608 (0.133, 2.775) | 0.300 (0.067, 1.334) | 0.214 (0.053, 0.863) | 1.995 (0.803, 4.762) | 0.381 (0.154, 0.942) | 0.334 (0.137, 0.814) |
| $C_{max}$ | 1.002 (0.809, 1.240) | 1.088 (0.887, 1.334) | 0.953 (0.784, 1.157) | 0.848 (0.630, 1.143) | 0.778 (0.581, 1.041) | 0.814 (0.616, 1.076) |

TABLE 6-continued

Comparison of Blood Glucose Pharmacokinetic Parameters Relative to
Inhalation of Technosphere ®/Insulin Immediately Before Meal Consumption

| | Isocaloric Meal Ratio of Test to Reference Parameter | | | Hypercaloric Meal Ratio of Test to Reference Parameter | | |
|---|---|---|---|---|---|---|
| Parameter | B10/C0 (N = 12) | A15/C0 (N = 12) | A30/C0 (N = 12) | B10/C0 (N = 12) | A15/C0 (N = 12) | A30/C0 (N = 12) |
| AUC2 | 1.077 (0.727, 1.596) | 1.035 (0.711, 1.506) | 1.158 (0.809, 1.657) | 0.780 (0.497, 1.226) | 0.771 (0.496, 1.198) | 0.907 (0.594, 1.385) |
| AUC | 1.105 (0.555, 2.200) | 0.722 (0.378, 1.380) | 1.245 (0.671, 2.310) | 0.727 (0.426, 1.238) | 0.753 (0.448, 1.266) | 0.910 (0.553, 1.500) |
| BG1 | 0.833 (0.451, 1.536) | 1.203 (0.656, 2.207) | 7.932 (1.143, 3.267) | 0.768 (0.491, 1.200) | 1.256 (0.810, 1.948) | 1.985 (1.379, 2.857) |
| BG2 | 0.630 (0.258, 1.536) | 1.109 (0.468, 2.627) | 0.906 (0.399, 2.058) | 0.771 (0.533, 1.114) | 0.665 (0.464, 0.953) | 0.758 (0.537, 1.069) |

All values are presented as ratio (95% confidence interval).

Figure 22A:
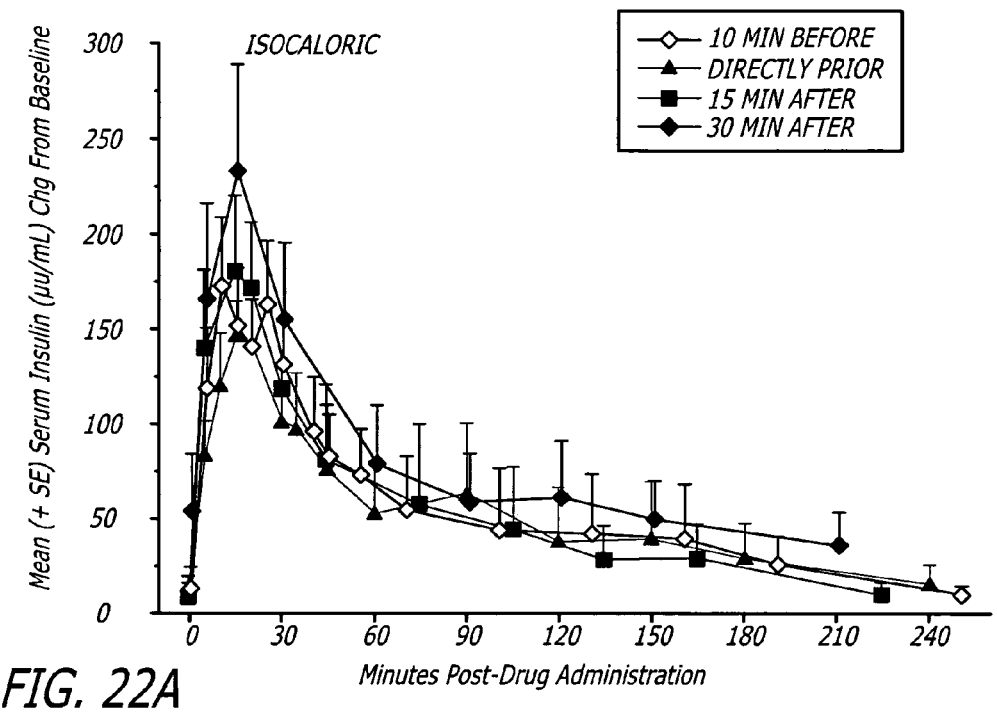
FIGS. 22A-B depict the baseline-corrected serum insulin concentration versus time by treatment group after administration of Technosphere®/Insulin and a isocaloric meal (FIG. 22A) or a hypercaloric meal (FIG. 22B) according to the teachings of the present invention.
Figure 22B:
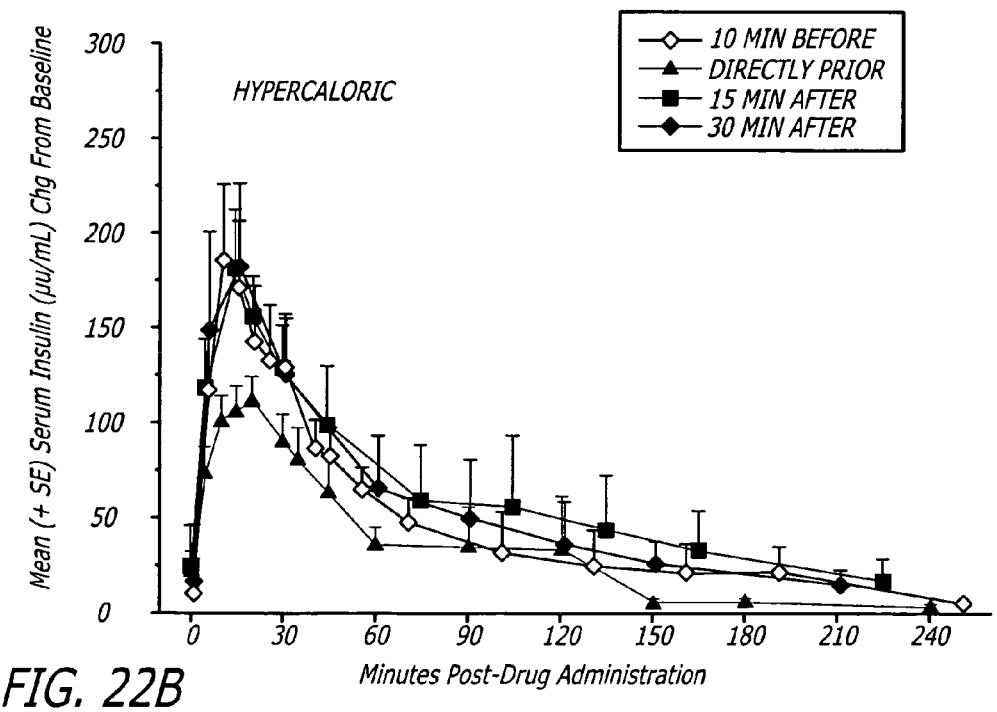

The secondary efficacy variable was serum insulin concentration. The profile of the mean (SD) baseline-corrected serum insulin concentrations after TI inhalation is illustrated in FIG. 22 for the primary efficacy population. There was a sharp increase in serum insulin immediately after inhalation of TI, which was independent of dosing time and meal type. Serum insulin concentrations peaked approximately 15 min after dosing and thereafter rapidly declined until 60 min after administration, after which there was a slower decline, consistent with first-order elimination.

A comparison of pharmacokinetic parameters for serum insulin for each timing of administration of TI relative to each type of meal is shown in Table 7 for the primary efficacy population. Overall, the mean Cmax (expressed as change from baseline) and AUC values for serum insulin were generally comparable, irrespective of meal type and whether TI was given before or after the meal (Table 7). Irrespective of meal type and time of dosing relative to the meal, serum insulin concentrations rose rapidly after TI inhalation, with the early T50% ranging between three and five min and peak concentrations being observed 10 to 20 min after administration. Thereafter, serum insulin concentrations declined, with the late T50% ranging between 33 and 43 min, and again showed no consistent variation with time of inhalation of TI or meal type (Table 7).

and up to 30 minutes after starting a meal provides comparable glycemic control in the postprandial period.

Example 7

Bioavailability of Insulin in Diketopiperazine Pulmonary Formulation

Subjects and Methods

The study was reviewed and approved by the ethical review committee of the Heinrich-Heine-University, Dusseldorf, and conducted according to local regulations, the Declaration of Helsinki and the rules of Good Clinical Practice.

The study was conducted with 5 healthy male volunteers. Inclusion criteria were good health, as judged by physical examination, age: 18 to 40 years, body mass index: 18 to 26 kg/m$^2$, capability to reach peak inspiratory flow of ≥4 L/sec measured by a computer assisted spirometry and a FEV1 equal to or greater than 80% of predicted normal (FEV1=forced expiratory volume in one second). Exclusion criteria were diabetes mellitus type 1 or 2, prevalence of human insulin antibodies, history of hypersensitivity to the study medication or to drugs with similar chemical structures,

TABLE 8

Summary of Serum Insulin Pharmacokinetic Parameters by Meal and
Timing of Administration of Technosphere ®/Insulin

| | Isocaloric Meal Timing of Dosing | | | | Hypercaloric Meal Timing of Dosing | | | |
|---|---|---|---|---|---|---|---|---|
| Parameter | B10 (N = 12) | C0 (N = 12) | A15 (N = 12) | A30 (N = 12) | B10 (N = 12) | C0 (N = 12) | A15 (N = 12) | A30 (N = 12) |
| $C_{max}$ (mIU/L) | 207 (145) | 179 (125) | 188 (137) | 215 (196) | 211 (138) | 137 (74) | 191 (114) | 193 (163) |
| $T_{max}$ (minutes) | 13 | 15 | 15 | 15 | 10 | 20 | 15 | 15 |
| AUC (min * mIU/L) | 12635 (15681) | 11291 (17449) | 11642 (18373) | 12649 (14838) | 10654 (7623) | 7710 (7313) | 12874 (16785) | 11662 (13210) |
| Early $T_{50\%}$ (min) | 4 | 4 | 3 | 3 | 4 | 5 | 4 | 3 |
| Late $T_{50\%}$ (min) | 40 | 40 | 33 | 43 | 43 | 42 | 39 | 39 |

All values are presented as mean (SD) except for $T_{max}$ and $T_{50\%}$, which are median.

Thus inhalation of an individualized dose of TI provides glycemic control in subjects with type 1 diabetes who consume isocaloric or hypercaloric meals. There were no differences in the pharmacokinetics of insulin based on the timing of administration relative to the meals. The administration of TI between 10 minutes prior to the time of the first bite of food history or severe or multiple allergies, treatment with any other investigational drug in the last three months before study entry, progressive fatal disease, history of drug or alcohol abuse, current drug therapy with other drugs, history significant cardiovascular, respiratory, gastrointestinal, hepatic, renal, neurological, psychiatric and/or hematological disease, ongoing respiratory tract infection or subjects defined as being smokers with evidence or history of tobacco or nicotine use.

Conduct of the Study

On the morning of the study days, the subjects came to the hospital (fasting, except for water, from midnight onward) at 7:30 a.m. The subjects were restricted from excessive physical activities and an intake of alcohol for 24 hours before each treatment day. They were randomly assigned to one of the three treatment arms. The subjects received a constant intravenous regular human insulin infusion, which was kept at 0.15 mU min$^{-1}$ kg$^{-1}$ so that serum insulin concentrations were established at 10-15 μU/mL during a period of two hours before time point 0. This low-dose infusion was continued throughout the test to suppress endogenous insulin secretion. Blood glucose was kept constant at a level of 90 mg/dL throughout the glucose clamp by a glucose controlled infusion system (Biostator™). The glucose clamp algorithm was based on the actual measured blood glucose concentration and the grade of variability in the minutes before to calculate the glucose infusion rates for keeping the blood glucose concentration constant. The insulin application (5 IU IV or 10 IU SC injection or three deep breaths inhalation per capsule (2 capsules with 50 U each) applied with a commercial inhalation device (Boehringer Ingelheim)) had to be finished immediately before time point 0. The duration of the clamp experiment was six hours from time point 0. Glucose infusion rates, blood glucose, serum-insulin and C-peptide were measured.

Bioefficacy and Bioavailability

To determine bioefficacy, the areas under the curve of the glucose infusion rates were calculated for the first three hours (AUC0-180) after the administration and for the overall observation period of six hours after the administration (AUC0-360) and were correlated to the amount of insulin applied. To determine bioavailability, the areas under the curve of the insulin concentrations were calculated for the first three hours (AUC0-180) after the administration and for the overall observation period of six hours after the administration (AUC0-360) and correlated to the amount of insulin applied.

In this clamp study, inhalation of 100 U of Technosphere®/Insulin was well tolerated and was demonstrated to have a substantial blood glucose lowering effect with a relative bioavailability of 25.8% for the first three hours as calculated from the achieved serum insulin concentrations. Technospheres® are microparticles (also referred to herein as microspheres) formed of diketopiperazine that self-assembles into an ordered lattice array at particular pHs, typically a low pH. They typically are produced to have a mean diameter between about 1 and about 5 μm.

Results

Figure 23A:
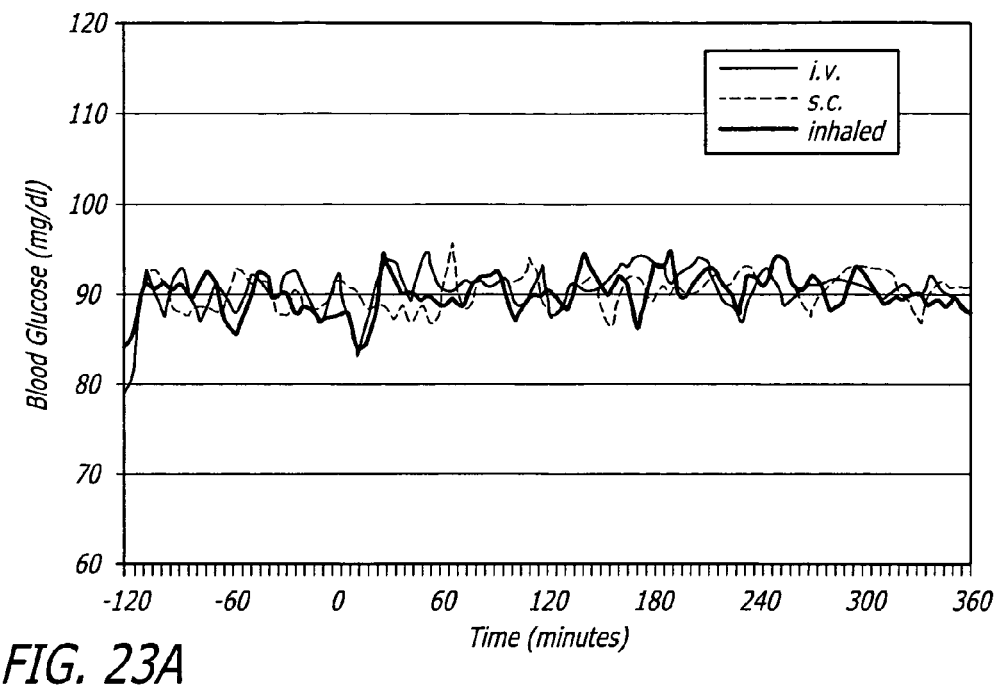
FIGS. 23A-B depict the mean blood glucose levels (FIG. 23A) or C-peptide levels (FIG. 23B) over time after administration of IV, SC or TI (inhaled) insulin according to the teachings of the present invention.
Figure 23B:
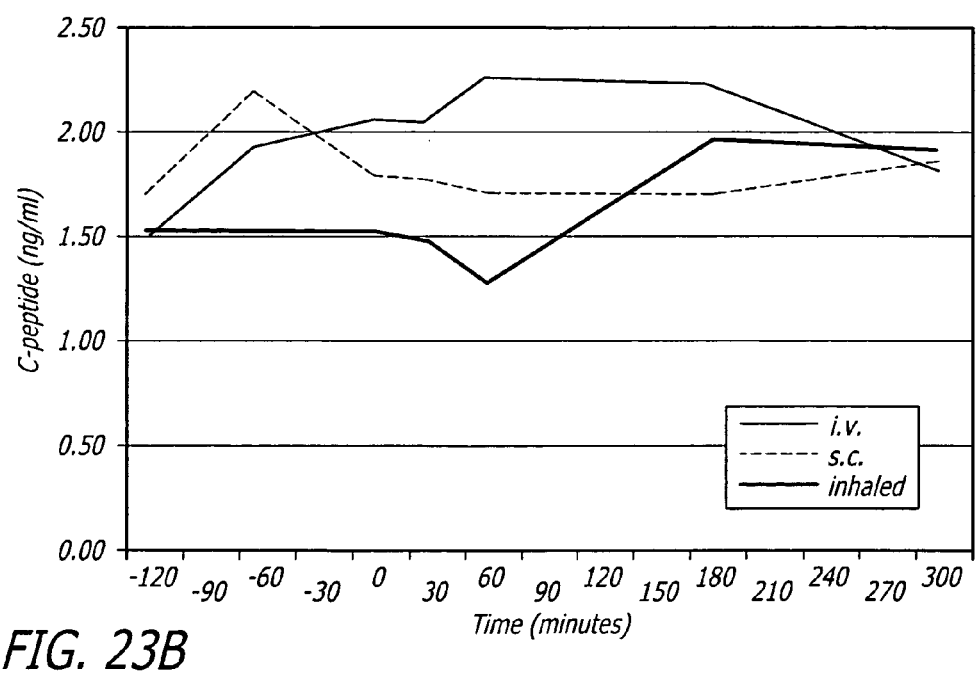
Figure 24A:
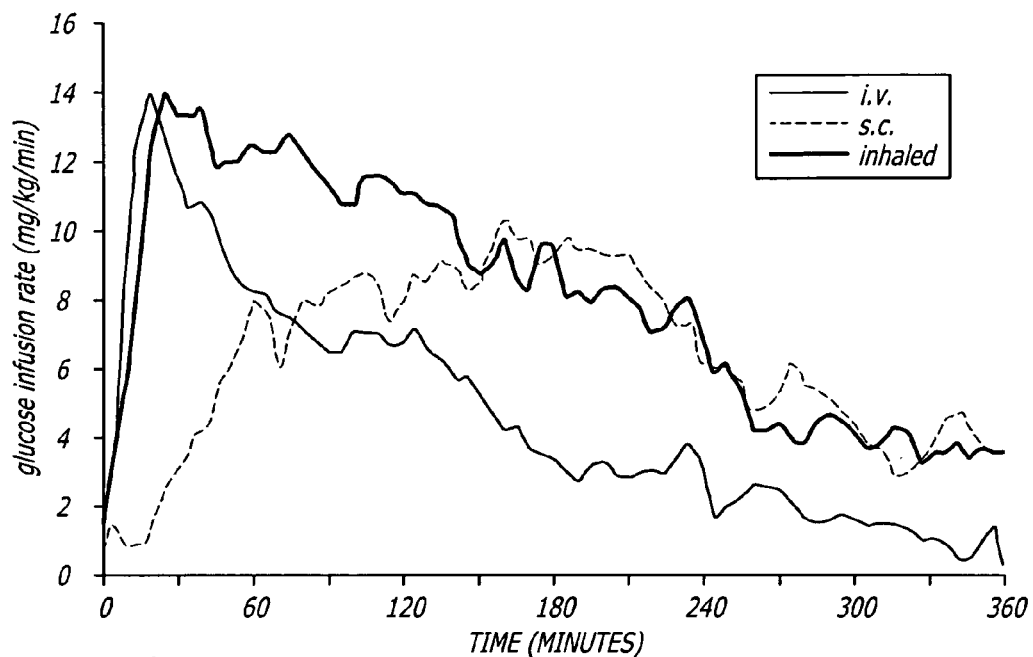
FIGS. 24A-B depict glucose infusion rate (FIG. 24A) or mean insulin concentration (FIG. 24B) over time after administration of IV, SC or TI (inhaled) insulin according to the teachings of the present invention.
Figure 24B:
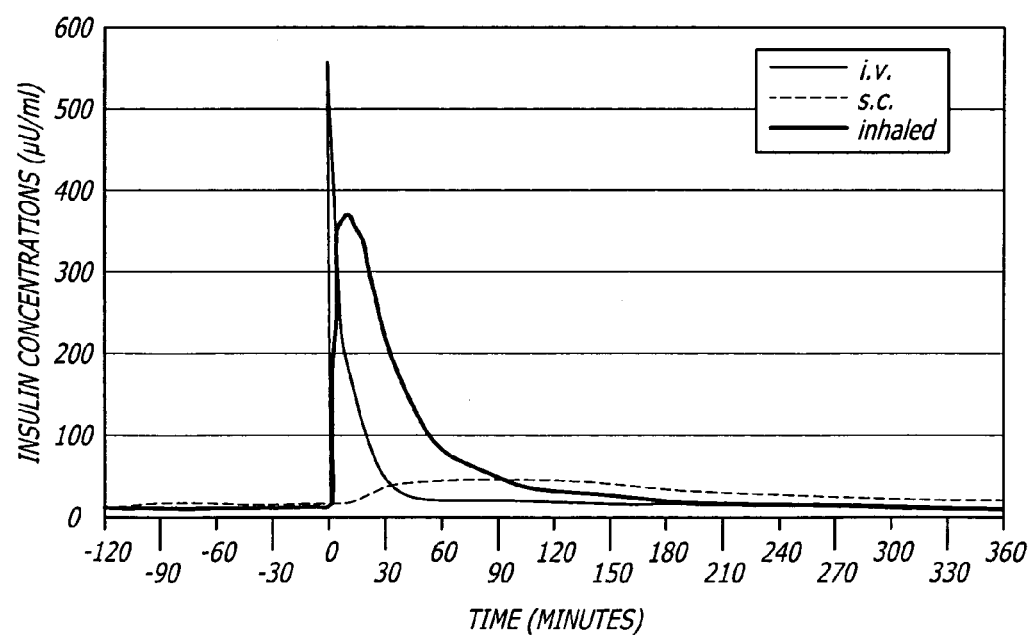

The pharmacokinetic results are illustrated in FIGS. 23 and 24 and in Table 8.

Efficacy Results

Inhalation of 100 U of Technosphere®/Insulin revealed a peak of insulin concentration after 13 min (intravenous (IV) (5 IU): 5 min, subcutaneous (SC) (10 IU): 121 min) and a return of the insulin levels to baseline after 180 min (IV: 60 min, SC: 360 min). Biological action as measured by glucose infusion rate peaked after 39 min IV: 14 min, SC: 163 min) and lasted for more than 360 min (IV: 240 min, SC: >360 min). Absolute bioavailability (comparison to IV application) was 14.6±5.1% for the first three hours and 15.5±5.6% for the first six hours. Relative bioavailability (comparison to SC application) was 25.8±11.7% for the first three hours and 16.4±7.9% for the first six hours.

TABLE 8

Pharmacokinetic Parameters after Pulmonary Administration of TI

| | Pharmacokinetic Parameters | | |
|---|---|---|---|
| | Intravenous Administration | Inhaled TI | Subcutaneous Administration |
| Parameter Calculated on Glucose Infusion Rate | | | |
| T50%* | 9 min | 13 min | 60 min |
| Tmax | 14 min | 39 min | 163 min |
| T-50%** | 82 min | 240 min | 240 min |
| T to baseline | 240 min | >360 min | >360 min |
| Parameter Calculated on Insulin Levels | | | |
| T50%* | 2 min | 2.5 min | 27 min |
| Tmax | 5 min | 13 min | 121 min |
| T-50%** | 6 min | 35 min | 250 min |
| T to baseline | 60 min | 180 min | 360 min |

*time from baseline to half-maximal values
**time from baseline to half-maximal after passing Tmax Safety Results Technosphere®/Insulin was shown to be safe in all patients. One patient was coughing during the inhalation without any further symptoms or signs of deterioration of the breathing system.

Conclusions

Inhalation of 100 U of Technosphere®/Insulin was well tolerated and was demonstrated to have a substantial blood glucose lowering effect with a relative bioavailability of 25.8% for the first three hours as calculated from the achieved serum insulin concentrations.

Summary

In this study, the inhalation of Technosphere®/Insulin was demonstrated in healthy human subjects to have a time-action profile with a rapid peak of insulin concentration ($T_{max}$: 13 min) and rapid onset of action ($T_{max}$: 39 min) and a sustained action over more than six hours. The total metabolic effect measured after inhalation of 100 U of Technosphere®/Insulin was larger than after subcutaneous injection of 10 IU of insulin. The relative bioefficacy of Technosphere®/Insulin was calculated to be 19.0%, while the relative bioavailability was determined to be 25.8% in the first three hours.

The data also show that inhalation of Technosphere®/Insulin resulted in a much more rapid onset of action than SC insulin injection that was close to the onset of action of IV insulin injection, while duration of action of Technosphere®/Insulin was comparable to that of SC insulin injection.

The drug was well tolerated and no serious adverse events were reported during the entire trial.

Example 8

Prandial Technosphere®/Insulin Provides Significantly Better Control of Meal-Related Glucose Excursions than Prandial Subcutaneous Insulin Technosphere®/Insulin (TI) is a dry powder formulation of human insulin comprising insulin complexed to fumaryl diketopiperazine microparticles. Technosphere®/Insulin was delivered by pulmonary administration with a dry powder inhaler (MedTone® Inhaler) accomplishing a rapid onset of action and a duration of action long enough to cover meal-related glucose absorption. The primary objective of this study was to assess safety and efficacy of pre-prandially administered TI compared to subcutaneous (SC) regular insulin on blood glucose concentration over a 7 day treatment period.

Sixteen non-smoking subjects with Type 2 diabetes (age 59 (range 39-69) yrs; BMI 29.6 (23.8-34.9) kg/m$^2$; mean diabetes duration 12.3 yrs; with normal pulmonary function (forced expiratory volume in 1 sec and forced vital capacity >80% of predicted normal) and treated with intensified insulin therapy were enrolled in this randomized, open-label, two period cross-over study. Subjects covered their prandial insulin needs either by inhaled TI or by SC insulin over a treatment period of one week, respectively, while continuing their usual basal insulin therapy. The doses of TI and SC insulin were determined during a 24 hours in-house period prior to randomization. TI was inhaled using a 12 U or 24 U cartridge via a hand-held inhaler. After an out-patient period during which subjects administered the assigned pre-meal therapy with either SC or TI, performed 4-point blood glucose self-measurements, and pursued their usual activities and diet for 5 to 7 days, postprandial blood glucose and serum insulin (INS) excursions were determined under in-house conditions after ingestion of a standardized breakfast (496 kcal, 55% carbohydrates) covered with either 48±9 (mean±SD) U of TI or 14±5 IU of SC insulin.

Figure 9B:
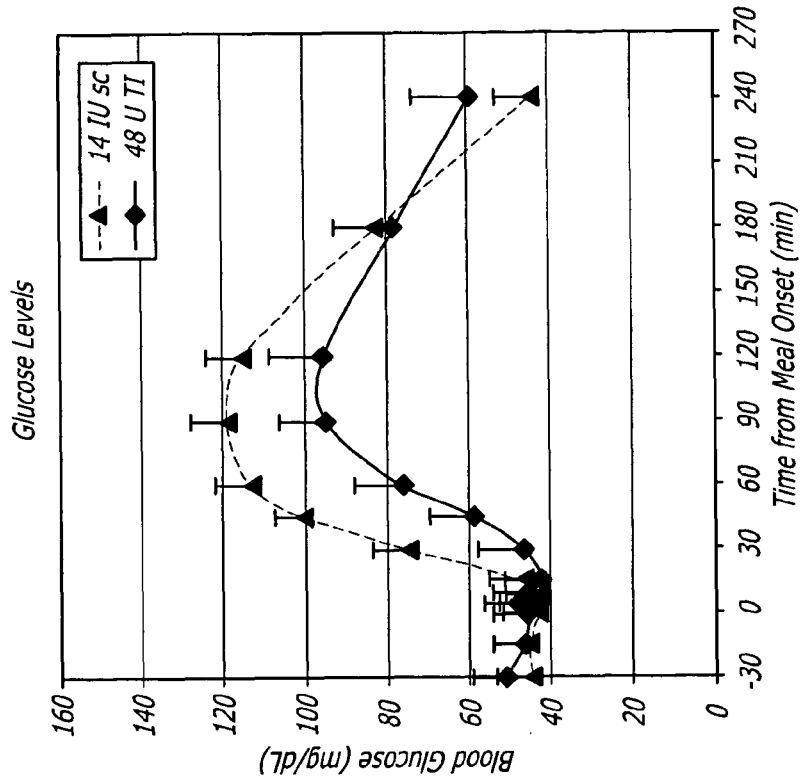
FIGS. 9A-B depict blood insulin (FIG. 9A) and glucose levels (FIG. 9B) in individuals with type 2 diabetes mellitus after administration of 14 IU SC insulin or 48 U Technosphere®/Insulin (TI) according to the teachings of the present invention.
Figure 9A:
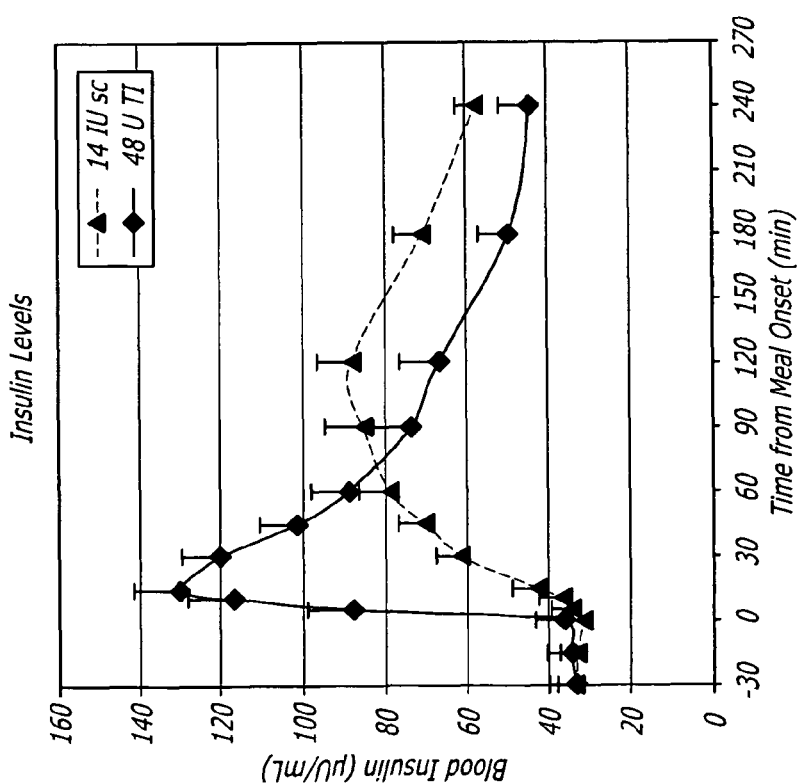
Figure 10:
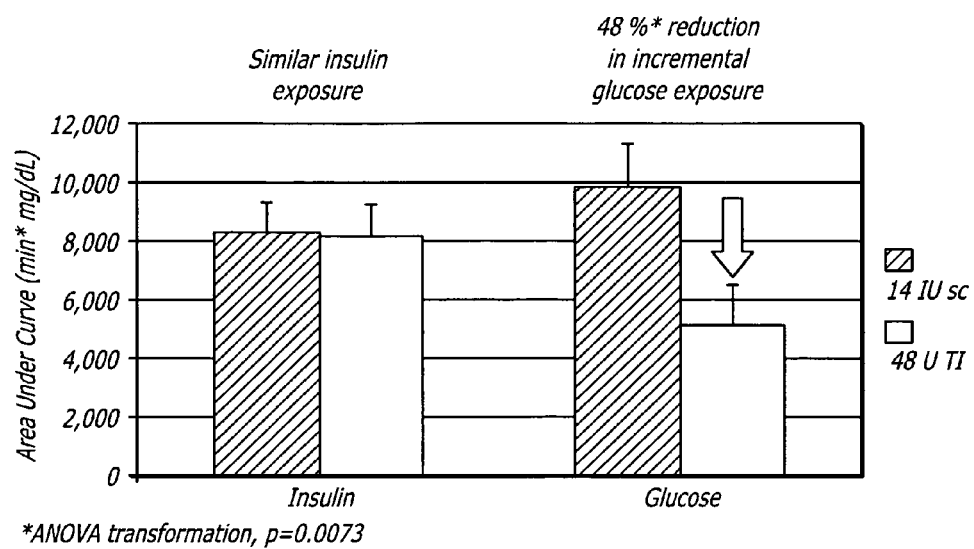
FIG. 10 depicts the improved postprandial glucose exposure with similar insulin exposure in individuals with type 2 diabetes mellitus after administration of 14 IU SC insulin or 48 U Technosphere®/Insulin (TI) according to the teachings of the present invention.

When treated with SC insulin, subjects demonstrated insulin median Tmax of 120 min with median Cmax of 54 µU/mL. In comparison, when treated with TI, subjects demonstrated insulin median Tmax of 14 min and median Cmax of 102 µU/mL (FIG. 9). Total insulin exposure for each treatment cycle was comparable for SC and for TI with mean $AUC_{INS}$ measured at 9155 and 9180 µU/mL respectively (FIG. 10). Mean excursion of glucose from baseline for SC was 85 mg/dL and $AUC_{GLU}$ was 10925 min*mg/dL. In comparison, mean excursion of glucose from baseline for TI was 59 mg/dL and $AUC_{GLU}$ was 6969 min*mg/dL (FIG. 10). Thus the ratio of glucose excursion to insulin exposure in the above units, an indication of the effectiveness of the absorbed insulin dose, was only about 0.76 versus about 1.2 for TI and SC, respectively. The data demonstrate a 31% reduction (p=0.0022) of mean glucose excursion and a 36% reduction (p=0.0073) of glucose exposure over the 240 min measured for TI relative to SC.

With comparable exposure to insulin (as measured in the plasma), to meal quantity, and to meal composition, prandial TI resulted in significantly improved control of post-prandial peak glucose and total glucose exposure compared to prandial SC. The only differences between therapies were the insulin formulations and the methods of insulin administration. TI provided insulin Tmax that mimicked first-phase insulin release kinetics and which occurred at a time when it would be expected to have an effect on hepatic glucose release. SC insulin levels were much lower than TI during the early post-prandial period, did not exhibit a clear "peak" as did TI, and demonstrated a slow rise to maximum concentration—too late to be expected to control hepatic glucose release but sufficient to represent a risk for late post-prandial hypoglycemia.

Example 9

Markedly Reduced Postprandial Glucose Excursions through Inhaled Technosphere®/Insulin in Comparison to SC Injected Regular Insulin in Subjects with Type 2 Diabetes Baseline adjusted postprandial total insulin exposure (INS-$AUC_{0-240}$ min) was comparable for TI and for SC (8187±4269 vs 8302±4025 min*µU/dL; ns) whereas baseline adjusted postprandial glucose excursion. (BG-$AUC_{0-240}$ min) for TI was only about 50% of that of SC (5095±5923 min*mg/dL vs 9851±5593 min*mg/dL; p<0.008). Thus the ratio of glucose excursion to insulin exposure in the above units, an indication of the effectiveness of the absorbed insulin dose was only about 0.62 for TI versus about 1.2 for SC. In other words, unit for unit of absorbed insulin TI was nearly twice as efficient in removing glucose from the blood. With TI median insulin Tmax was shorter (15 vs 120 min; p<0.001) and median Cmax was higher (100 vs 54 µU/mL; p=0.001) than with SC. Accordingly, postprandial maximum adjusted blood glucose excursions were 28% lower with TI compared to SC (49 vs 82 mg/dL; p<0.003). The incidence of hypoglycemia (BG <63 mg/dL or hypoglycemic symptoms) was comparable between TI and SC (6 vs. 5 episodes) as was the number of treatment emerged (mild to moderate) adverse events (5 vs. 4 episodes). Hyperglycemia (BG >280 mg/dL) occurred more often with TI (12 vs. 4 episodes)—with two patients alone accounting for 8 episodes.

Technosphere®/Insulin markedly improved post-prandial glucose control compared to prandial SC while total serum insulin concentrations were comparable between both treatments. This was attributed to a rapid onset of action of TI in which insulin Tmax resembles first-phase insulin release kinetics. In contrast SC insulin levels were much lower than TI during the early post-prandial period and did not exhibit the clear peak observed with TI. These results support the conclusion that preprandial TI was superior to SC insulin in providing prandial insulin needs and reducing meal related blood glucose excursions.

Example 10

The Variability and Time-Action Profile of Inhaled Technosphere®/Insulin Compares Favorably to that of Subcutaneous Human Regular Insulin Timing and reproducibility and of insulin's metabolic effect is critical to achieve near-normal glucose control and to enable patients to make appropriate dose adjustments. The time-action profiles and the intra-subject variability in insulin absorption and insulin effect between repeated doses of 48 U inhaled Technosphere®/Insulin (TI) and 24 IU subcutaneous injected human regular insulin (SC) was compared.

Technosphere®/Insulin and SC were given on three separate occasions each on separate study days in a randomized sequence in 12 insulin-treated subjects with type 2 diabetes (10 males, 2 females, age 56 (range 40-65) years, diabetes duration 14.4 (3-29) years, HbA1c 6.9±0.9% (mean±SD), all normal lung function (FVC, FEV1 and VC=80% of predicted normal)). Using a euglycemic glucose clamp (clamp level 120 mg/dL), pharmacokinetic (PK) and pharmacodynamic (PD) time-action profiles were measured over 540 min following each form of insulin administration. Variability of absorption and effect, expressed as CV % of $AUC_{0-1}$, was determined at 120, 180 and 540 min after dosing.

Technosphere®/Insulin showed a more rapid onset of action and higher peak insulin concentrations (INS) than SC (table, INS-tmax 17±6 vs. 135±68 min, TI vs. SC, p<0.0001). Technosphere®/Insulin reached maximal glucose infusion rate (GIR) values already at 79±47 min, while the maximum effect of the SC dose occurred at 293±83 min (p<0.00001). The AUCs for both INS and GIR curves were higher for TI compared to SC in the first two and three hours after administration (Table 9). The variability in both insulin concentrations and insulin action was lower for TI compared to SC in the first three hours after administration (Table 9). At 270 min, GIR for TI had returned to baseline, and the variability in measured plasma insulin at 540 min was comparable to the variation of SC (CV %: GIR-AUC$_{0-540}$ min 26% vs. 18% (TI vs. SC); INS-AUC$_{0-540}$ min 16% vs. 15%).

Technosphere®/Insulin showed a more rapid onset and a shorter duration of action than subcutaneous human regular insulin which can make it suitable for replacement of prandial insulin secretion in patients with type 2 diabetes. In particular, TI can provide a lower risk of late postprandial hypoglycemia as, in contrast to SC, most of its glucose lowering effect occurred before the three hour point. Furthermore, the intra-patient variability of repeated inhalations of TI was superior to SC insulin during the first three hours after dosing which can facilitate dose titration.

TABLE 10

Pharmacokinetic Parameters after Pulmonary Administration of TI

| | Inhaled Technosphere ® Insulin | | SC Human Regular Insulin | |
|---|---|---|---|---|
| | mean ± SD | CV (%) [95% CI] | mean ± SD | CV (%) [95% CI] |
| Pharmacodynamic (PD) Parameters, based on glucose infusion rates (GIR) | | | | |
| GIR-AUC$_{0-2h}$ (mg/kg) | 265 ± 83 (44% of total) | 23.4 [13.9–33.0] | 211 ± 84 (16% of total) | 39.2 [23.2–55.2] |
| GIR-AUC$_{0-3h}$ (mg/kg) | 355 ± 119 (59% of total) | 21.7 [12.9–30.6] | 363 ± 153 (27% of total) | 33.4 [19.8–47.1] |
| GIR$_{max}$ (mg/kg/min) | 4.5 ± 1.0† | 22.0 [13.0–30.9] | 5.5 ± 1.4 | 17.3 [10.3–24.4] |
| Pharmacokinetic (PK) Parameters, based on plasma insulin (INS) concentrations | | | | |
| INS-AUC$_{0-2h}$ (µU/ml) | 6965 ± 2233* (56% of total) | 19.1 [11.3–26.9] | 5509 ± 1094 (24% of total) | 27.1 [16.1–38.2] |
| INS-AUC$_{0-3h}$ (µU/ml) | 8030 ± 2561 (64% of total) | 18.2 [10.8–24.6] | 8672 ± 1442 (38% of total) | 25.0 [14.8–35.2] |
| INS-C$_{max}$ (µU/ml) | 124 ± 44† | 20.4 [12.1–28.8] | 63 ± 10 | 29.2 [17.3–41.2] |

CI: Confidence Interval
*p < 0.05 vs. SC,
†p < 0.0005 vs. SC (ANOVA, Mixed Effects Models)

Example 11

Multi-Center Study of Type 2 Patients Taking Prandial TI in an Ambulatory Setting Studies of the pharmacokinetics and pharmacodynamics of administering regular human insulin by pulmonary inhalation using Technosphere®/Insulin (TI) have indicated that maximal plasma insulin concentration can be achieved in a median of about 10 to 14 minutes after inhalation, which is ideal for replicating the first-phase insulin release. The administration of insulin with this highly reproducible kinetic profile to ambulatory patients with diabetes has not been possible with other currently available insulin systems. Studies, such as the examples above, have demonstrated a 48% reduction in post-prandial glucose excursion with TI compared to a bio-available equivalent dose of subcutaneous insulin (SC) given before meals. In another multi-center study of type 2 patients taking prandial TI in an ambulatory setting for 12 weeks, the frequency of prospectively monitored hypoglycemia was less than 10% of the frequency historically reported for SC in ambulatory use.

In a randomized, prospective double blind, placebo controlled study of the forced titration of prandial Technosphere®/Insulin in patients with type 2 diabetes mellitus subjects received inhaled Technosphere®/Insulin (TI), dosed prandially, in addition to basal administration of SC insulin glargine (Lantus®; a form of long acting insulin), 227 patients were studied over 18 weeks. During the initial 4-weeks, patients were followed on their existing therapy and then removed from all oral anti-hyperglycemic therapy and placed on fixed doses of SC insulin glargine taken once daily, in a dose sufficient to replicate their documented pre-manipulation fasting plasma glucose levels and stabilized at this dose. The patients were then randomized to blinded doses of added inhaled placebo or blinded doses of inhaled TI containing 14, 28, 42 or 56 U of regular human insulin taken at the time of each main meal of the day in a forced titration scenario over 4 weeks. Specifically, the subjects, divided into five cohorts, initially received placebo (Technosphere® microparticles without any insulin) along with the sc long acting insulin. After a week one cohort continued to receive placebo and four cohorts were switched to a TI dose of 14 U of insulin. After another week three cohorts were switched to a TI dose of 28 U, and so on until a final cohort reached a TI dose of 56 U. All cohorts then continued on the same dose for the remaining eight weeks of the trial.

HbA1c levels and meal challenges (300 min) were evaluated at the initial visit, at the start of randomized treatment and at completion. Comparisons were made between treatment groups and the placebo group. Safety was assessed by the frequency of defined hypoglycemic episodes and by the measurement of serial pulmonary function tests including FEV$_1$ and DL$_{CO}$. The addition of TI to insulin glargine produced a dose-dependent reduction in HbA1c levels. In patients treated for eight weeks at 56 units, the mean reduction was 0.79% greater than that observed in the insulin glargine/placebo group (p=0.0002). TI also produced a dose-dependent reduction in post-prandial glucose excursions with a maximal excursion averaging only 34 mg/dL at 56 U (p<0.0001). There were no severe hypoglycemic episodes, and the frequency of mild/moderate hypoglycemic episodes was not increased above that in subjects on insulin glargine alone. No changes were observed from baseline or between dosage groups in weight or pulmonary function. Thus inhaled Technosphere®/Insulin was able to improve the glycemic control of patients with type 2 diabetes without increasing the risk of hypoglycemia.

Example 12

A 3 Month Comparison in Type 1 Diabetes of Inhaled Technosphere®/Insulin to SC Administered Rapid-Acting Insulin Analogue as Prandial Insulin in a Basal/Prandial Regimen This study represents the first evaluation of long-term control in patients with type 1 diabetes, comparing Technosphere®/Insulin (TI) with a rapid-acting insulin analogue (RAA, Novolog®) as a comparator. Previous studies of has shown significantly better postprandial control than regular human insulin over 240 min in patients with type 2 diabetes.

Patients with type 1 diabetes (111 subjects, 18 to 80 years of age; HbA1c≥7.0% and ≤11.5%) were enrolled in a randomized, open label study to receive TI or RAA as meal-time insulin in addition to basal insulin (Lantus®) for 12 weeks. Titration of both prandial and basal insulin was permitted at the physicians discretion. At baseline, week 8 and week 12, standardized meal tests were conducted to assess glucose excursions over 300 min (420 min at week 12), and HbA1c levels and lung function ($FEV_1$ and DLco) was evaluated in both groups. Lower maximum and total glucose excursions were observed in the first two hours following a standard meal in the group receiving TI insulin compared to those who were dosed with sc insulin. Over the following 3-4 hours, glycemia was maintained close to baseline levels in the TI group but fell below baseline in the patients receiving rapid acting insulin. No difference in HbA1c levels were observed between the two treatment groups. No adverse effects on pulmonary function were noted during the course of the study. Therefore, in a basal/prandial regimen in patients with type 1 diabetes, inhaled TI is an appropriate alternative to SC administered RAA and may offer the advantages of reducing both glucose excursions and the risk of late postprandial hypoglycemia.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of potentiating the glucose elimination rate in a human patient with diabetes comprising:
    producing a spike in serum insulin concentration with an exogenously-administered inhaled insulin composition, wherein said spike comprises the maximum serum insulin concentration which is obtained by about 20 minutes after administration of said inhaled insulin composition, and wherein said exogenously-administered inhaled insulin composition is administered from approximately 10 minutes prior to a meal to approximately 30 minutes after a meal, wherein said glucose elimination rate returns to baseline by about 6 hours after administration.

2. The method of claim 1 wherein said diabetes is type 2 diabetes.

3. The method of claim 1 wherein said maximum serum insulin concentration is about 75 mU/L or greater than 75 mU/L.

4. The method of claim 3 wherein said maximum serum insulin concentration is about 100 mU/L or greater than 100 mU/L.

5. The method of claim 4 wherein said maximum serum insulin concentration is about 125 mU/L or greater than 125 mU/L.

6. The method of claim 1 wherein said maximum serum insulin concentration is achieved within about 15 minutes.

7. The method of claim 6 wherein said maximum serum insulin concentration is achieved within about 10 minutes.

8. The method of claim 1 wherein said potentiation comprises the glucose elimination rate reaching its maximum within about 30 to 90 minutes after administration of said inhaled insulin composition.

9. The method of claim 8 wherein said potentiation comprises the glucose elimination rate reaching its maximum within about 1 hour.

10. The method of claim 9 wherein said potentiation comprises the glucose elimination rate reaching its maximum within about 45 minutes.

11. The method of claim 1 wherein said serum insulin concentration descends through half-maximal by about 80 minutes after said maximum serum insulin concentration is achieved.

12. The method of claim 11, wherein said serum insulin concentration descends through half-maximal by about 50 minutes after said maximum serum insulin concentration is achieved.

13. The method of claim 1 wherein said glucose elimination rate continues to rise after serum insulin concentration begins to fall.

14. The method of claim 1 wherein said glucose elimination rate begins to fall by about 1 hour after insulin administration.

15. The method of claim 1 wherein said exogenously-administered inhaled insulin composition comprises a complex between a diketopiperazine and human insulin.

16. The method of claim 15 wherein said diketopiperazine is fumaryl diketopiperazine.

17. A method of treating an insulin-related disorder comprising:
administering to a human patient having diabetes an exogenously-administered inhaled insulin composition such that said exogenously-administered inhaled insulin composition produces a spike in serum insulin concentration wherein said spike comprises the maximum serum insulin concentration which is achieved by about 20 minutes after administration of said inhaled insulin composition, and wherein said exogenously-administered inhaled insulin composition is administered from approximately 10 minutes prior to a meal to approximately 30 minutes after a meal, and wherein the glucose elimination rate of the human patient returns to baseline by about 6 hours after administration.

18. The method of claim 17 wherein said exogenously-administered inhaled insulin composition comprises a complex between a diketopiperazine and human insulin.

19. The method of claim 18 wherein said diketopiperazine is fumaryl diketopiperazine.

20. The method of claim 17 wherein said diabetes is type 2 diabetes.

21. The method of claim 17 further comprising administering a long-acting basal insulin.

22. The method of claim 17 wherein said serum insulin concentration descends through half-maximal by about 80 minutes after said maximum serum insulin concentration is achieved.

23. The method of claim 22 wherein said serum insulin concentration descends through half-maximal by about 50 minutes after said maximum serum insulin concentration is achieved.

24. A method of maintaining blood glucose levels in a human patient with diabetes in a normal range comprising:
providing an exogenously-administered inhaled insulin composition, such that said exogenously administered inhaled insulin composition produces a spike in serum insulin concentration comprising maximum serum insulin concentration achieved within about 30 minutes of administration of said inhaled insulin composition, and wherein said exogenously-administered inhaled insulin composition is administered from approximately 10 minutes prior to a meal to approximately 30 minutes after a meal, and wherein the glucose elimination rate of the human patient returns to baseline by about 6 hours after administration.

25. The method of claim 24 wherein said maximum serum insulin concentration is obtained within about 15 minutes of administration.

26. The method of claim 25 wherein said exogenously-administered inhaled insulin composition comprises a complex between a diketopiperazine and human insulin.

27. The method of claim 26 wherein said diketopiperazine is fumaryl diketopiperazine.

28. The method of claim 24 wherein said exogenously-administered inhaled insulin composition is a non-naturally occurring form of insulin.

29. The method of claim 24 wherein said serum insulin concentration descends through half-maximal by about 80 minutes after said maximum serum insulin concentration is achieved.

30. The method of claim 29 wherein said serum insulin concentration descends through half-maximal by about 50 minutes after said maximum serum insulin concentration is achieved.

* * * * *

UNITED STATES PATENT AND TRADEMARK OFFICE
CERTIFICATE OF CORRECTION

| | | |
|---|---|---|
| PATENT NO. | : 9,006,175 B2 | Page 1 of 1 |
| APPLICATION NO. | : 11/329686 | |
| DATED | : April 14, 2015 | |
| INVENTOR(S) | : Anders Hasager Boss et al. | |

It is certified that error appears in the above-identified patent and that said Letters Patent is hereby corrected as shown below:

ON THE TITLE PAGE

Item (60) in the Related U.S. Application Data, "Continuation of application 10/719,734" should be changed to --Continuation-in-part of application 10/719,734--.

Signed and Sealed this
Twentieth Day of October, 2015

Michelle K. Lee
*Director of the United States Patent and Trademark Office*